(12) United States Patent
Owusu

(10) Patent No.: US 10,695,614 B2
(45) Date of Patent: Jun. 30, 2020

(54) SYSTEM AND METHOD FOR MONITORING OR ASSESSING PHYSICAL FITNESS FROM DISPARATE EXERCISE DEVICES AND ACTIVITY TRACKERS

(71) Applicant: Jaxamo Ltd, Dunstable, Bedfordshire (GB)

(72) Inventor: Stephen Owusu, Newcastle, WA (US)

(73) Assignee: Jaxamo LTD, Bedfordshire (GB)

( * ) Notice: Subject to any disclaimer, the term of this patent is extended or adjusted under 35 U.S.C. 154(b) by 0 days.

(21) Appl. No.: 16/425,289

(22) Filed: May 29, 2019

(65) Prior Publication Data

US 2020/0114204 A1 Apr. 16, 2020

Related U.S. Application Data

(63) Continuation-in-part of application No. 16/160,399, filed on Oct. 15, 2018.
(Continued)

(51) Int. Cl.
*A63B 24/00* (2006.01)
*A61B 5/00* (2006.01)
(Continued)

(52) U.S. Cl.
CPC ...... *A63B 24/0062* (2013.01); *A63B 24/0087* (2013.01); *A61B 5/1118* (2013.01);
(Continued)

(58) Field of Classification Search
CPC ..... A61B 5/1118; A61B 5/222; A61B 5/6887; A63B 24/0062; A63B 24/0087;
(Continued)

(56) References Cited

U.S. PATENT DOCUMENTS 6,540,650 B1 4/2003 Krull
6,746,381 B2 6/2004 Krull
(Continued)

FOREIGN PATENT DOCUMENTS

| CN | 201823224 U | 5/2011 |
| EP | 2269701 A2 | 1/2011 |
| TW | M534015 U | 12/2016 |

OTHER PUBLICATIONS

International Search Report and Written Opinion for International Application No. PCT/EP2019/052491, dated Jun. 28, 2019, 18 pages.
(Continued)

*Primary Examiner* — Megan Anderson
(74) *Attorney, Agent, or Firm* — RatnerPrestia

(57) ABSTRACT

Physical fitness assessment systems and methods and wellness assessment systems and methods are disclosed. One physical fitness assessment system includes an exercise device and a host computer. The exercise device is configured to track movement of the exercise device by a user, determine a current physical activity data of the user based on, at least, the tracked movement, and transmit the current physical activity data of the user. The host computer is configured to receive from the exercise device the current physical activity data of the user, receive a physical fitness assessment selection to apply to the current physical activity date, compare the current physical activity data against benchmark physical activity data correlated with the exercise device, determine a physical fitness assessment of the user, generate the physical fitness assessment image based on the physical fitness assessment of the user, and present the physical fitness assessment image.

16 Claims, 34 Drawing Sheets

Related U.S. Application Data

(60) Provisional application No. 62/797,794, filed on Jan. 28, 2019.

(51) Int. Cl.
*A61B 5/11* (2006.01)
*A61B 5/22* (2006.01)

(52) U.S. Cl.
CPC ............. *A61B 5/222* (2013.01); *A61B 5/6887* (2013.01); *A63B 24/0075* (2013.01); *A63B 2024/0065* (2013.01); *A63B 2024/0068* (2013.01); *A63B 2220/17* (2013.01); *A63B 2220/40* (2013.01); *A63B 2225/50* (2013.01)

(58) Field of Classification Search
CPC .... A63B 2024/0065; A63B 2024/0068; A63B 2220/17; A63B 2220/40; A63B 2220/50
See application file for complete search history.

(56) References Cited

U.S. PATENT DOCUMENTS

| | | | |
|---|---|---|---|
| 7,491,157 B1 | 2/2009 | Lin | |
| 7,614,983 B1 | 11/2009 | Krull | |
| 7,762,933 B1 | 7/2010 | Yu | |
| 7,811,201 B1 * | 10/2010 | Mikan | A63B 24/0062 482/4 |
| 7,976,443 B2 | 7/2011 | Krull | |
| 7,981,012 B1 | 7/2011 | Krull | |
| 7,981,013 B2 | 7/2011 | Krull | |
| 8,021,282 B2 | 9/2011 | Polevoy et al. | |
| 8,128,537 B2 | 3/2012 | Signorile et al. | |
| 8,568,280 B2 | 10/2013 | Mendoza | |
| 8,727,947 B2 * | 5/2014 | Tagliabue | A63B 24/0062 482/8 |
| 8,771,153 B2 | 7/2014 | Dalebout et al. | |
| 8,784,280 B2 | 7/2014 | Krull | |
| 8,870,719 B2 | 10/2014 | Johnson et al. | |
| 9,310,909 B2 * | 4/2016 | Myers | A61B 5/1118 |
| 9,589,445 B2 * | 3/2017 | White | A43B 3/0005 |
| 9,814,922 B2 | 11/2017 | Moran et al. | |
| 10,111,589 B2 * | 10/2018 | Kirby | G06F 19/3418 |
| 10,166,429 B2 | 1/2019 | Chen | |
| 10,195,477 B2 | 2/2019 | Marjama et al. | |
| 10,229,192 B2 * | 3/2019 | Peters | G06F 16/337 |
| 10,420,978 B2 | 9/2019 | Wang | |
| 2007/0135274 A1 | 6/2007 | Blateri | |
| 2008/0081744 A1 | 4/2008 | Gormley | |
| 2014/0074265 A1 * | 3/2014 | Arginsky | A63B 71/0622 700/91 |
| 2014/0164611 A1 * | 6/2014 | Molettiere | A61B 5/1112 709/224 |
| 2015/0273272 A1 | 10/2015 | Wang | |
| 2015/0360073 A1 | 12/2015 | Moran et al. | |
| 2016/0089575 A1 | 3/2016 | Smith et al. | |
| 2016/0196326 A1 * | 7/2016 | Andon | G06F 7/02 707/740 |
| 2017/0333754 A1 * | 11/2017 | Rider | A63B 21/06 |
| 2018/0036578 A1 | 2/2018 | Moran et al. | |
| 2018/0264308 A1 | 9/2018 | Wang et al. | |
| 2018/0353794 A1 | 12/2018 | Wang | |

OTHER PUBLICATIONS

Design U.S. Appl. No. 29/635,801, filed Feb. 2, 2018—36 pages.
Non Final Office Action for U.S. Appl. No. 16/570,306, dated Jan. 3, 2020, 52 pages.

* cited by examiner

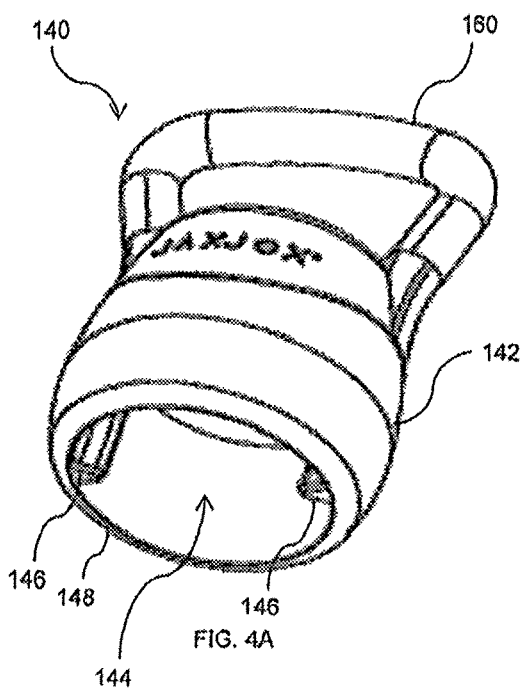
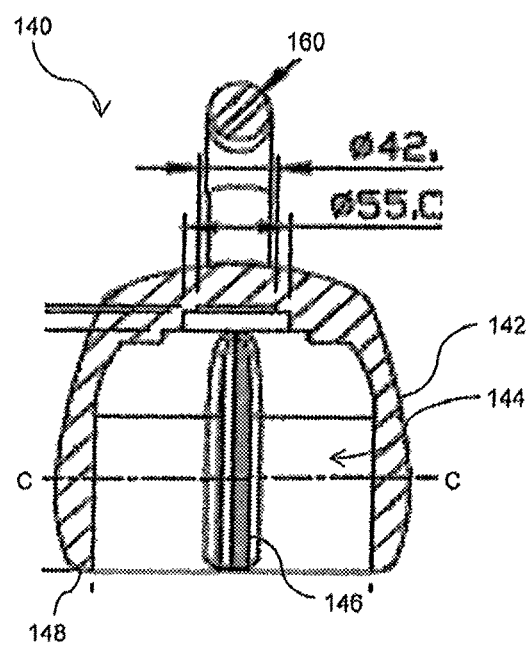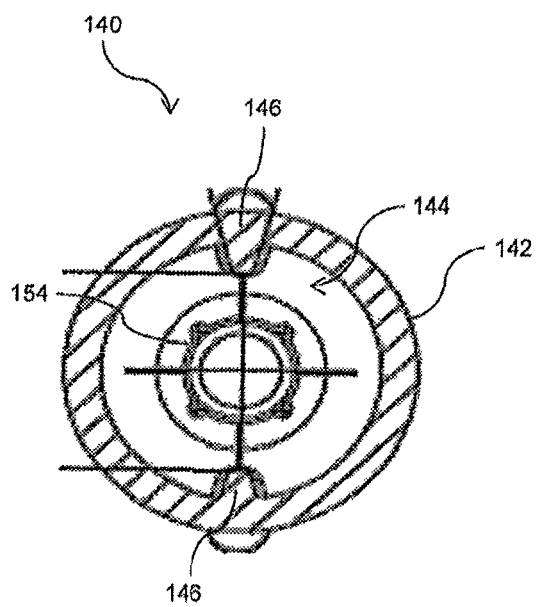
FIG. 4A
FIG. 4B
FIG. 4C

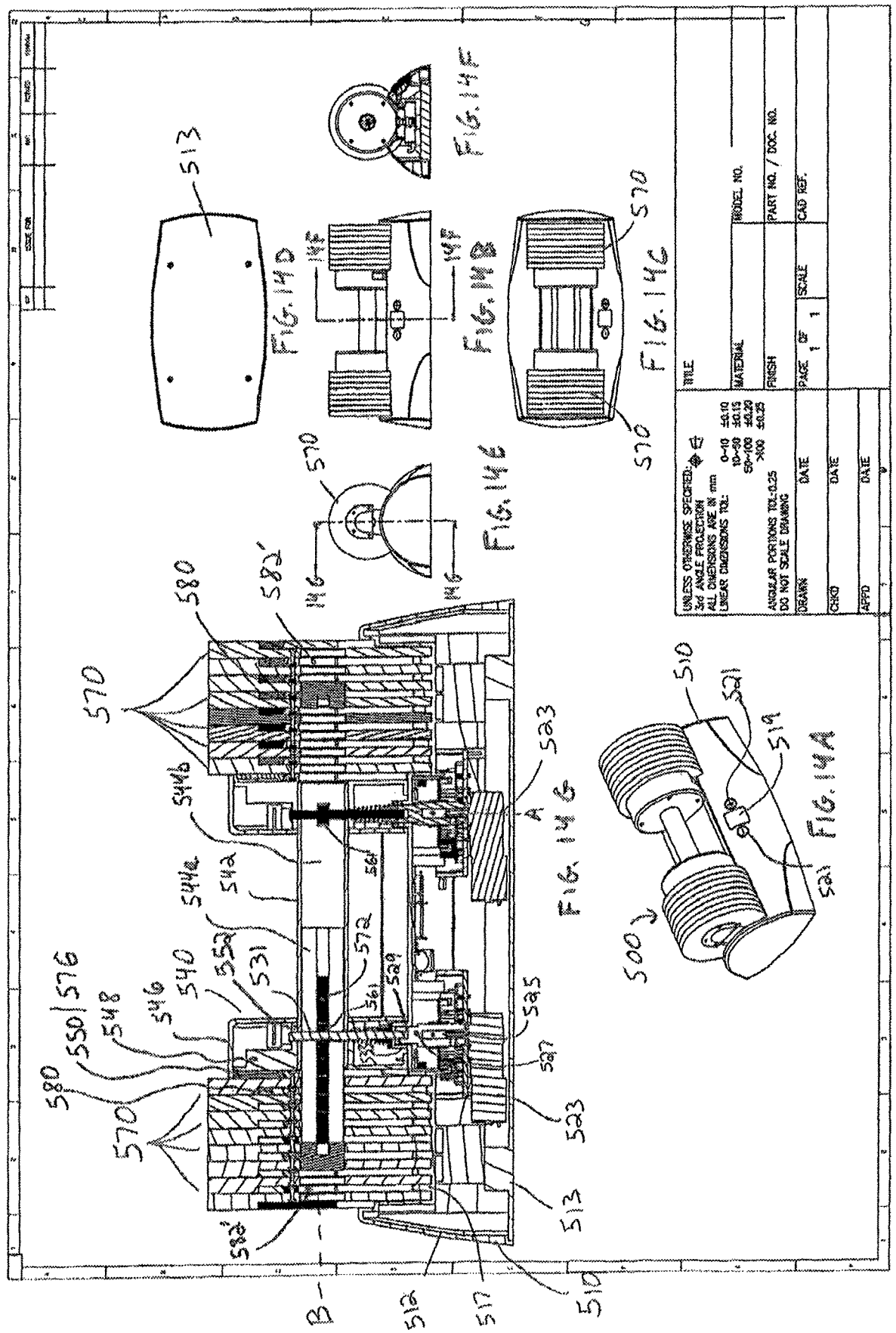

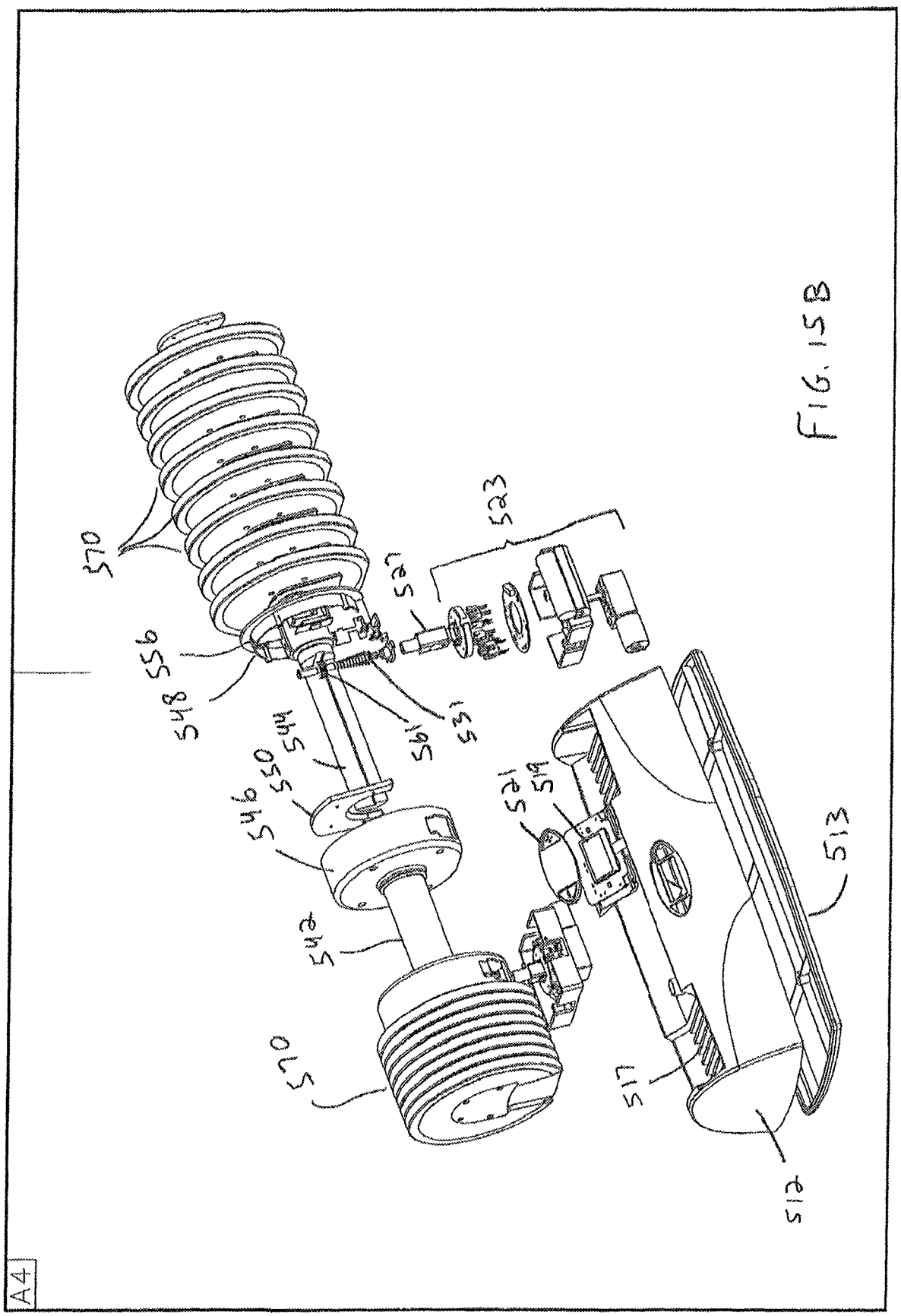

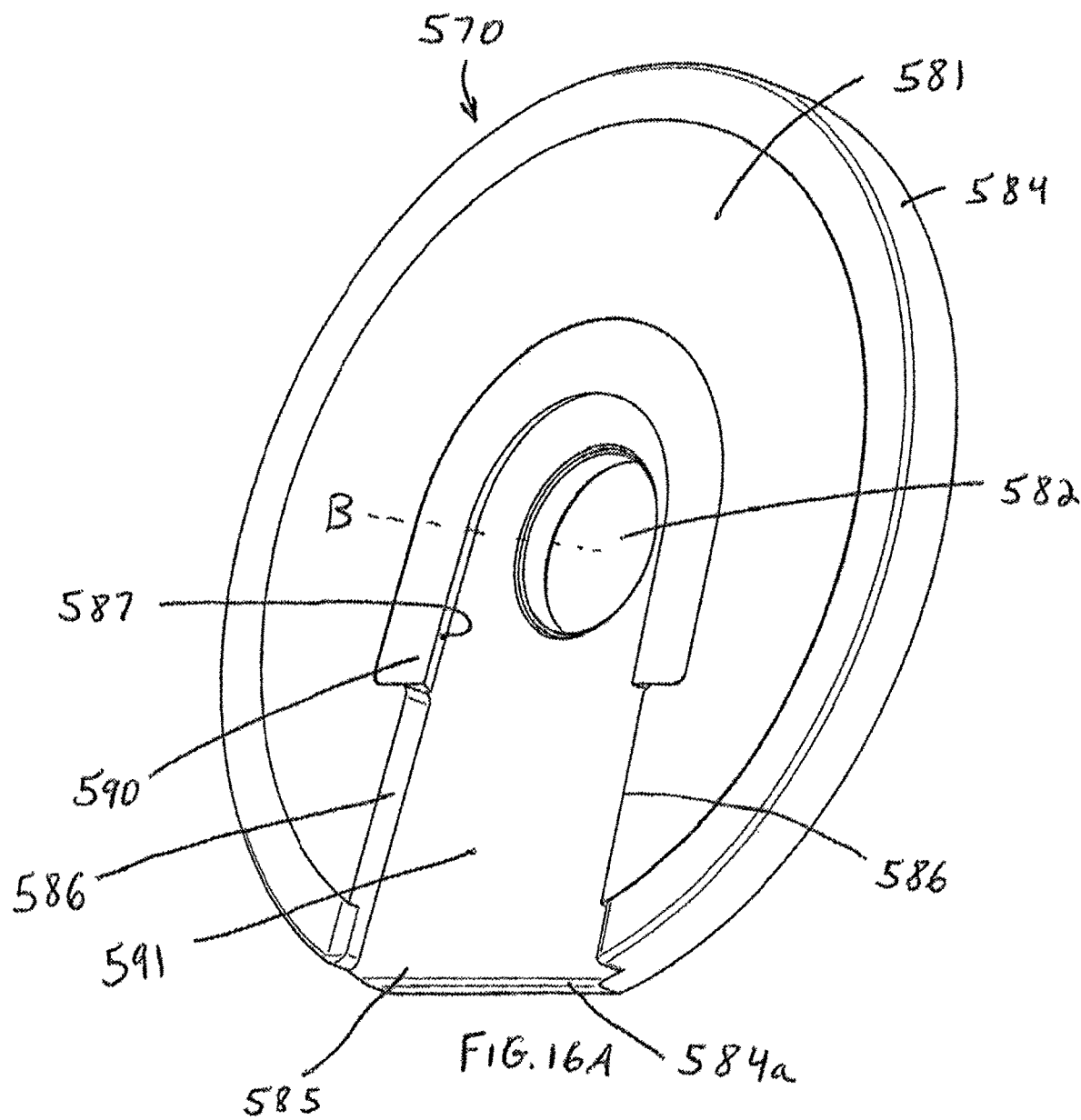

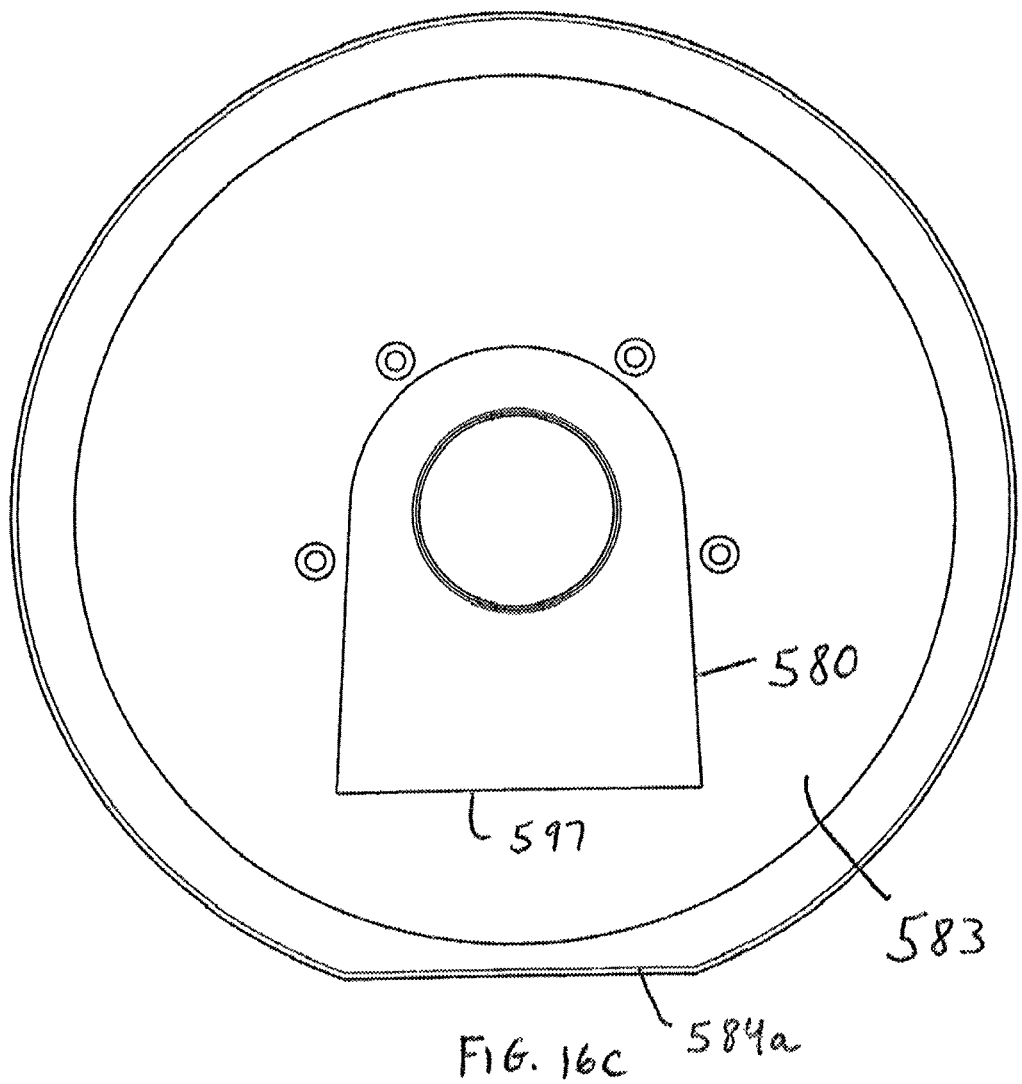

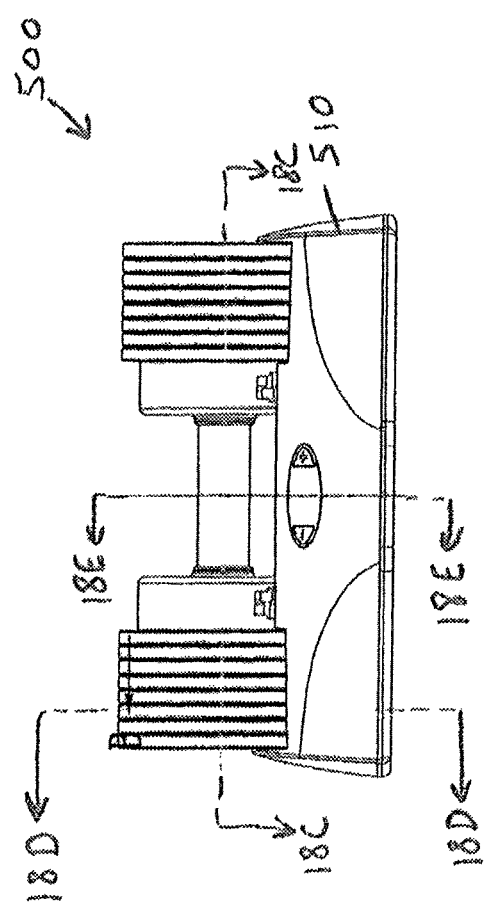

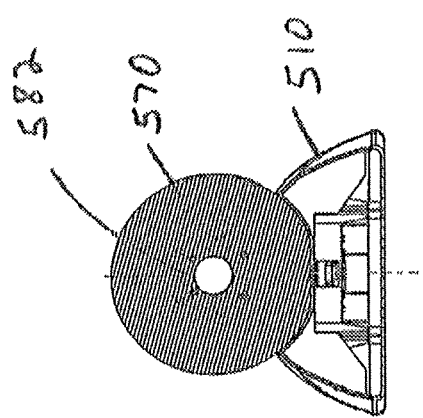

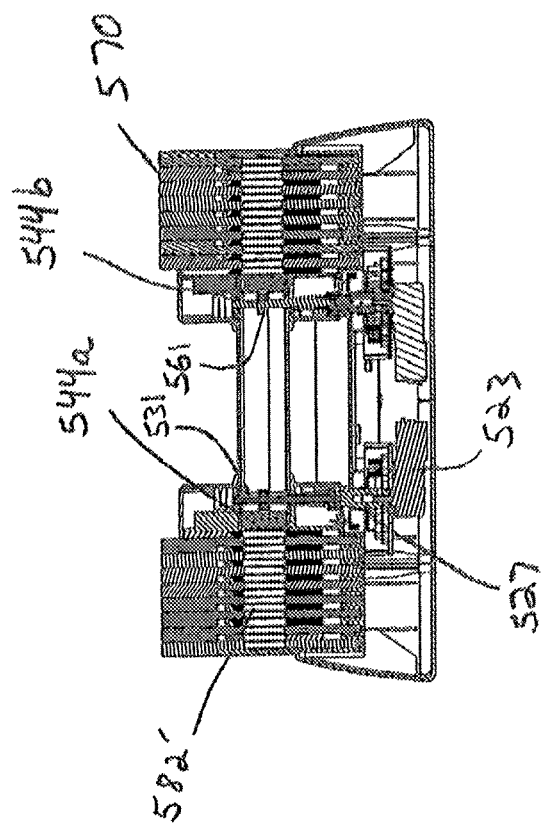

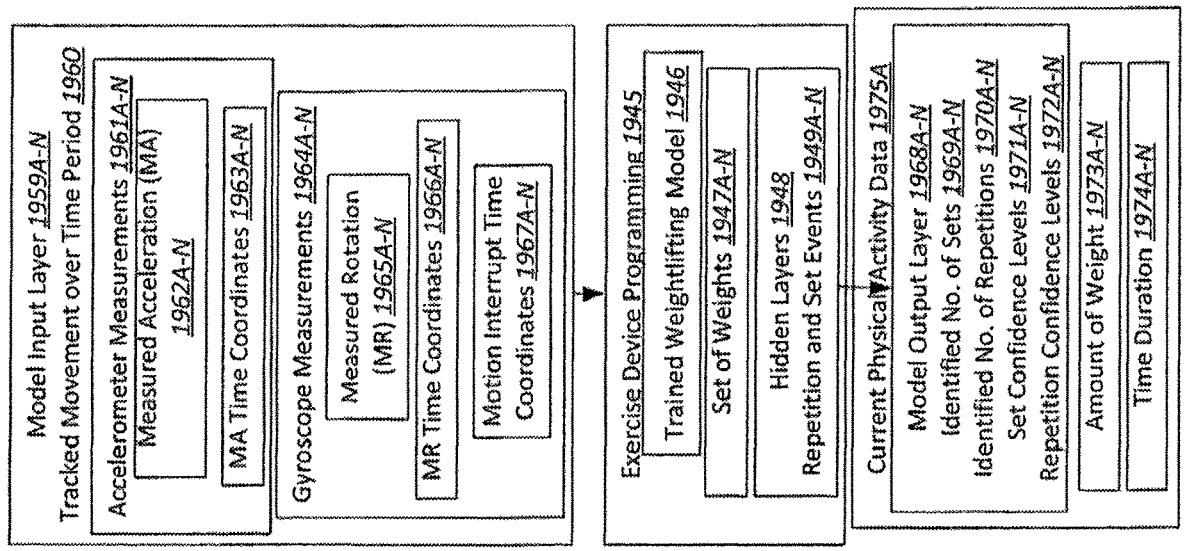
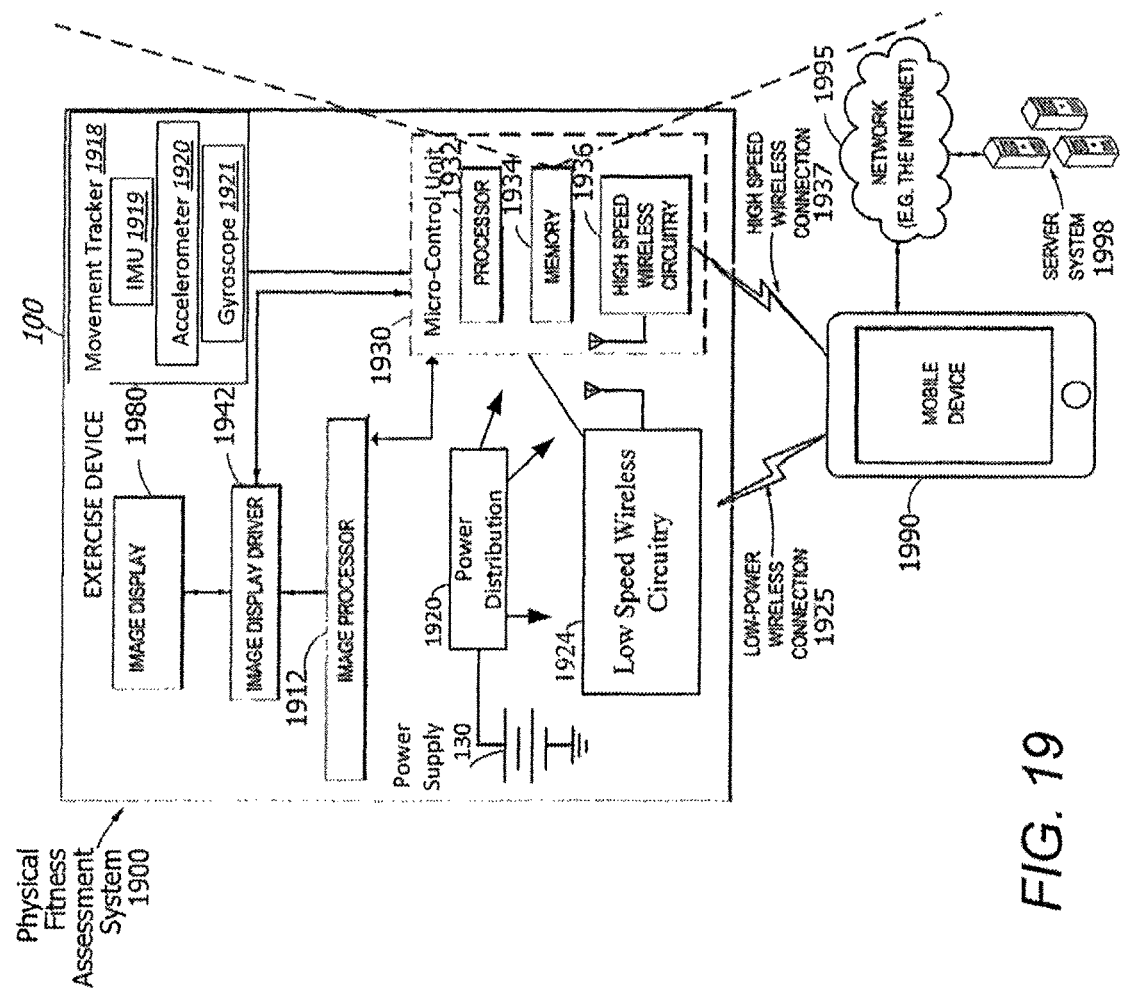
FIG. 19

SYSTEM AND METHOD FOR MONITORING OR ASSESSING PHYSICAL FITNESS FROM DISPARATE EXERCISE DEVICES AND ACTIVITY TRACKERS

CROSS-REFERENCE TO RELATED APPLICATIONS

The present application claims priority to U.S. Patent Application No. 62/797,794, filed Jan. 28, 2019, and is a continuation-in-part of U.S. patent application Ser. No. 16/160,399, filed Oct. 15, 2018, the contents of each of which being incorporated herein by reference in their entirety.

FIELD OF THE INVENTION

The present invention relates generally to weight training exercise, and more particularly, to adjustable weight exercise devices, systems, and methods.

BACKGROUND OF THE INVENTION

Conventionally, weight training exercises may be performed with free weight devices, such as dumbbells, kettlebells, or the like. These free weight devices may have a fixed weight, or may allow a user to adjust their weight through the manual addition or removal of weights.

Adjusting the weight on a free weight device may interfere with weight training by causing a substantial pause in or disruption to the user's desired training activity. Accordingly, improved devices, systems, and methods are desired for adjusting the weight of exercise equipment.

SUMMARY OF THE INVENTION

Aspects of the present invention are directed to physical fitness assessment systems and methods and wellness assessment systems and methods.

In accordance with one aspects of the present invention, a physical fitness assessment system includes an exercise device and a host computer. The exercise device includes an exercise device network communication interface for communication over a network, a movement tracker configured to track movement of the exercise device, an exercise device memory, an exercise device processor coupled to the exercise device network communication interface, the movement tracker, and the exercise device memory, and exercise device programming in the exercise device memory. Execution of the exercise device programming by the exercise device processor configures the at least one exercise device to perform functions to track, via the movement tracker, movement of the exercise device by a user; determine a current physical activity data of the user based on, at least, the tracked movement of the exercise device by the user; and transmit over the network, via the exercise device network communication interface, the current physical activity data of the user. The host computer includes an image display for presenting a physical fitness assessment image based on the current physical activity data of the user, an image display driver coupled to the image display to control the image display to present the physical fitness assessment image, a host computer user input device to receive from the user a physical fitness assessment selection to apply to the current physical activity data to generate the physical fitness assessment image, a host computer network communication interface for communication over the network, a host computer memory, a host computer processor coupled to the image display driver, the host computer user input device, and the host computer network communication interface, and host computer programming in the host computer memory. Execution of the host computer programming by the host computer processor configures the host computer to perform functions to receive over the network, via the host computer network communication interface, from the exercise device the current physical activity data of the user; receive, via the host computer user input device, the physical fitness assessment selection to apply to the current physical activity data; compare the current physical activity data of the user against benchmark physical activity data correlated with the exercise device; based on the comparison, determine a physical fitness assessment of the user; generate the physical fitness assessment image based on the physical fitness assessment of the user; and present, via the image display, the physical fitness assessment image.

In accordance with another aspect of the present invention, a method of providing a physical fitness assessment to a user includes receiving tracked current physical activity data of the user, from an exercise device, via a host computer communication interface; receiving, via a host computer user input device, a physical fitness assessment selection; obtaining a physical fitness assessment of the user based on a determined relationship of the current physical activity data relative to benchmark physical activity data correlated with the exercise device as indicated by the received physical fitness assessment selection; and presenting the physical fitness assessment to the user via a host computer user interface.

In accordance with yet another aspect of the present invention, a wellness assessment system includes at least one exercise device. The at least one exercise device has a use detector configured to gather usage data responsive to manipulation of the exercise device by a user, a storage device coupled to the use detector, the storage device configured to store the gathered usage data, a processor coupled to the at least one exercise device, and a memory accessible to the processor, wherein the memory stores programming for execution by the processor. Execution of the programming by the processor performs functions, including functions to retrieve the gathered usage data from the storage device, generate an assessment of the wellness of the user by comparing the retrieved usage data to previously received usage data from one or more of the at least one exercise device, and present the generated assessment to the user.

In accordance with still another aspect of the present invention, a system for assessing wellness of a user includes a plurality of devices and a processor. Each of the plurality of devices is configured to collect user data generated for the user and to transmit the user data, at least one of the plurality of devices being an exercise device and at least one of the plurality of devices being a measurement device. The processor is coupled for communication with the plurality of devices, and is configured to receive the user data from the plurality of devices, compare the received user data to prior user data, generate an assessment of the wellness of the user from the comparison of the received user data and the prior user data, and communicate the assessment to the user. The user data collected by the exercise device includes usage of the exercise device by the user. The user data collected by the measurement device includes a physical condition of the user.

BRIEF DESCRIPTION OF THE DRAWINGS

The invention is best understood from the following detailed description when read in connection with the accompanying drawings. When a plurality of similar elements are present, a single reference numeral may be assigned to the plurality of similar elements with a small letter designation referring to specific elements. When referring to the elements collectively or to a non-specific one or more of the elements, the small letter designation may be dropped. It is emphasized that, according to common practice, the various features of the drawings are not necessarily to scale. On the contrary, the dimensions of the various features may be arbitrarily expanded or reduced for clarity. Included in the drawings are the following figures:

FIGS. 4A-4C depict an exemplary shell of the exercise device of FIGS. 1A-1C.

FIGS. 5A and 58 depict an exemplary shaft of the exercise device of FIGS. 1A-1C.

FIGS. 6A, 6B, 7A, 78, 8A, 8B, 9A, 9B, 10A, and 10B depict exemplary weights of the exercise device of FIGS. 1A-1C.

FIGS. 14A-14E depict isometric, front, top, bottom, and left side elevation views, respectively, of another exemplary exercise device in accordance with aspects of the present invention, wherein the telescopic shafts are shown in an extended position.

FIG. 14F depicts a cross-sectional side view of the device of FIG. 14B taken along the lines 14F-14F.

FIG. 14G depicts a cross-sectional side view of the device of FIG. 14E taken along the lines 14G-14G.

FIGS. 15A and 15B are exploded views of the device of FIGS. 14A-14G.

FIGS. 16A-16G depict isometric, front, rear, left, right, top and bottom views, respectively, of a weight of the device of FIGS. 14A-14G.

FIG. 18A is a front elevation view of the exemplary exercise device of FIGS. 14A-14E with the telescopic shafts in a retracted position.

FIG. 18D depicts a cross-sectional side view of the device of FIG. 18A taken along the lines 18D-18D.

FIG. 18F depicts a cross-sectional side view of the device of FIG. 18B taken along the lines 18F-18F.

FIG. 19 is a high-level functional block diagram of an example of a physical fitness assessment system including an exercise device that includes a sensor (e.g., a movement tracker), a mobile device, and a server system connected via various networks.

DETAILED DESCRIPTION OF THE INVENTION

Figure 1A:
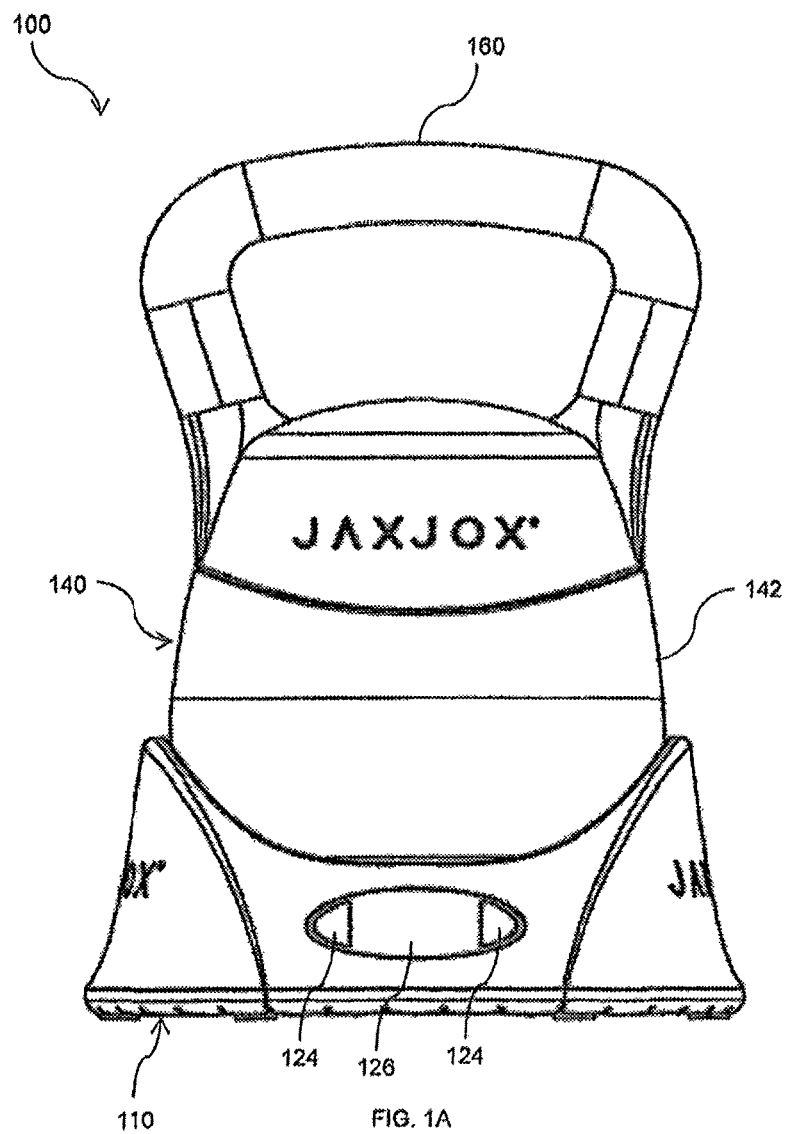
FIGS. 1A-IC depict an exemplary exercise device in accordance with aspects of the present invention.

Although the invention is illustrated and described herein with reference to specific embodiments, the invention is not intended to be limited to the details shown. Rather, various modifications may be made in the details within the scope and range of equivalents of the claims and without departing from the invention.

The exemplary exercise systems, methods, and devices disclosed herein are principally described with respect to kettlebells and dumbbells. However, it will be understood by one of ordinary skill in the art that the invention is not so limited. To the contrary, the disclosed concepts, features, and embodiments may be usable with any type of weight device without departing from the spirit or scope of the present invention, including, for example, barbells, medicine balls, or other free weights and weight systems.

The exemplary systems, devices, and methods disclosed herein may be usable by an individual user as part of one or a series of weight training exercises. In such uses, the disclosed embodiments may allow the individual user to select a desired weight for the weight training exercise, and/or adjust the weight of the exercise device before, during, or after a weight training exercise.

Additionally, the exemplary systems, devices, and methods disclosed herein may be usable by groups of users as part of a coordinated weight training exercise. Such groups of users may be co-located at a single location or remotely located and connected by technology in a virtual group. In such use, whether the users are co-located or in a virtual group, the disclosed embodiments may allow an individual user in the group to select a desired weight for the weight training exercise, and automatically communicate that desired weight to the exercise systems or devices of other individuals in the group. The desired weight may further be automatically selected at the exercise systems or devices of one or more of the individuals in the group.

Alternatively, the exemplary systems, devices, and methods disclosed herein may be usable by an individual user alone without connection to other systems or devices. Accordingly, the usage of the systems, devices, and methods is scalable.

Referring now to the drawings, FIGS. 1A-1C, 2A, and 2B illustrate an exemplary exercise device or apparatus 100 in accordance with aspects of the present invention. Exercise device 100 may be, for example, provided in the form of a kettlebell. As a general overview, device 100 includes a base assembly 110, a shell assembly 140, and a plurality of weights 170. Additional details of device 100 are described below.

Base assembly 110 provides support for the components of device 100. Base assembly 110 has a housing 112 which houses certain components of device 100. Housing 112 may include one or more exterior surfaces on which other components of device 100 may rest.

As shown in FIGS. 2A, 2B, 3A and 3B, housing 112 of base assembly 110 may include a first surface 114 and a second surface 116 on an upper portion thereof. Surfaces 114 and 116 form a base configured to support shell assembly 140 and weights 170. In particular, surface 114 may be configured to support weights 170, e.g., in a stacked orientation, and surface 116 may be configured to support shell assembly 149, e.g., at a lower surface thereof. In this example, surface 116 surrounds first surface 114. Surface 116 may be formed at a same level as surface 114, or may be provided at a level above or below the level of surface 114.

Base assembly 110 may further include one or more guide walls 118 and guide projections 119. Guide walls 118 extend upward from surface 116 to assist the user of device 100 in aligning shell assembly 140 on base assembly 110. Guide projections 119 extend upward from surface 114 to assist the user of device 100 in aligning weights 170 on base assembly 110.

Base assembly 110 houses a driver 120. Driver 120 is configured to be coupled to and decoupled from a shaft 150 of shell assembly 140, as will be described in greater detail below. Driver 120 is further configured to move, e.g. rotate, the shaft 150 of shell assembly 140. In an exemplary embodiment, driver 120 comprises a motor, such as a brushless electric motor. Suitable motors for use as driver 120 will be known from the description herein.

Base assembly 11Q may further comprise a controller 122. Controller 122 electrically controls driver 120 to operate, e.g., to rotate, shaft 150 when shaft 150 is coupled to driver 120. As will be discussed in greater detail below, controller 122 may operate driver 120 automatically, or in response to some input, e.g., input from a user of exercise device 100 or a transmission from another exercise device 100.

Controller 122 may be in communication with a sensor 123. Sensor 123 is configured to detect when driver 120 is coupled to or decoupled from shaft 150 of shell assembly 140. Controller 122 may thus operate driver 120 only when sensor 123 signals that driver 120 is coupled to shaft 150 or that one or more surfaces of the base assembly 110, such as surfaces 114 and/or 116, support or are adjacent to the shell assembly 140 and/or weights 170. Suitable sensors for use as sensor 123 include, for example, optical sensors, pressure sensors, or electrical sensors.

Base assembly 110 may further comprise an input device 124. Input device 124 receives input from a user of exercise device 100. Input device 124 is electrically and/or mechanically coupled to driver 120 to cause driver 120 to rotate shaft 150 based on input by the user of exercise device 100. The input may comprise a selection of a type of weight training exercise, an amount of weight, or a number of weights 170. Controller 122 may then control driver 120 based on the type of weight training exercise, an amount of weight, or a number of weights 170 received by input device 124.

The form of input device 124 is not intended to be limited. Input device 124 may be configured to receive a mechanical input, e.g., a knob, dial, button, slider, or other structure, adapted to be directly manipulated or moved by the user of exercise device 100. Input device 124 may be configured to receive an electrical or electronic input, e.g., a key, touchscreen, or touchpad, or other structure, adapted to generate a mechanical signal in response to a user interaction. Other structures suitable for use as input device 124 will be known from the description herein.

Along with input device 124, base assembly 110 may further comprise a display 126. Display 126 is configured to display the input provided by the user to input device 124, e.g., the selected exercise, amount of weight, or selected number of weights 170. Suitable displays for use as display 126 include, for example, liquid crystal displays or light emitting diode displays. Other displays will be known from the description herein.

Base assembly 110 may further comprise a communication device 128. Communication device 128 may be configured to wirelessly communicate with another exercise device 100, and/or with other wireless transceivers, as discussed in greater detail below. Data received via communication device 128 may be used to control the operation of driver 120, as described in greater detail below.

While input device 124 and display 126 are described as being associated with and/or housed by base assembly 110, it will be understood that the invention is not so limited. For example, sensor 123, input device 124, and/or display 126 may be provided on shell assembly 140. In one embodiment, sensor 123, input device 124, and display 126 are provided on an exterior surface of shell 142. In this embodiment, sensor 123 and/or input device 124 may communicate the user input to the driver 120 in base assembly 110 by wireless communication, or by way of a wired communication interface which is created when shell assembly 140 is placed on base assembly 110. Where sensor 123 is provided on the exterior surface of shell 142, sensor 123 may be provided with a sensor cover 129 to protect sensor 123 from an external environment.

Alternatively, device 100 may not include a display 126. In such embodiments, the information to be presented by display 126 may be presented with a remote device (e.g., on a smartphone or tablet display or monitor of the user) which is in wired or wireless communication with device 100.

A power supply 130 (such as a rechargeable battery) may be provided in base assembly 110 or shell assembly 140 for powering the electrical components of device 100. Alternatively, device 100 may be provided with power through one or more power/communication terminals 132 formed on base assembly 110 or via a port or cable connection. Device 100 may be configured to be primarily powered through terminals 132, or may use power connections through terminals 132 for recharging power supply, e.g., when power supply 130 is a rechargeable battery. Other sources of power can optionally be selected as well.

Figure 1B:
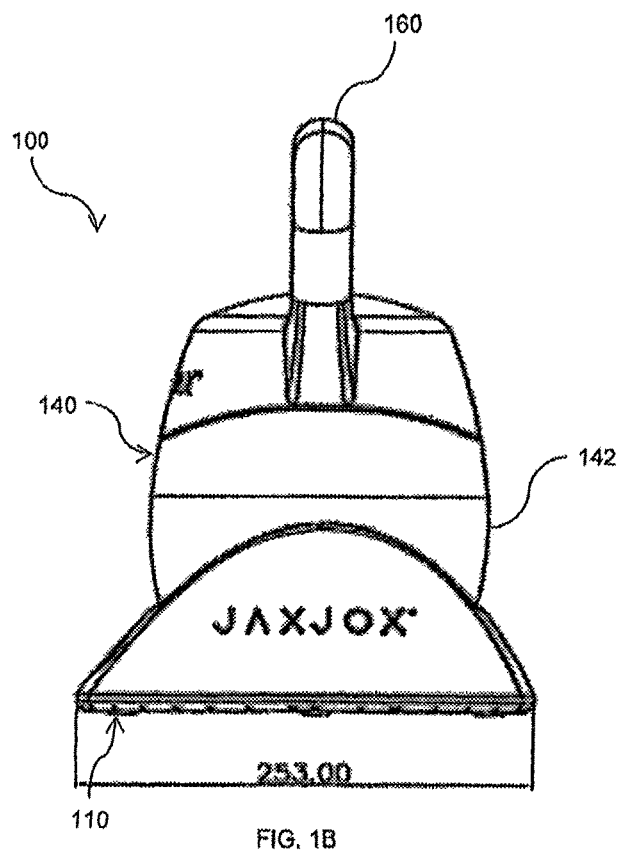
Figure 1C:
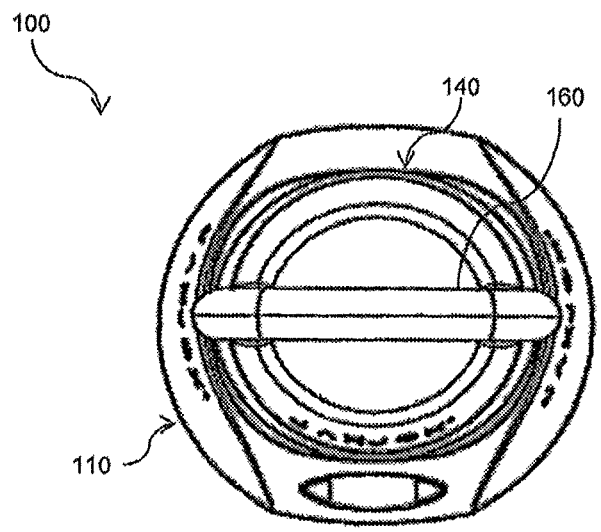

Shell assembly 140 is grasped and lifted by a user of device 100. As shown in FIGS. 1A-1C, shell assembly 140 may have the shape of a kettlebell. However, it will be understood that the shape of shell assembly 140 is not limited, and shell assembly 140 may be configured as any type of free weight device.

Figure 2A:
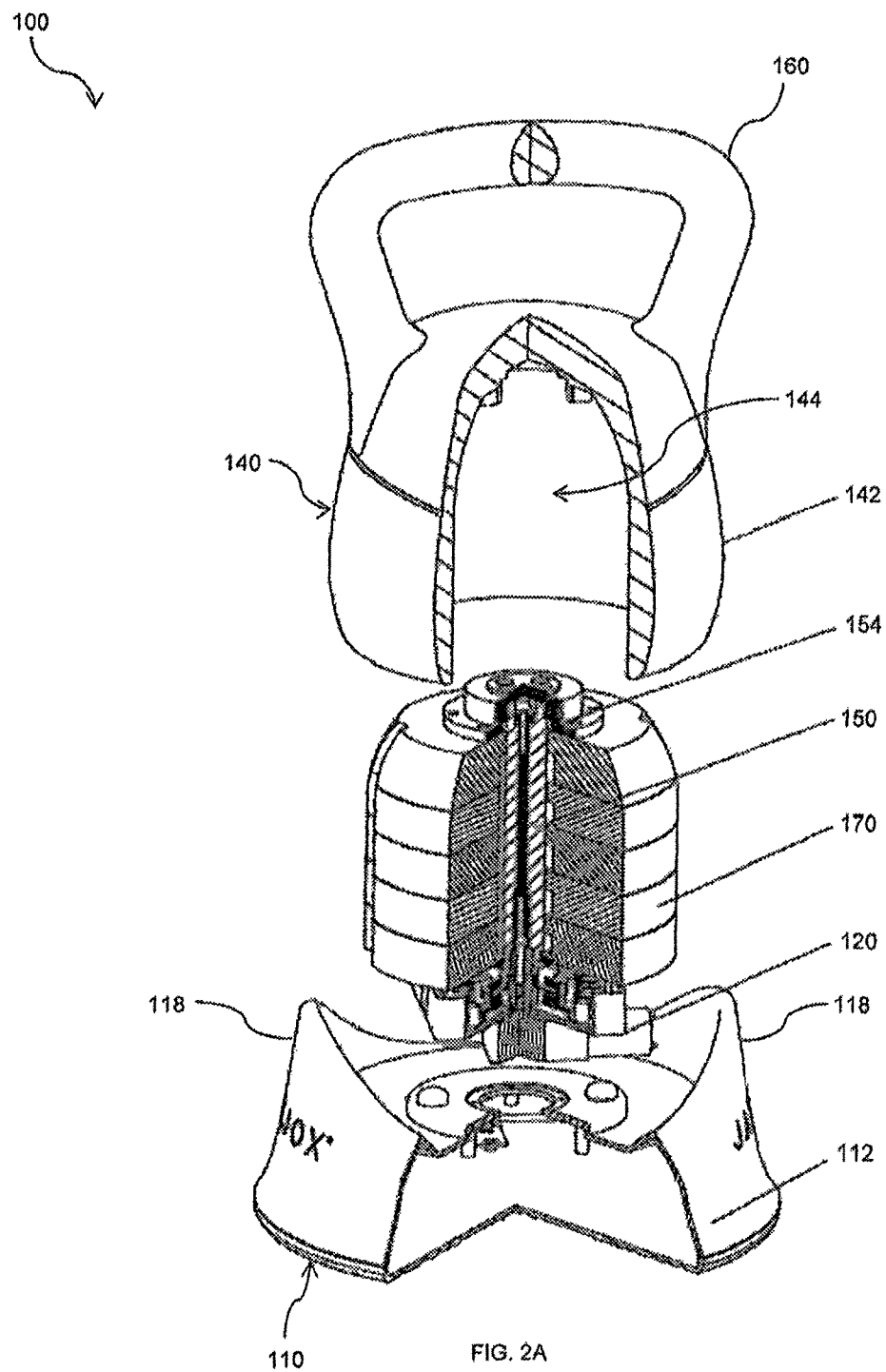
FIGS. 2A and 2B depict exploded views of the exercise device of FIGS. 1A-1C.

As shown in FIGS. 2A, 2B, and 4A-4C, shell assembly 140 includes a shell 142. Shell 142 defines an interior space 144, which is sized to receive weights 170. Shell 142 and interior space 144 have a shape and size selected to correspond to the shape and size of weights 170. For example, shell 142 and interior space 144 may have a generally circular cross-section, as shown in FIG. 2A, or any other shape to match that of a shell or support that may not have a circular cross-section. Interior space 144 of shell 142 may further include one or more ridges 146. Ridges 146 may be used to align weights 170 in space 144, and may be used to prevent rotation of weight 170 within space 144.

Shell assembly 140 further includes shaft 150. Shaft 150 extends within the interior space 144 of shell 142. Shaft 150 may be coupled for rotation relative to the other components of shell assembly, such as shell 142. As will be described in greater detail below, rotation of shaft 150 when weights 170 are received within interior space 144 may couple shaft 150 with one or more of weight 170.

Shaft 150 is configured to be coupled to driver 120 when shell assembly 140 is supported on base assembly 110. Shaft 150 is also configured to be decoupled from driver 120 when shell assembly 140 is removed from base assembly 110, e.g., when a user lifts shell assembly 140 off of base assembly 110 during a weight training exercise. Shaft 150 includes projections 152 for engaging with corresponding structures on weights 170, as described in greater detail below.

Figure 2B:
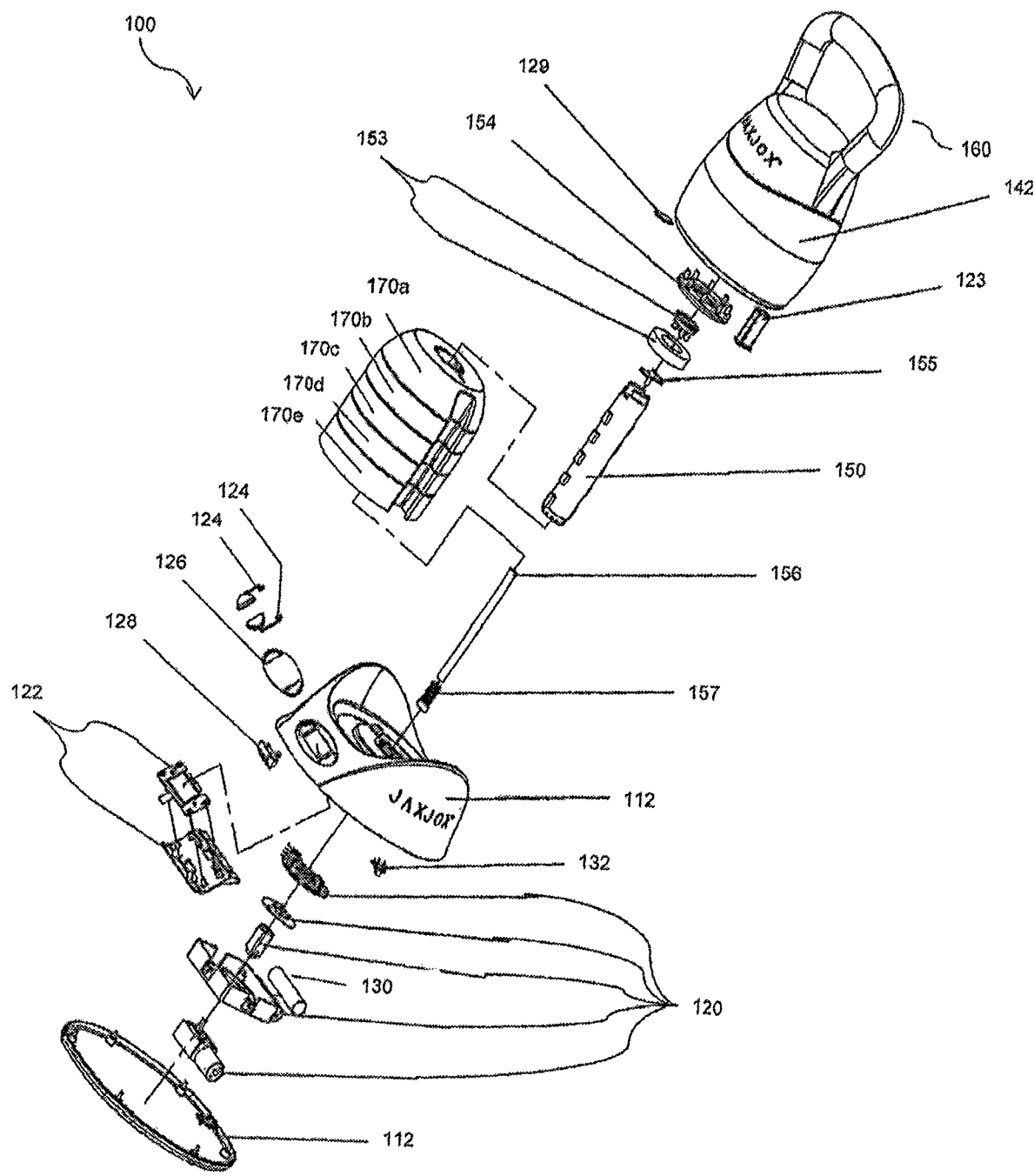
Figure 3A:
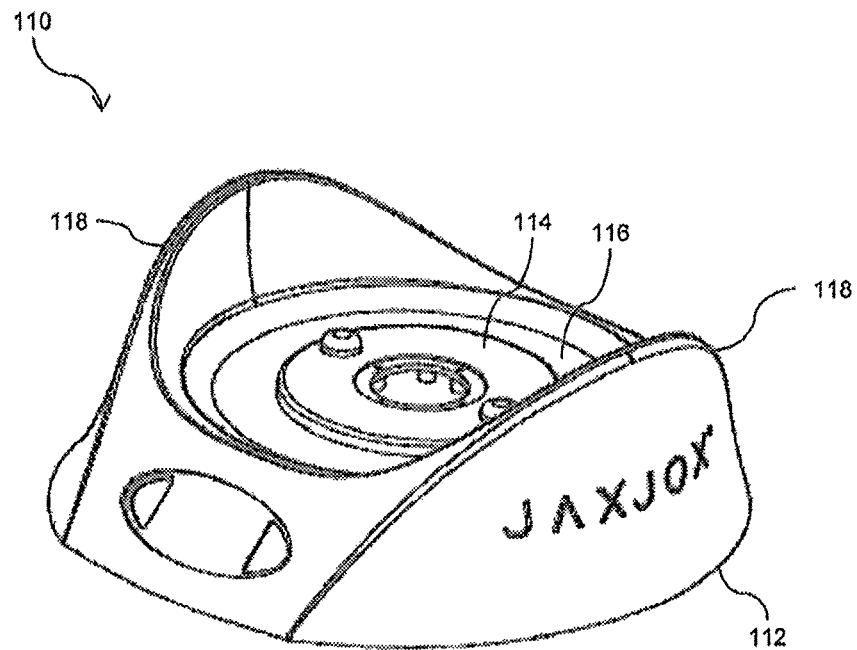
FIGS. 3A and 3B depict an exemplary base assembly of the exercise device of FIGS. 1A-1C.
Figure 3B:
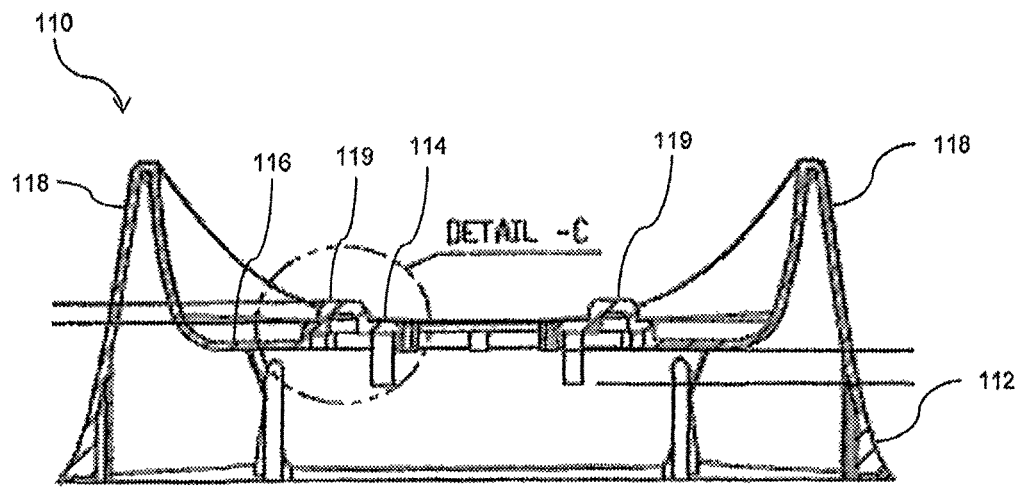
Figure 5A:
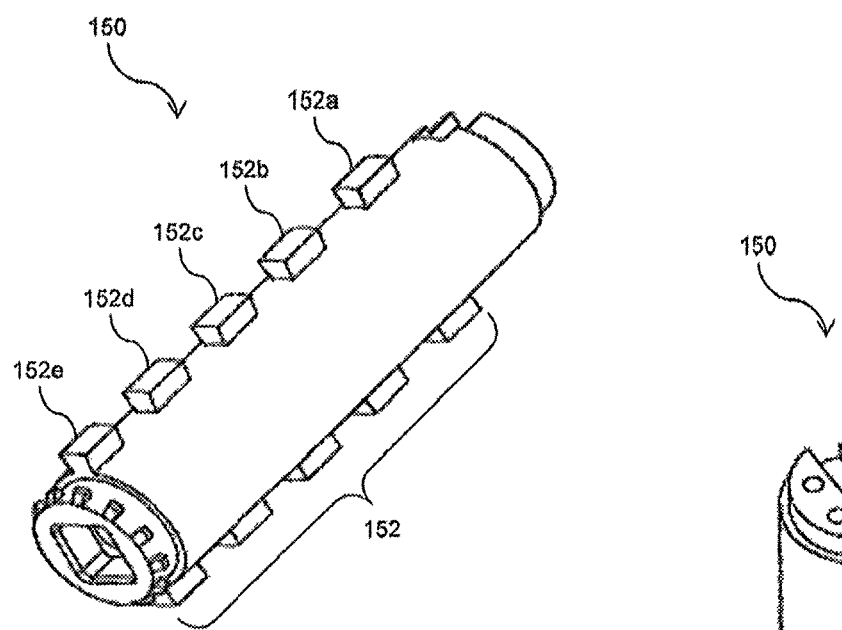
Figure 5B:
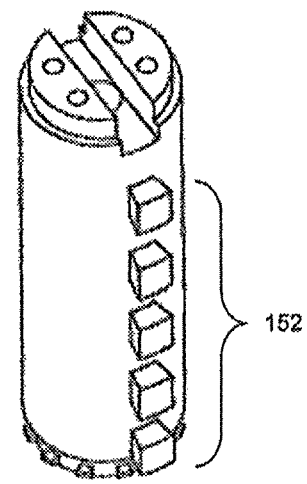

At the upper end of shaft 150, shell assembly 140 may further include one or more bearings 153 to enable rotation of shaft 150 relative to shell 142. Bearings 153 are coupled to shell assembly 150 by an upper fixed plate 154, and are coupled to shaft 150 by a fixed positional plate, as shown in FIG. 2B. At the lower end of shaft 150, shaft 150 is configured to be coupled to driver 120 by way of a linkage including a connecting rod 156 and a fixed block 157 having a spring, as shown in FIG. 2B.

Shell assembly 140 may further comprise a handle 160 positioned to be grasped by the user during the weight training exercise. As shown in FIGS. 2A, 2B, and 4A-4C, handle 160 is coupled to the exterior of shell 142. Handle 160 is provided at the apex of shell assembly 140, at a location of shell 142 opposite the coupling of shaft 150 to shell 142. Handle 160 is oriented orthogonally relative to shaft 150. However, it will be understood that, based on the type of weight training which is desired to be performed with exercise device 100, handle 160 may have a different orientation or an adjustable orientation, e.g. a parallel or oblique orientation, relative to shaft 150.

Weights 170 are selectively coupled to shell assembly 140 to enable performance of adjustable weight training exercises. As shown in FIGS. 2A and 2B, weights 170 are configured to be positioned adjacent one another, e.g., in a stacked orientation. In this orientation, all weights 170 are capable of fitting in the interior space 144 of shell 142. Thus, shell 142 is capable of being positioned overtop weights 170, and a lower edge 148 of shell 142 may rest on a surface 116 of base assembly 110.

As shown in FIGS. 6A-10B, device 100 may include five weight 170a, 170b, 170c, 170d, and 170e. It will be understood, however, that the number of weights shown in the drawings is provided for the purpose of illustration, and is not intended to be limiting. Any number of weights may be provided based on the desired amount, degree, or level of adjustability of exercise device 100. For a non-limiting example, 2, 3, 4, 5, 6, 7, 8 or more weights 170 may be provided in device 100, and weights 170 may be provided in increments of 1, 2, 3, 4, 5, 10, or 20 pounds.

Each weight 170 has a respective opening 172. Where weights 170 have a circular cross-section, opening 172 may be provided at a center or central region of each weight. When weights 170 are positioned in a stacked orientation, openings 172 are aligned or overlap with one another, such that openings 172 define an aperture extending along an axis of the stacked weight 170 from the uppermost weight 170a to the lowermost weight 170e.

Figure 6A:
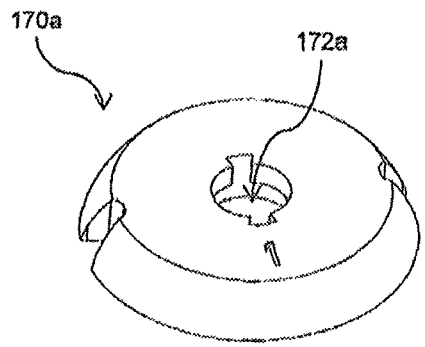
Figure 6B:
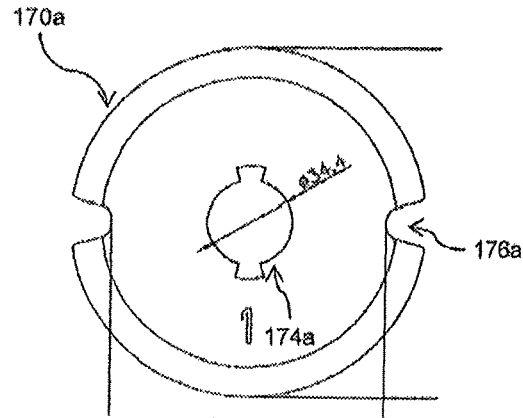
Figure 7A:
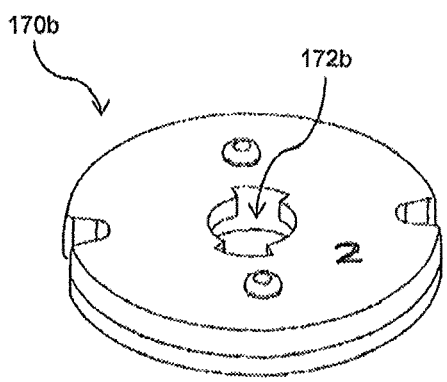
Figure 7B:
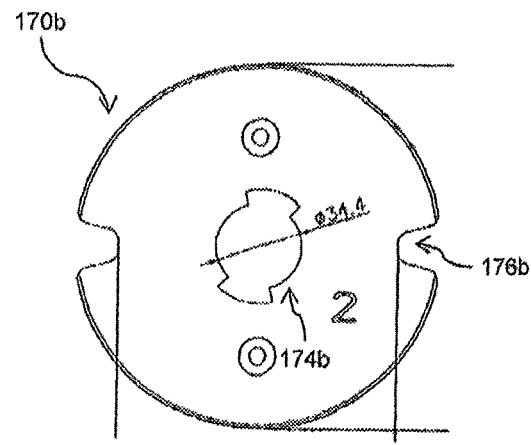
Figure 8A:
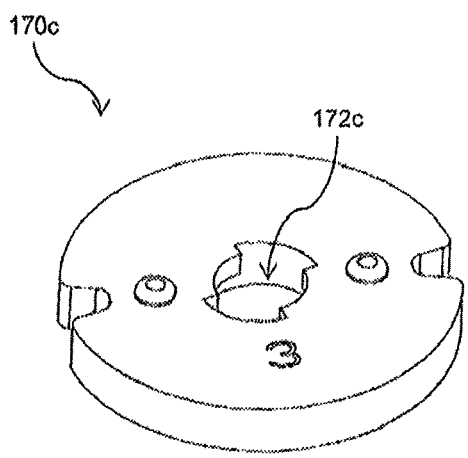
Figure 8B:
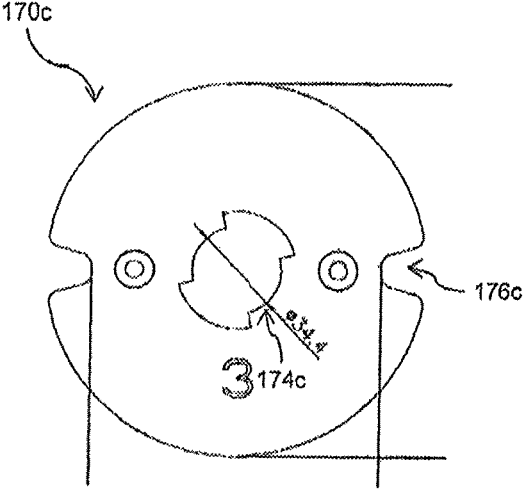
Figure 9A:
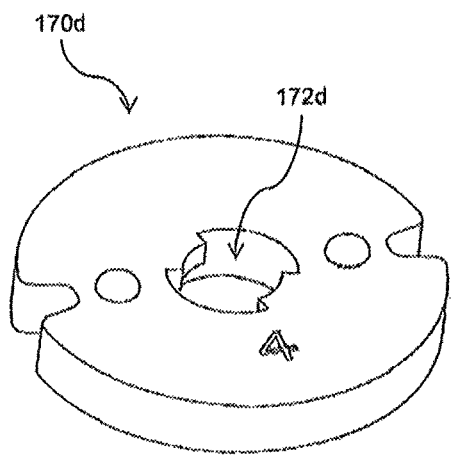
Figure 9B:
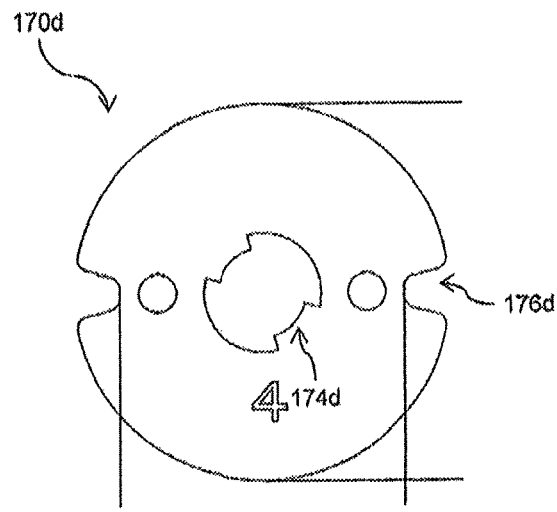
Figure 10A:
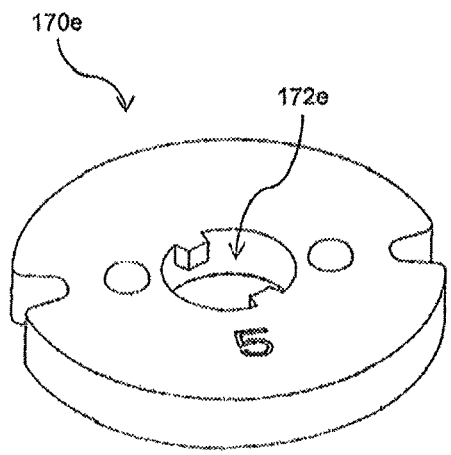
Figure 10B:
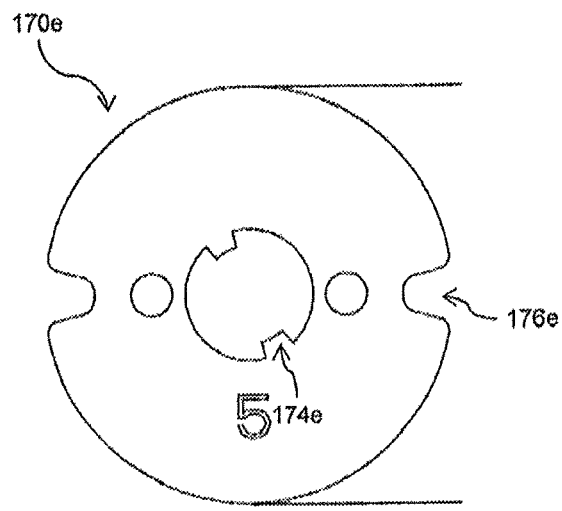

Each weight 170 has one or more ledges 174 extending into its respective opening. The circumferential width of a particular ledge 174 is dependent on where the respective weight is positioned in the stack of weights 170; the higher the weight 170 in the stack, the wider the ledge 174. As shown in FIG. 6A, ledge 174a has the largest width (covering nearly half of opening 172a), and ledge 174e has the smallest width (covering very little of opening 172e).

Each weight 170 may have one or more slots 176 on a periphery thereof. When weights 170 are positioned in a stacked orientation, slots 176 are aligned or overlap with one another, such that they may together slide along ridges 146 on the interior of shell 142.

An exemplary operation of exercise device 100 is described below in accordance with aspects of the present invention and with general reference to the embodiments of exercise device 100 illustrated in the figures.

Before the weight training exercise, weights 170 are provided in a stacked orientation on surface 114 of base assembly 110. In this position, the aperture defined by openings 172 extends from the upper surface of the uppermost weight 170a down through the remaining weight 170 to the region of driver 120.

Prior to performing a weight training exercise, the user places shell assembly 140 overtop the stacked weights 170. Alternatively, shell assembly 140 may already be positioned overtop weight 170, with the lower surface 148 of shell 142 supported on surface 116 of base assembly 110. In this position, shaft 150 extends through the aperture formed by openings 172, and can physically couple with driver 120.

When the user is ready to begin the exercise, the user may provide the appropriate input via input device 124. The input may comprise a selection of a type of weight training exercise, an amount of weight, or a number of weights 170. Responsive to receiving this input, driver 120 automatically moves shaft 150 to engage with a number of weights 170 corresponding to the user's input Where base assembly 110 includes a controller 122, controller 122 controls driver 120 to rotate shaft to selectively couple shaft 150 with the appropriate number of weights 170. Controller 122 may be programmed to determine, or may have predetermined, the appropriate number of weights 170 corresponding to the user input, e.g. the type of weight training exercise or the amount of weight selected by the user. Where the user selects a number of weights, controller 122 may control driver 120 to rotate shaft 150 to couple with the selected number of weights 170.

Alternatively or in addition to input device 124, driver 120 may operate in response to the receipt of a communication by communication device 128. The user of exercise device 100 may wirelessly transmit a selection of a type of weight training exercise, an amount of weight, or a number of weights 170 to communication device 128 device 100, e.g., using the user's smartphone. Upon receipt of this data, controller 122 electrically controls driver 120 to rotate shaft 150 based on the data received from communication device 128.

Rotation of shaft 150 by driver 120 causes one or more of the projections 152 to selectively engage with corresponding ledges 174 on weight 170. The number of ledges 174 which are engaged by projection 152 is dependent on the rotational position of shaft 150. As such, driver 120 may control the number of weights 170 which are engaged with shaft 150 by controlling the rotational position of shaft 150. An example of such positioning is described below.

In a first rotational position of shaft 150, none of projections 152 underlie any of ledges 174. In this position, shaft 150 is freely movable through openings 172, e.g., to allow lifting of shell assembly 140 without any associated weights 170.

In a second rotational position of shaft 150, an uppermost projection 152a underlies ledge 174a of weight 170a, while the remaining projections 152 do not underlie any other ledges 174. In this position, shaft 150 engages with weight 170a, i.e., prevents axial movement of weight 170a relative to shaft 150, to allow lifting shell assembly 140 with weight 170a associated therewith.

In a third rotational position of shaft 150, an uppermost projection 152a underlies ledge 174a of weight 170a, and a next projection 152b underlies ledge 174b of weight 170b, while the remaining projections 152 do not underlie any other ledges 174. In this position, shaft 150 engages with weights 170a and 170b, i.e., prevents axial movement of weights 170a and 170b relative to shaft 150, to allow lifting shell assembly 140 with weights 170a and 170b associated therewith.

It will be understood that shaft 150 may be rotated into fourth, fifth, and sixth rotational positions, etc., to add engagement with weights 170c, 170d, and 170e in a similar fashion to that described above. Likewise, it will be understood that shaft 150 may be rotated to any number of rotational positions depending on the total number of weights 170 which are available to be engaged with shaft 150. For example, when exercise device 100 includes three total weights, shaft 150 may be rotatable to four different positions, whereas when exercise device 100 includes seven total weight, shaft 150 may be rotatable to eight different positions.

When shaft 150 is rotated to the correct rotational position, and the appropriate number of weights 170 are engaged with shaft 150, shaft 150 may be decoupled from driver 120 by lifting shell assembly 140 off of base assembly 110, e.g., by a user grasping handle 160 and lifting shell assembly 140. The user of exercise device 100 may then perform a desired weight training exercise with exercise device 100. Advantageously, decoupling shaft 150 from driver 120 removes the means for rotating shaft 150, and thereby prevents rotation of shaft 150, thereby preventing decoupling of the weights 170 from shaft 150 during the weight training exercise.

Figure 11:
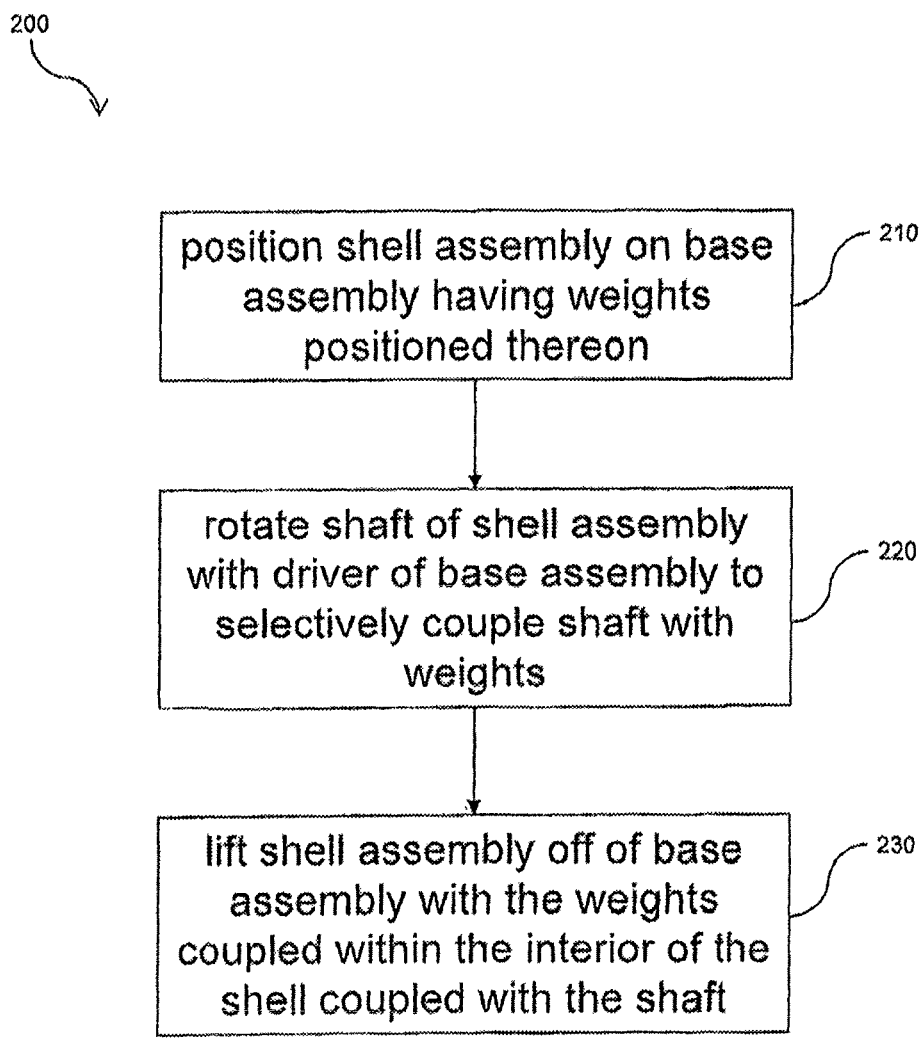
FIG. 11 depicts an exemplary exercise method in accordance with aspects of the present invention.

FIG. 11 illustrates an exemplary exercise method 200 in accordance with aspects of the present invention. As a general overview, method 200 includes positioning a shell assembly, rotating a shaft to selectively couple the shaft with one or more weight, and lifting the shell assembly. Additional details of method 200 are described below with respect to the component of device 100.

In step 210, a shell assembly is positioned on a base assembly having a plurality of weights positioned thereon. In an exemplary embodiment, shell assembly 140 is positioned on surface 116 of base assembly 110 overtop weights 170, such that weights 170 are received within interior space 144 of shell 142 of shell assembly 140. When shell assembly 140 is positioned overtop weights 170, shaft 150 is positioned within the defined by opening 172 in weights 170.

In step 220, a shaft of the shell assembly is rotated to selectively couple the shaft with one or more of the plurality of weights. In an exemplary embodiment, shaft 150 is rotated relative to shell 142 and weights 170. Shaft 150 is rotated by driver 120 of base assembly 110. Driver 120 rotates shaft 150 based on input provided by the individual performing the exercise to the input device 124, which is then communicated to controller 122. Rotation of shaft 150 by driver 120 causes shaft 150 to selectively engage with a desired number of weights 170, e.g., a number selected by an individual performing exercise method 200. In a further embodiment, this engagement include rotating shaft 150 to cause projections 152 on shaft 150 to engage with (e.g., underlie) respective ledges 174 of the desired number of weights 170, to prevent movement of the desired number of weights 170 along the axis of shaft 150.

In step 230, the shell assembly is lifted. In an exemplary embodiment, shell assembly 140 is lifted off of base assembly 110 by the individual performing exercise method 200. The individual may lift shell assembly 140 by grasping handle 160 of shell assembly 140. Shell assembly 140 is lifted with the weights 170 which are coupled with shaft 150 being held in the interior space 144 of shell 142. Engagement between projections 152 on shaft 150 and ledges 174 on weight 170 prevents decoupling of the weight 170 from shaft 150 when shell assembly 140 is lifted off of base assembly 110.

Figure 12:
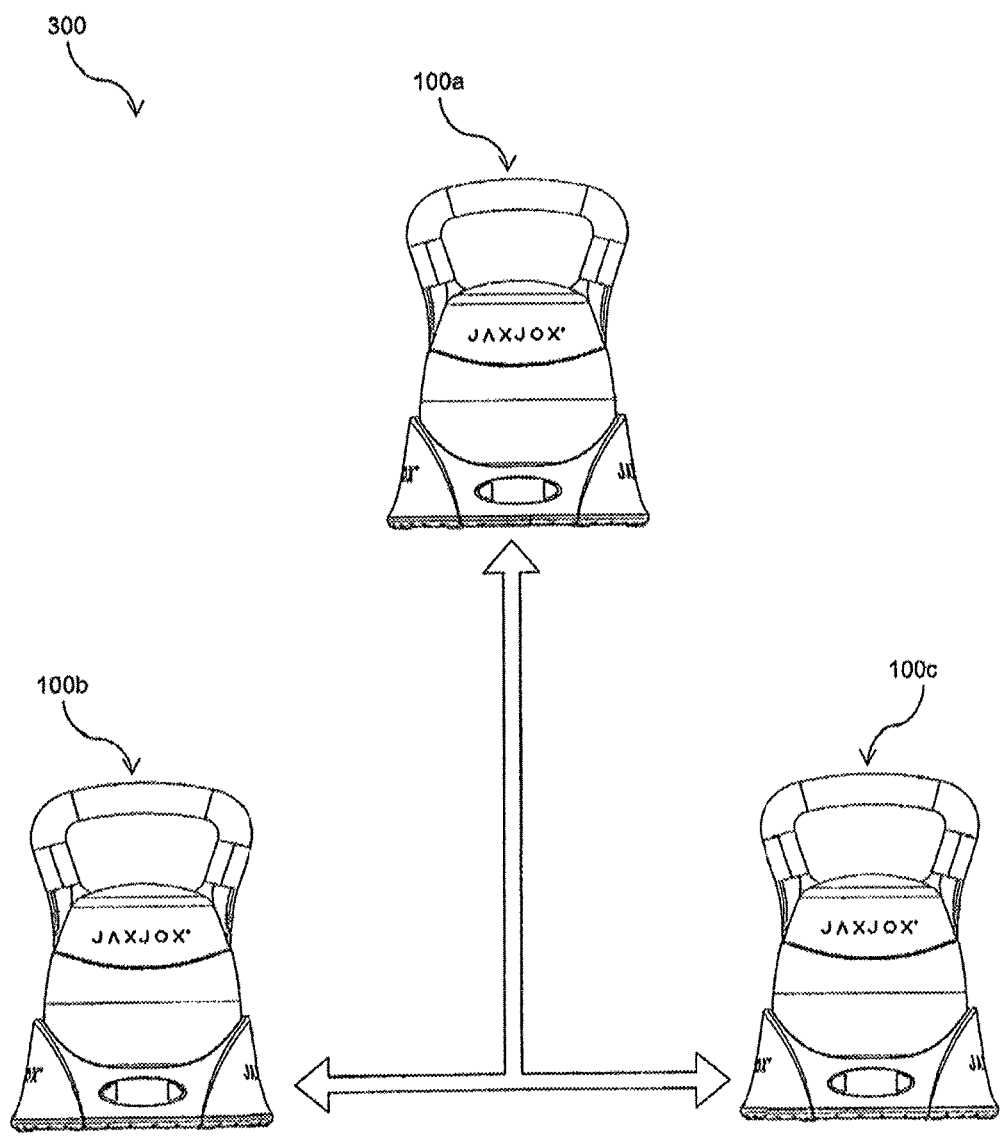
FIG. 12 depicts an exemplary exercise system in accordance with aspects of the present invention.

FIG. 12 illustrates an exemplary exercise system 300 in accordance with aspects of the present invention. As a general overview, system 300 includes a plurality of exercise devices 100. Additional details of system 300 are described below with reference to the components of exercise device 100.

As set forth above, exercise device 100 comprises a base assembly 110. In system 300, each exercise device 100 may comprise a respective base assembly 110. Alternatively, system 300 may comprise one or more combined base assemblies configured to support multiple shell assemblies and weight stacks. Such a combined base assembly may comprise subcomponents (e.g., input devices, displays, and communication devices) for each shell assembly supported by the combined base assembly, or may include a single subcomponent which is associated with each of the shell assemblies and weight stacks supported by the combined base assembly.

The driver 120 of each base assembly 110 of the exercise devices 100 (or the driver 120 of the combined base assembly) are configured to rotate respective shafts 150 based on data received via the associated communication device 128. In an exemplary embodiment, one of the exercise devices 100a (e.g., a master exercise device) receives an input from a user (e.g., via an input device 124) comprising a selection of a number of weight 170. The communication device 128 associated with the master exercise device 100a then transmits the input from the user to the communication device(s) 128 of one or more of the other exercise devices 100b, 100c in system 300 (as indicated by arrow in FIG. 12). These other exercise devices 100b and 100c are configured to receive data from the communication device 128 of the master exercise device 100a, and operate driver 120 to rotate shaft 150 to engage the appropriate number of weights 170. In this manner, one user of exercise system 300 (e.g., a weight trainer) may control the weight selection for each of the other users of exercise system (e.g., students).

Figure 13:
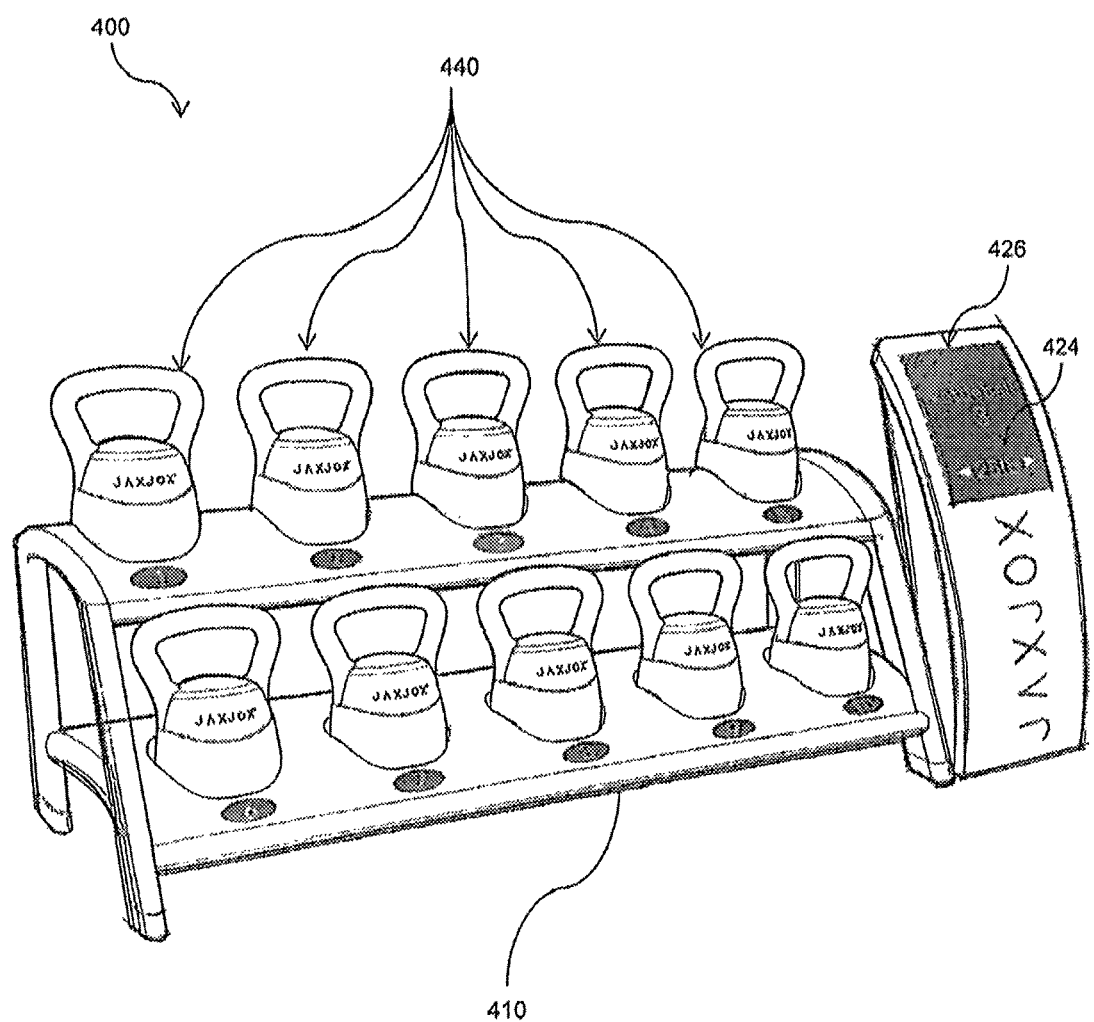
FIG. 13 depicts another exemplary exercise system in accordance with aspects of the present invention.

FIG. 13 illustrates another exemplary exercise system, exercise system 400, in accordance with aspects of the present invention. Generally, this invention also provides an exercise system comprising a plurality of exercise devices each having a plurality of weights configured to be positioned adjacent one another, each of the exercise devices being configured to engage a selected number of the plurality of weights. The exercise system also comprises at least one base assembly having a base configured to support the plurality of weights of at least one of the exercise devices, the base assembly being configured to be coupled to and decoupled from at least one of the exercise devices. The exercise system optionally includes an interface configured to communicate with one or more of the plurality of exercise devices. The base assembly is optionally configured to cooperate with one or more of the exercise devices, such as to increase or decrease the number of the weights engaged by one or more of the exercise devices, based on information received from or communicated to the interface.

As a general overview, system 400 includes a base assembly 410 and a plurality of shell assemblies 440. Base assembly 410 and shell assemblies 440 may include any of the components described above with respect to exercise device 100. Additional details of system 400 are described below.

Base assembly 410 provides support for the components of system 400, including each of the shell assemblies 440. Base assembly 410 is a combined base assembly, which may comprise subcomponents (e.g., drivers, input devices, controllers, communication devices, etc.) associated with each shell assembly 440 or groups of shell assemblies 440 supported by the combined base assembly, or may include a single subcomponent which is associated with each or all of the shell assemblies 440 and weight stacks supported by the combined base assembly 410.

Base assembly 410 houses a driver for each of the shell assemblies 440 supported on base assembly 410. Each driver is configured to be coupled to and decoupled from a respective shaft of each shell assembly 440, as described above with respect to exercise device 100.

Base assembly 410 may further comprise one or more controllers. Base assembly 410 may comprise a plurality of controllers, e.g., one controller for each driver or for each group of drivers, or may comprise a single master controller which electrically controls all drivers.

System 400 may further comprise a user interface such as an input device 424. Input device 424 receives input from a user of exercise system 400. Input device 424 may be operable to select a number of weights for any of the shell assemblies 440 of system 400, as described above with respect to exercise device 100. Input device 424 may enable the same weight to be input for all shell assemblies 440, or may allow the weight of each shell assembly 440 to be individually set.

The form of input device 424 is not intended to be limited. As shown in FIG. 13, input device 424 may be formed separately from base assembly 410, and communicate with the controller(s) In base assembly 410 by wire or wirelessly. Alternatively, input device 424 may be integrated into one structure with base assembly 410. A single input device 424 may be provided for all shell assemblies 440, or an input device 424 may be provided for each shell assembly 440. Structures for use as input device 424 will be known from the description herein.

As shown in FIG. 13, input device 424 may be integrated with a display 426. Display 426 is configured to display the input provided by the user to input device 424, e.g., the selected exercise, amount of weight, or a selected number of weights. As with input device 424, a single display 426 may be provided for all shell assemblies 440, or a display 426 may be provided for each shell assembly 440 or groups or subgroups of shell assemblies 440. Suitable displays for use as display 426 will be known from the description herein.

Shell assemblies 440 are grasped and lifted by users of system 400. Each shell assembly 440 includes a shaft which may be selectively coupled with one or more weights housed in the interior of respective shell assemblies 440, as described above with respect to exercise device 100.

Accordingly, a multi-stand embodiment such as the exercise system illustrated in FIG. 13 has the ability to display multiple exercise devices, such as kettlebells for example, on one stand and will either have one main display that controls all of the exercise devices or multiple displays with each display controlling an adjacent exercise device. The weight of each exercise device can either be the same or different weight per each device. For example, and for purposes of illustration, the top half of the exercise devices (on the top rack illustrated in FIG. 13) could each hold a maximum of 42 lbs, and the bottom half could have a maximum weight of 90 lbs. Other weights and combinations of weight variations are also contemplated.

The exercise devices and systems according to this invention are optionally provided with a wide range of ornamental shapes and designs and contours, depending on factors such as consumer preferences, aesthetic considerations, source identification, etc. Various ornamental designs can therefore be selected independent of the functionality described herein. For example, and for purposes of illustration, exemplary ornamental features of the exercise device are shown in co-pending U.S. Design patent application Ser. No. 29/635,801, filed Feb. 2, 2018, the disclosure of which is incorporated herein by reference.

FIGS. 14A-14G, 15 and 18A-18F illustrate an exemplary exercise device or apparatus 500 in accordance with aspects of the present invention. Exercise device 500 may be, for example, provided in the form of a dumbbell. Exercise device 500 may alternatively be a barbell.

As a general overview, device 500 includes a base assembly 510, a shell assembly 540, and a plurality of weights 570. Additional details of device 500 are described below.

Referring generally to FIGS. 14A-14G and 15, an exercise device 500 includes a plurality of weights 570 configured to be positioned adjacent one another; a shell assembly 540 having a shell including a handle shaft 542 defining an interior, the shell assembly 540 also having a shaft 544 coupled for movement relative to the shell and extending within the interior of the shell, wherein movement of the shaft 544 relative to the shell selectively couples the shaft 544 with one or more of the plurality of weights 570; and a base assembly 510 having a base including a housing 512 configured to support the plurality of weights 570 and the shell assembly 540, the base assembly 510 also having a driver including a motor 523 configured to be coupled to the shaft 544 of the shell assembly 540 when the shell assembly 540 is supported by the base including a housing 512, the driver 523 also being configured to be decoupled from the shaft 544 of the shell assembly 540 when the shell assembly 540 is not supported by the base including a housing 512; wherein the driver 523 of the base assembly 510 is configured to move the shaft 544 of the shell assembly 540 relative to the shell of the shell assembly 540 when the driver 523 is coupled to the shaft 544 of the shell assembly 540 to selectively couple the shaft 544 with the one or more of the plurality of weights 570.

The plurality of weights 570 are arranged in plural groups, each of the plural groups positioned on opposite sides of the shell assembly, and wherein the shell assembly 540 has plural shafts 544, each of the plural shafts being coupled for movement relative to the shell and extending within the interior of the shell, wherein movement of the shafts 544 relative to the shell selectively couples the shafts 544 with one or more weights 570 in each of the groups of weights 570.

Each of the plurality of weights 570 has an opening 582, the openings 582 of the plurality of weights 570 at least in part defining an aperture 582' extending along an axis 'B' when the plurality of weights 570 are adjacent one another.

The shaft 544 of the shell assembly 540 is positionable within the aperture 582' defined by the plurality of weights. Each of the plurality of weights 582 includes one or more engagement surfaces 580/590. Movement of the shaft 544 relative to the shell by the driver 523 causes the shaft 544 to selectively engage with one or more of the plurality of weights 570 to limit or prevent movement of the one or more of the plurality of weights 570 along a direction orthogonal to the axis B of the aperture 582.

The shell assembly 540 further comprises a handle portion 542 positioned to be grasped by a user of the exercise device 500. The driver 523 comprises a motor 523, and the base assembly 510 further comprises a controller that electrically controls the motor 523 to move the shaft 544 based on an input from a user of the exercise device.

The base assembly 510 further comprises an input device 521 which is electrically or mechanically coupled to the driver 523 to cause the driver to rotate the shaft 544 based on input from a user of the exercise device 500.

Decoupling of the shaft 544 of the shell assembly 540 from the driver 523 of the base assembly prevents movement of the shaft 544 relative to the shell, thereby preventing decoupling of the one or more of the plurality of weights 570 from the shaft 544 of the exercise device 500.

An exercise method is also provided, including positioning a shell assembly 540 on a base assembly 510 having a plurality of weights 570 positioned thereon; moving a shaft 544 of the shell assembly 540 relative to the shell with a driver 523 of the base assembly 510 coupled to the shaft 544 to selectively couple the shaft 544 with one or more of the plurality of weights 570; and lifting the shell assembly 540 off of the base assembly 510 with the one or more of the plurality of weights 570 coupled with the shaft 544 of the shell assembly 510.

Each of the plurality of weights 570 has an opening 582, the openings 582 of the plurality of weights 570 at least in part defining an aperture 582' extending along an axis B, and wherein the positioning step comprises positioning the shaft 544 of the shell assembly 540 within the aperture 582' defined by the plurality of weights 570. Each of the plurality of weights 570 includes one or more engagement surfaces 580/590, and wherein the moving step comprises moving the shaft 544 relative to the shell to cause the shaft 544 to selectively engage with the engagement surface 580/590 of respective ones of the plurality of weights 570 to prevent movement of the one or more of the plurality of weights 570 in a direction orthogonal to the axis B of the aperture 582'. The shell assembly 540 further comprises a handle portion 542, and wherein the lifting step comprises grasping the handle portion of the shell assembly 540. The driver 523 comprises a motor 523, and the base assembly 510 further comprises a controller that electrically controls the motor 523, and wherein the moving step comprises providing input to the controller to control the motor 523 to move the shaft 544. The base assembly 510 further comprises an input device 521 which is electrically or mechanically coupled to the driver 523, and wherein the moving step comprises receiving input with the input device 521 and causing the driver 523 to move the shaft 544 based on the received input. The exercise method further comprises preventing decoupling of one or more of the plurality of weights 570 from the shaft 544 of the exercise device when the shell assembly 540 is lifted off of the base assembly 510.

An exercise system includes a plurality of exercise devices 500 each having a plurality of weights 570 configured to be positioned adjacent one another; a shaft 544 configured for movement relative to the plurality of weights 570, wherein movement of the shaft 544 relative to the plurality of weights 570 selectively couples the shaft 544 with one or more of the plurality of weights 570; a base assembly 510 having a base configured to support the plurality of weights 570 and a driver 523 configured to be coupled to and decoupled from the shaft 544; and a communication device configured to wirelessly communicate with the communication device of another one of the plurality of exercise devices 500, wherein the driver 523 of one of the plurality of exercise devices 500 is configured to move the shaft 544 of the one of the plurality of exercise devices 500 based on data received from the communication device of another one of the plurality of exercise devices 500.

The driver 523 comprises a motor 523, and each base assembly 510 further comprises a controller that electrically controls the motor 523 to move the shaft 544 based on data received from the communication device of the other one of the plurality of exercise devices 500. The driver 523 of the one of the plurality of exercise devices is further configured to move the shaft 544 of the one of the plurality of exercise devices 500 based on an input from a user of the exercise system, and is further configured to transmit the input from the user to the communication device of another one of the plurality of exercise devices 500. The communication device is configured to wirelessly communicate data corresponding to the number of weights 570 coupled to the shaft 544 of one of the plurality of exercise devices 500 to another one of the plurality of exercise devices 500.

An exercise device includes a plurality of weights 570 configured to be positioned adjacent one another; a shaft 544 configured to engage with one or more of the plurality of weights 570; a base assembly 510 having a driver 523 configured to be coupled to and decoupled from the shaft 544; and an input device 521 associated with the shaft 544 or the base assembly 510, the input device 521 being configured to receive an input from a user of the exercise device 500, the input comprising a selection corresponding to a number of the plurality of weights 570; wherein the driver 523 of the base assembly 510 is configured to automatically move the shaft 544 relative to the plurality of weights 570 when the driver 523 is coupled to the shaft 544 and when the input is received by the input device 521 to selectively engage the shaft 544 with the selected number of the plurality of weights 570.

The base assembly 510 further comprises a base configured to support the plurality of weights 570. Each of the plurality of weights 570 has an opening 582, the openings 582 of the plurality of weights 570 at least in part defining an aperture 582' extending along an axis B when the plurality of weights 570 are adjacent one another, the shaft 544 positionable within the aperture 582'. Each of the plurality of weights 570 includes one or more engagement surfaces 580/590. Movement of the shaft 544 by the driver 523 causes the shaft 544 to selectively engage with respective ones of the engagement surfaces 580/590 of the selected number of the plurality of weights 570 to prevent or limit movement of the one or more of the plurality of weights 570 in a direction orthogonal to the axis B of the aperture 582'. The shaft 544 is coupled to a handle portion oriented parallel relative to the shaft 544.

The driver 523 comprises a motor 523, and the base assembly 510 further comprises a controller that electrically controls the motor 523 to move the shaft 544 based on the input from the user of the exercise device 500. The exercise device 500 further comprises a display 519 configured to display a value corresponding to the selected number of the plurality of weights 570 or a weight corresponding to the selected number of the plurality of weights 570. A sensor 557/559 associated with the base or the shaft 544, the sensor 557/559 being configured to detect when the driver 523 is coupled to or decoupled from the shaft 544.

The handle portion 542 is provided along the shell of the shell assembly 540 and defines a handle axis B, each of the plurality of weights 570 extending radially outwardly from a weight axis B oriented parallel to the handle axis B.

The exercise device further comprising a drive shaft 527 coupled to the driver 523 and to the shaft 544 of the shell assembly 540 when the shell assembly 540 is supported by the base assembly 510, the drive shaft 527 being configured for rotation to move the shaft 544 relative to the shell of the shell assembly 540 when the drive shaft 527 is coupled to the shaft 544 of the shell assembly 540. The drive shaft 527 is positioned to extend into an interior of the shell assembly 540 when the driver 523 is coupled to the shaft 544 of the shell assembly 540 and the shell assembly 540 is supported by the base assembly 510. The drive shaft 527 is oriented orthogonally relative to a shaft axis 8 of the shaft 544 of the shell assembly 540.

The exercise device is selected from the group consisting of a dumbbell and a barbell. The plurality of weights 570 are arranged in plural groups, the groups being positioned on opposite sides of the shell assembly 540, and wherein the shell assembly 540 has plural shafts 544, each of the plural shafts 544 being coupled for movement relative to the shell and extending within the interior of the shell, wherein movement of the shafts 544 relative to the shell selectively couples the shafts 544 with one or more weights 570 in each of the groups of weights 570, and wherein movement of the shafts 544 relative to the shell selectively couples the shafts 544 with an equal number of weights 570 in each of the groups of weights 570.

The shell assembly 540 includes a handle shaft 542 and shell sub-assemblies 545, each coupled to an end portion of the handle shaft 542. Each of the shell sub-assemblies 545 at least partially defines an interior region. Drive shaft assemblies 531, each positioned at least partially within the interior region of the each of the shell sub-assemblies 545, each drive shaft assembly 531 positioned for engagement with a respective one of the shafts 544.

The exercise device further comprises plural drivers 523, each configured to be coupled to a respective one of the shafts 544 of the shell assembly 540 when the shell assembly 540 is supported by the base assembly 510, each of the drive shaft assemblies 531 being releasably couplable to a respective one of the drivers 523. Each of the shafts 544 having a gear rack 572, and the drive shaft surface of each of the drive shaft assemblies 531 including a gear 561 engaged with the gear rack 572 of a respective one of the shafts 544.

At least two weights 570 are configured to be placed adjacent one another along an axis B of the weights 570 to form a pair of weights, a first weight of the pair of weights including a male surface 580 and a second weight of the pair of weights including a female surface 590 configured to be engaged by the male surface 580 of the first weight, thereby limiting or eliminating movement of the first weight and the second weight of the pair of weights 570 relative to one another along the axis B. The first weight and the second weight of the pair of weights 570 each defines an aperture 582 extending along the axis B to receive the shaft 544 of the shell assembly 540 to selectively couple the shaft 544 with the first weight and the second weight, the shaft 544 limiting or eliminating movement of the first weight and the second weight of the pair of weights 570 relative to one another in a direction orthogonal to the axis B.

The shell assembly 540 including a memory configured to store data corresponding to movement of the shell assembly 540. The base assembly 510 including a memory configured to receive the data corresponding to movement of the shell assembly 540.

The base assembly 510 and the shell assembly 540 being configured to share the data corresponding to movement of the shell assembly 540 when the base assembly 510 is supporting the shell assembly 540. The base assembly 510 being configured to wirelessly transmit the data corresponding to movement of the shell assembly 540 to a remote device.

Referring now more specifically to details of the embodiment illustrated in FIGS. 14A-14G, 15 and 18A-18F, base assembly 510 provides support for the components of device 500. Base assembly 510 has a semi-cylindrical housing 512 and a base cover 513 that is removably mounted to the lower surface of the housing 512.

Figure 15A:
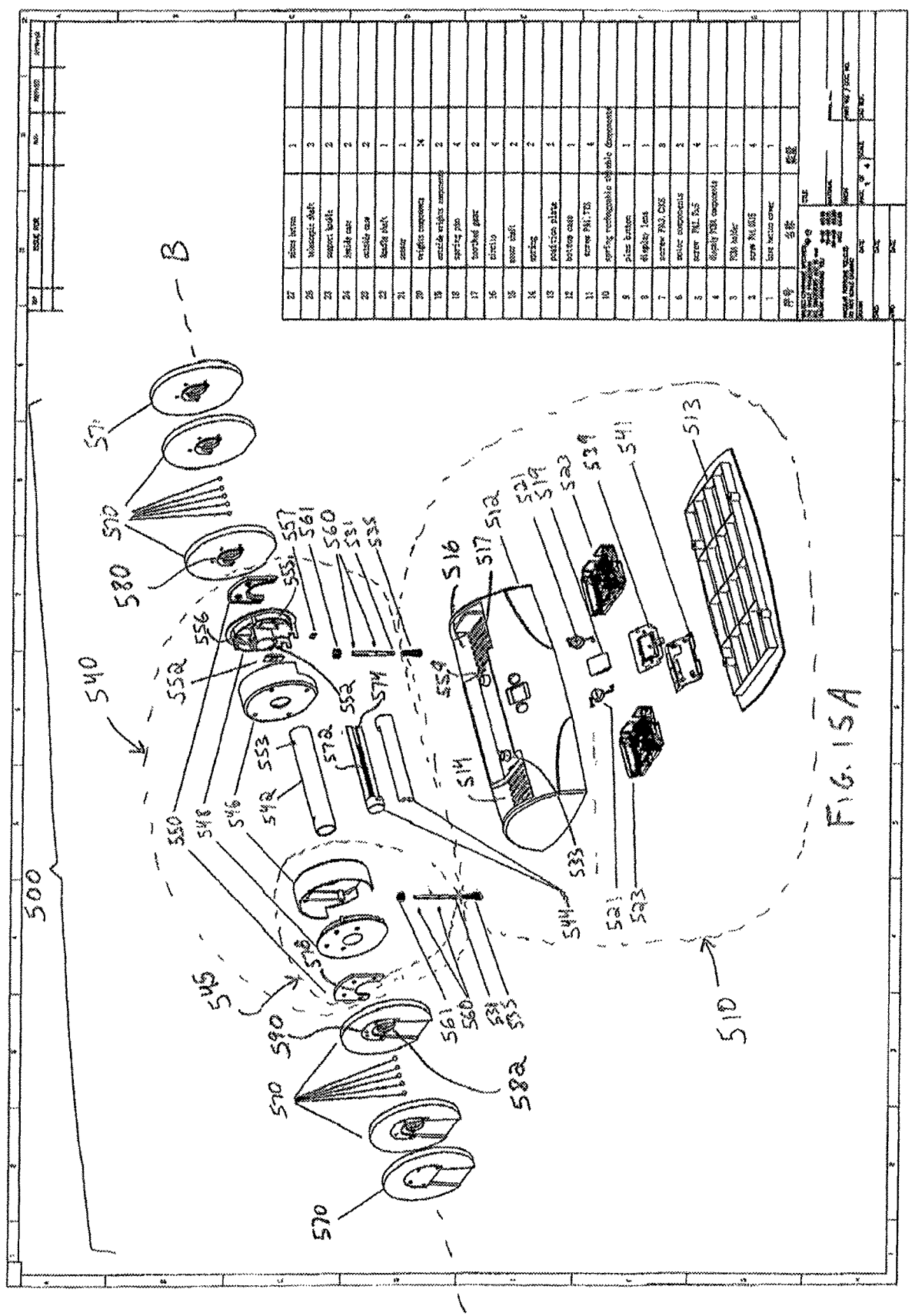

Housing 512 includes one or more exterior surfaces on which other components of device 500 may rest. As shown in FIG. 15, housing 512 of base assembly 510 includes a first surface 514 and a second surface 516 on an upper portion thereof. Surfaces 514 and 516 form a base configured to support shell assembly 540 and weights 570. Each surface 514, 516 includes upwardly protruding ribs 517 that are uniformly spaced apart and configured to support weights 570, e.g., in a stacked orientation. The lower surface of a weight 570 is sized to fit between two adjacent ribs 517.

Housing 512 includes a user control interface in the form of two user-operable buttons 521 for selecting a desired weight, and a display 519 disposed between buttons 521 for displaying the selected weight. One button 521 is labeled '+' for increasing the amount of weight (i.e., the number of weights 570) that is non-removably attached to shell assembly 540, and the other button 521 is labeled '−' for decreasing the amount of weight (i.e., the number of weights 570) that is non-removably attached to shell assembly 540. Buttons 521 may be generally referred to herein as a user input device.

An interior region is defined within housing 512 which houses certain components of device 500. As best shown in FIG. 14G, according to this exemplary embodiment, a driver in the form of two motors 523 are mounted within the interior region. The driver is configured to adjust the amount of weight applied to shell assembly 540. Each motor 523 has an output shaft 525 that is configured to rotate about an axis. Those skilled in the art will recognize that driver may vary from that which is shown and described. For example, the driver could comprise a single motor 523.

Each output shaft 525 is non-rotatably connected to an intermediate shaft 527 such that the shafts 525 and 527 rotate together. The lower end of each intermediate shaft 527 is fixed to one of output shafts 525 such that shafts 525 and 527 rotate together, and the upper end of each intermediate shaft 527 includes an opening 529 that is configured to releasably receive a shaft 531 that forms part of shell assembly 540. Opening 529 of shaft 527 is keyed to the lower end of shaft 531 such that shafts 531 and 527 rotate together. It should be understood that shafts 531 and 527 are capable of being regularly detached and re-attached during operation of device 500.

The upper end of each intermediate shaft 527 is positioned within a hollow cylinder 533 (see FIG. 15) that protrudes from the top surface of housing 512, such that opening 529 in shaft 527 is visible and accessible from the exterior of housing 512. A spring 535 is positioned between the top end of shaft 527 and the interior surface of cylinder 533 to center shaft 527 within cylinder 533 and also ensure a positive connection between shafts 527 and 531. The top end of each intermediate shaft 527 may be flush with the top surface of cylinder 533. Alternatively, the top end of each intermediate shaft 527 may be either slightly depressed or protruding with respect to the top surface of cylinder 533.

A printed circuit board (PCB) 539 for interacting with display 519 and buttons 521 is mounted within housing 512. PCB 541, is also mounted within housing 512 for controlling motors 523 based upon signals received from PCB 541, as will be described later. PCB 541 includes (at least) a processor, controller and a wireless transmitter/receiver for transmitting/receiving wireless signals, such as Bluetooth or Wi-Fi.

Referring now to shell assembly 540, shell assembly 540 is essentially a barbell without any weights 570 applied thereto. Shell assembly 540 generally includes a handle shaft 542 in the form of a hollow cylinder, a two-piece telescopic shaft 544 positioned within the hollow interior of handle shaft 542, and two shell sub-assemblies 545 mounted to opposing sides of shaft 542.

Shell sub-assemblies 545 are substantially identical and only one of the shell sub-assemblies 545 will be described hereinafter. Shell sub-assembly 545 generally includes a shell comprising a bowl-shaped cylindrical inner case 546, which is positioned closest to an end of shaft 542, an outer case 548 that is mounted to the open end of inner case 546, and a female dovetail connector 550 that is mounted to an exterior facing surface of outer case 548. A circular opening is formed through each shell sub-assembly and is substantially aligned with the longitudinal axis B.

As best shown in FIG. 14G, outer case 548 comprises a hollow cylinder 552 in which one end of the shaft 542 is received. Shaft 542 is fixedly and non-rotatably mounted to cylinder 552 by the shafts 531 that pass through holes 553 in shaft 542. Outer case 548 includes a series of snap connection features 555 that are releasably connected to mating features on inner case 546 for fastening the cases 546 and 548 together. Other means for mounting shaft 542, case 546 and case 548 are known to those skilled in the art.

A series of mechanical components are positioned within the hollow region defined between cases 546 and 548. More particularly, and referring still to only one of the substantially identical shell sub-assemblies 545, the shaft 531 is rotatably mounted within the hollow region. Shaft 531 registers with (i.e., passes through) opposing holes 553 in handle shaft 542 and opposing holes 556 in cylinder 552 of outer case 548. A c-clip 560 is mounted in a groove formed in shaft 531 at a location above cylinder 552, and another c-clip 560 is mounted in a groove formed in shaft 531 at a location below cylinder 552, thereby locking the axial position of shaft 531 with respect to handle shaft 542. It should be understood that shaft 531 is capable of rotating within holes 553 and 556, but does not translate relative to holes 553 and 556.

A toothed gear 561 is non-rotatably mounted to a central region of shaft 531 such that shaft 531 and gear 561 rotate together. Gear 561 and shaft 531 together form a drive shaft assembly. Gear 561 may be capable of translating to a slight degree along the length of shaft 531 (i.e., along axis A) to accommodate for misalignment between gear 561 and the toothed gear rack 572 on shaft 544 with which gear 561 is meshed.

Referring now to the features of telescopic shafts 544a and 544b (referred to collectively or individually as shaft(s) 544) of shell assembly 540, each telescopic shaft 544 has a substantially cylindrical shape having a cut-out region that defines a half-cylindrical section along a majority of the length of shaft 544. A rectangular channel 574 is formed along the length of the interior facing side (i.e., the side facing axis B) of the half-cylindrical section. Gear teeth forming a toothed gear rack 572 are defined along a substantial portion of the channel 574. In assembled form, the flat faces of the half-cylindrical sections are positioned to face each other. Each gear 561 is positioned within the channels 574 of both shafts 544, and the teeth of each gear 561 are meshed with both toothed gear racks 572, such that rotation of at least one of gears 561 about axis A causes translation of both shafts 544 along axis B. In normal operation, both gears 561 are rotated at the same time by motors 523 to cause translation of both shafts 544 along axis B. It should be understood that axes A and B are orthogonal. Due to the toothed engagement between the gears 561 and the toothed gear racks 572, the shafts 544 are configured to simultaneously translate in opposite directions. Shafts 544 are configured to move between a retracted position (see FIG. 18F) in which shafts 544 do not engage any weights 570, and a deployed position (see FIG. 14G) in which shafts 544 engage one or more weights 570.

Referring back to the features of the shell sub-assemblies 545, for one of the shell sub-assemblies 545, electronic components are also accommodated in the hollow region that is defined between cases 546 and 548. The electronic components include (i) a sensor 552 in the form of an accelerometer (for example) that senses motion of device 500, (ii) a rechargeable battery for powering sensor 552, and (iii) a PCB including memory and a processor for communicating readings of sensor 552 to base assembly 510 in a docked state of device 500. Spring pins 557 (also referred to as contacts) are connected to the PCB of shell sub-assembly 545 to transfer signals and power to and from PCB 541 of base assembly 510 in a docked state of shell assembly 540.

Female dovetail connector 550 of the shell sub-assembly 545 is mounted to an exterior facing surface of outer case 548, and is configured to be releasably mounted over a male dovetail connector 580 that is disposed on an adjacent weight 570. Female dovetail connector 550 may be mounted to case 548 by fasteners, for example, or, alternatively, female dovetail connector 550 may be formed with case 548 as a unitary member.

Female dovetail connector 550 includes a semi-circular female dovetail recess 576 having an open end on the lower surface. The open end is configured to slidably receive the male dovetail connector 580 on the adjacent weight 570. As will also be described with reference to FIG. 17, the dovetail joint formed between female connector 550 and male dovetail connector 580 of weight 570 prevents outer case 548 (along with the entire shell assembly 540) from rotating about axis B with respect to the attached weight 570. The dovetail joint also prevents the attached weight 570 from moving upward with respect to outer case 548 (and the entire shell assembly 540). The dovetail joint does not prevent the attached weight 570 from moving downward along axis A with respect to shell assembly 540—such downward translation is only prevented when one of the telescopic shafts 544 is positioned within an opening 582 formed in the attached weight 570. More particularly, when the telescopic shafts 544 is positioned within the opening 582 formed in the attached weight 570, the attached weight 570 is prevented from detaching from shell assembly 540 in the vertical direction due to the inter-engagement between the shaft 544, the central hole in the outer case 548, and opening 582 in the attached weight 570. The attached weight 570 is prevented from detaching from shell assembly 540 in the horizontal direction due to the inter-engagement between female dovetail connector 550 and male dovetail connector 580.

Referring now to the features of weights 570, the weights 570 are substantially identical and only one weight 570 will be described hereinafter with reference to FIGS. 16A-16G. Weight 570 is a circular plate having a first side 581, a second side 583 opposite first side 581, and a revolved surface 584 extending between and interconnecting the two sides 581 and 583. The base 584a of revolved surface 584 is flat for seating on a surface 514, 516 of housing 512. A circular opening 582 is formed in the center of weight 570 and is substantially aligned with the longitudinal axis B of weight 570.

Figure 17:
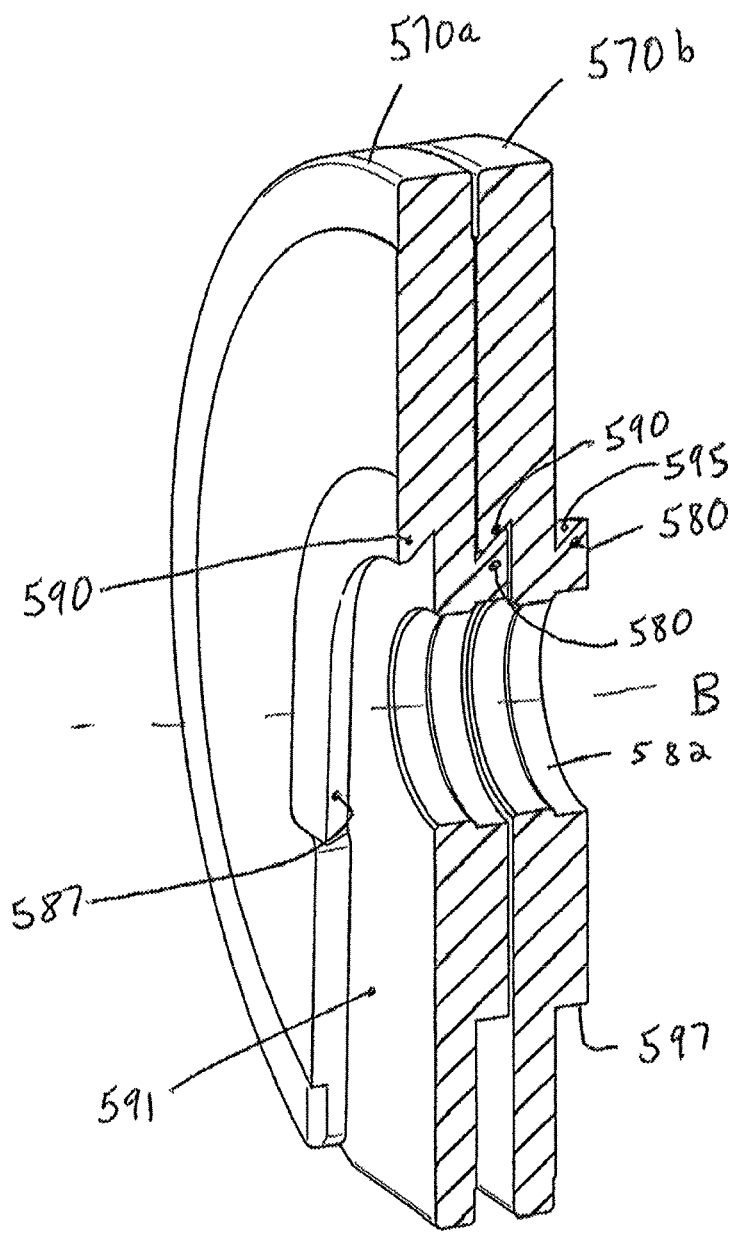
FIG. 17 depicts a cross-sectional side view of two weights mated together.
Figure 18B:
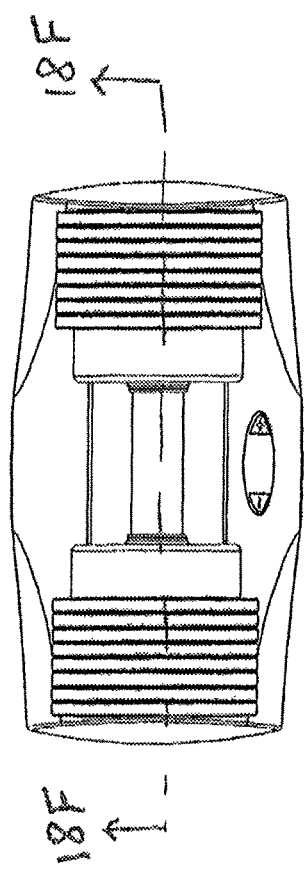
FIG. 18B is a top plan view of the exemplary exercise device of FIG. 18A.
Figure 18C:
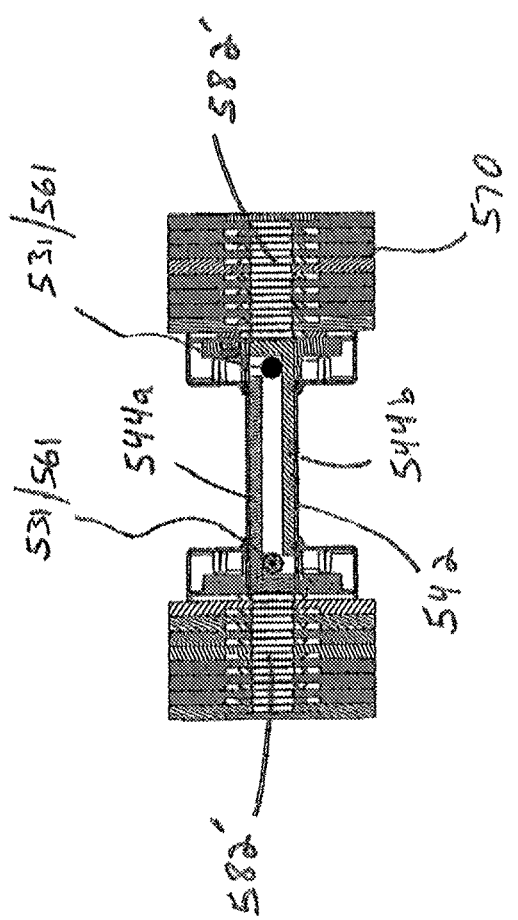
FIG. 18C depicts a cross-sectional side view of the device of FIG. 18A taken along the lines 18C-18C.
Figure 18E:
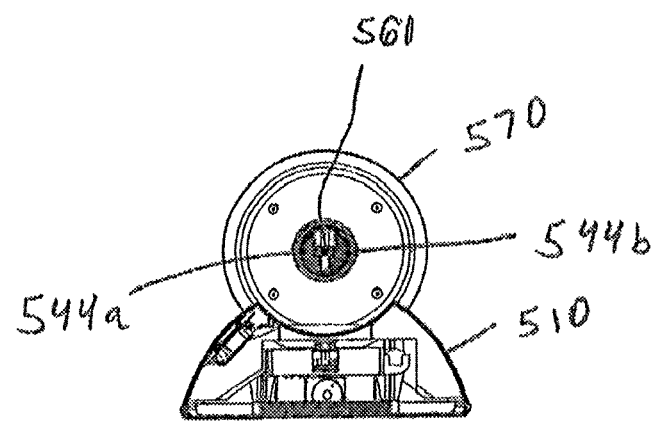
FIG. 18E depicts a cross-sectional side view of the device of FIG. 18A taken along the lines 18E-18E.

Weight 570 includes a female dovetail connector 590 on a first side 581, and a male dovetail connector 580 on second side 583. The female dovetail connector 590 of a first weight 570 is configured to mate with a male dovetail connector 580 of a second weight 570b adjacent the first side 581 of the first weight, whereas the male dovetail connector 580 of the first weight 570 is configured to mate with a female dovetail connector 590 of a third weight 570 adjacent second side 583 of the first weight 570. FIG. 17 depicts the interconnection between the female dovetail connector 590 of weight 570b and male dovetail connector 580 of weight 570a. Various features in FIG. 17 are shown in a simplified form to facilitate understanding of the interconnection.

Male dovetail connector 580 and female dovetail connector 590 may be generally referred to herein as engagement surfaces. Those skilled in the art will recognize that other connector styles exist for accomplishing connection and disconnection between two bodies. Thus, connectors 580 and 590 may vary from that which is shown and described.

As best shown in FIG. 16A, side 581 of weight 570 includes a U-shaped cut-out portion extending from side 581 to planar surface 591. An opening 585 is formed at the base of the cut-out portion that intersects base 584a of weight 570. Upon docking the shell assembly 540 onto base assembly 510, the opening 585 is sized to first receive a male dovetail joint 580 of an adjacent weight 570 that is already docked on base assembly 510, and is also sized to thereafter receive one of the ribs 517 of housing 512. The shape of the opening 585 and rib 517 are complimentary to ensure that weight 517 can only be installed onto housing 512 in a single orientation thereby preventing improper installation of weights 517 onto housing 512.

Angled walls 586 extend in an A-shape. More particularly, angled walls 586 extend in a distal direction from the opposing ends of opening 585 and are slanted toward the longitudinal axis B of weight 570. In an assembled form of device 500, male dovetail connector 580 of an adjacent weight 570 is positioned between angled walls 586. Accordingly, angled walls 586 are configured to prevent rotation of an adjacent weight 570 that is mated thereto.

The female dovetail connector 590 extends between and connects the distal ends of the angled walls 586. The female dovetail connector 590 comprises a female dovetail surface 587 that extends about axis B. Female dovetail surface 587 is U-shaped about axis B and extends between and connects the distal ends of angled walls 586. Female dovetail surface 587 is also angled in a depth direction (i.e., along axis 8) from first side 581 to second side 583 and both surrounds and faces the longitudinal axis B. As best seen in FIG. 16G, as viewed in a direction from first side 581 to second side 583 of weight 570, female dovetail surface 587 extends in an outward direction (e.g., at a 45 degree angle) leading away from longitudinal axis B of weight 570. As best shown in FIG. 17, female dovetail connector 590 of one weight 570b is designed to trap a mating male dovetail connector 580 of a mating weight 570a between the angled surface of female dovetail surface 587 and planar surface 591 of weight 570a.

Female dovetail connector 590 may form part of a separate insert that is fastened to first side 581 of weight 570 as shown in FIG. 16A, or, alternatively, female dovetail connector 590 may be unitized with first side 581 of weight 570 as shown in FIG. 17.

Figure 16B:
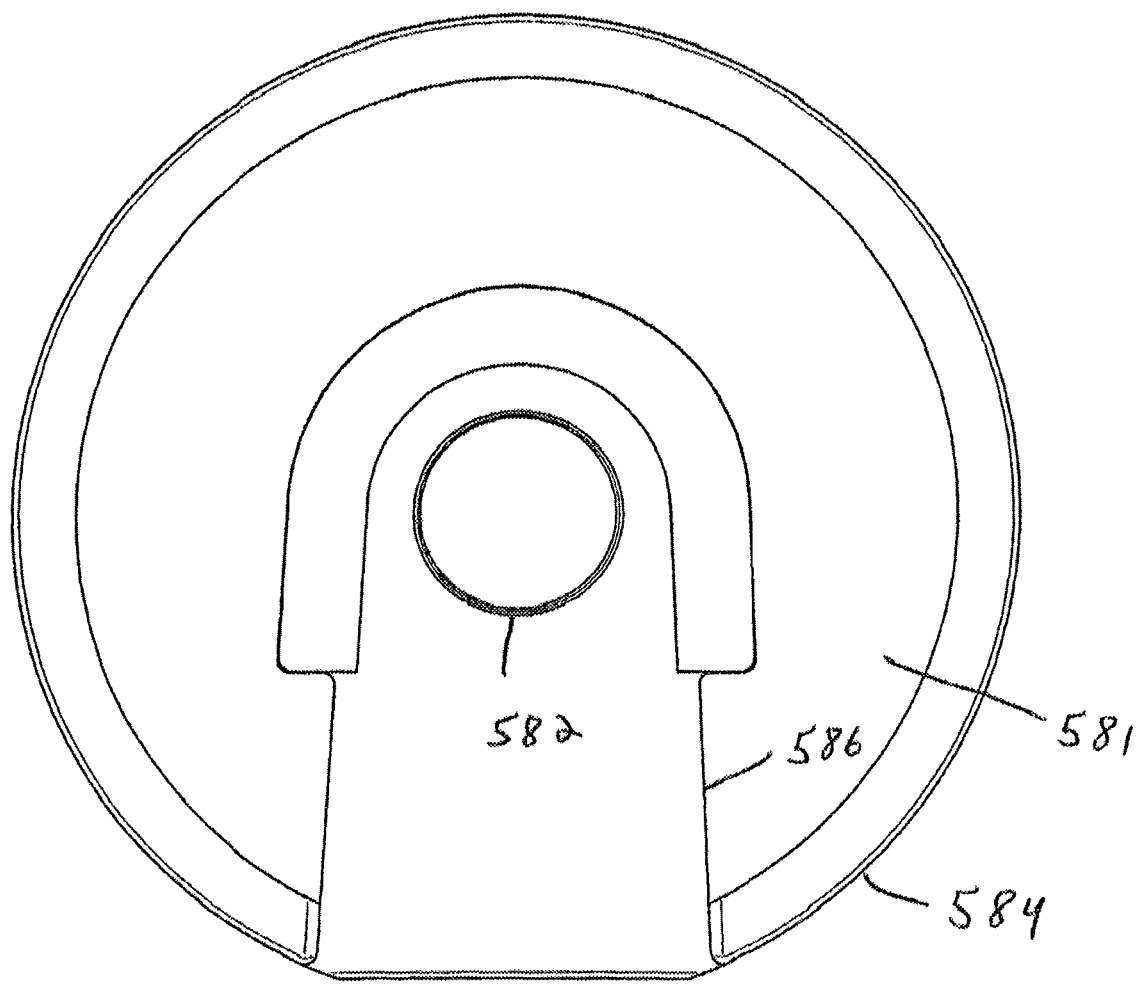
Figure 16D:
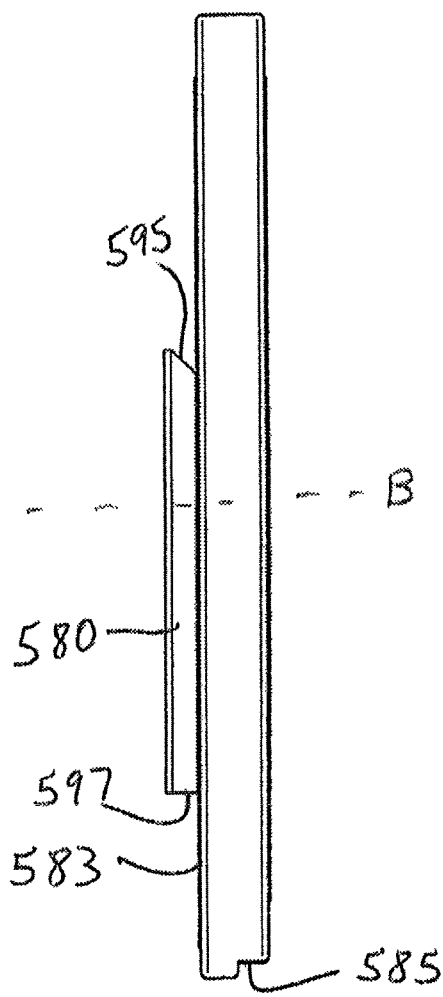
Figure 16E:
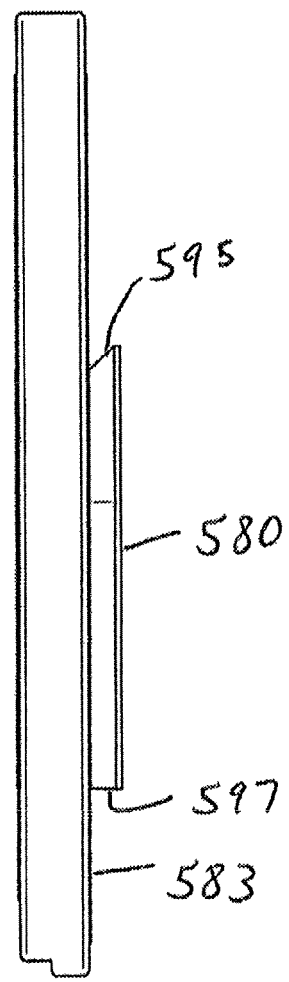
Figure 16F:
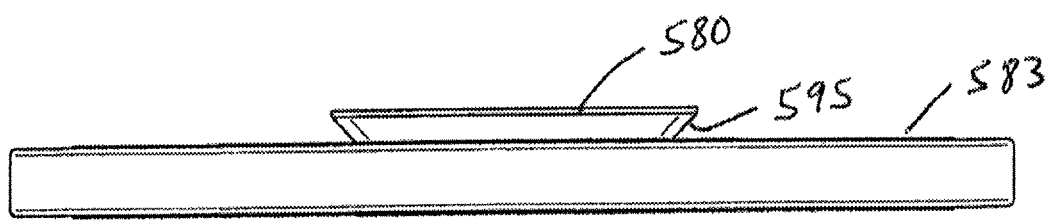
Figure 16G:
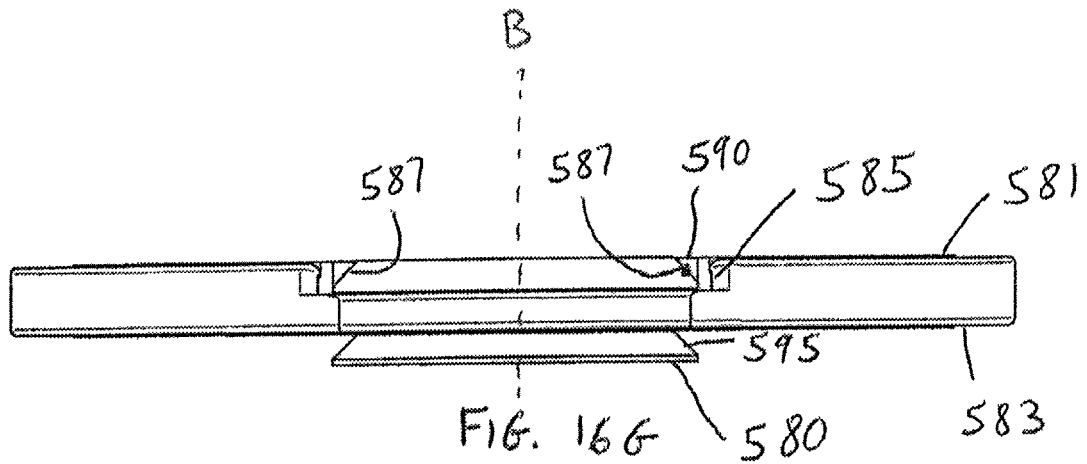

As best shown in FIGS. 16C-16G, side 583 of each weight 570 includes a male dovetail connector 580. Male dovetail connector 580 is a tombstone shaped protrusion that extends outwardly from side 583 along axis B. Male dovetail connector 580 includes a flat bottom surface 597 that is substantially parallel to base surface 584a of weight 570. A dovetail surface 595 extends from and connects the opposing ends of flat bottom surface 597. Dovetail surface 595 is U-shaped and surrounds axis B. As best shown in FIG. 16D, dovetail surface 595 extends outwardly at an acute angle (e.g. 45 degrees) from second side 583 and in a direction leading away from axis B. As best shown in FIG. 17, male dovetail surface 595 of one weight 570a is designed to be trapped between the angled surface of female dovetail surface 587 and planar surface 591 of a mating weight 570b.

Male dovetail connector 580 may form part of a separate insert that is fastened to second side 583 of weight 570, or, alternatively, male dovetail connector 580 may be unitized with second side 583 of weight 570.

The dovetail joint formed between female dovetail connector 590 and male dovetail connector 580 of two mated weights 570 prevents those mated weights from rotating about axis B with respect to each other. As shown in FIG. 17, the dovetail joint also prevents attached weight 570a from moving upward along axis A with respect to the other attached weight 570b. The dovetail joint does not prevent the attached weight 570a from moving downward or the attached weight 570b from moving upward—such translation is only prevented when one of the telescopic shafts 544 is positioned within openings 582 formed in the weights 5708 and 570b. It should be understood that the stack of aligned openings 582 together form an aperture 582' through which the shaft 544 can travel. More particularly, when the telescopic shaft 544 is positioned within the openings 582 formed in the attached weights 570a and 570b, the attached weights 5708 and 570b are prevented from detaching from each other. Stated differently, the dovetail joint provides one degree of freedom for two weights 570 that are mated together, and that one degree of freedom is eliminated once telescopic shaft 544 is positioned within the openings 582 in those weights.

Operation of device 500 will now be described with reference to FIGS. 14A, 14G, 18F and 17. Operation of device 500 is similar to that of the device 100, and the primary differences will be described hereinafter.

As best shown in FIG. 14A, in an assembled and docked state of device 500, weights 570 are nested together and positioned on base assembly 510. In the nested state, all of the weights 570 are interconnected together, as at least partially shown in FIG. 17, such that the weights 570 are prevented from rotating relative to one another by the mating geometries of male dove connectors 580 and female dove connectors 590.

In the docked state of device 500, shell assembly 540 is docked on base assembly 510, and the spring pins 557 on shell assembly 540 are positioned in direct physical contact with electrical contacts 559 on the top surface of base assembly 510. Power and signals are passed between spring pins 557 and electrical contacts 559. More particularly, signals corresponding to readings of sensor 552 are transmitted from the PCB of shell assembly 540 to spring pins 557, to electrical contacts 559 and to PCB 541 of base assembly 510 such that the readings of sensor 552 are uploaded to the memory of base assembly 510. Also, power is transmitted from PCB 541 of base assembly 510 then to electrical contacts 559 then to spring pins 557 then to the PCB of shell assembly 540 and then to the rechargeable battery of shell assembly 540 for recharging the rechargeable battery. The rechargeable battery provides power to the sensor 552 of shell assembly 540 as well as any other components of shell assembly 540 requiring power. As a result of the interconnection between the spring pins 557 and electrical contacts 559, the PCB 541 of base assembly 510 understands that shell assembly 540 is docked on base assembly 510. If electrical contacts 559 on base assembly 510 do not receive signals from spring pins 557, then base assembly 510 understands that shell assembly 540 is removed from base assembly 510, and base assembly 510 will not operate motors 523 in response to a user depressing buttons 521. The above described communication and electrical interface between shell assembly 540 and base assembly 510 is also applicable to shell assembly 140 and base assembly 110 of device 100.

Before device 500 is used, a user first selects the amount of desired weight for a particular exercise routing using device 500 by depressing one of buttons 521 on base assembly 510 while shell assembly 540 is docked on base assembly 510. Depressing one of buttons 521 causes the desired weight to display on display 519, and also causes motors 523 to activate and rotate their output shafts 525 in the same direction. Rotating output shafts 525 causes rotation of shafts 531 and their toothed gears 561. Toothed gears 561 rotate about their axes in the same direction, which causes telescopic shafts 544 to either translate outwardly along axis B (i.e., away from handle 542) or translate inwardly along axis B (i.e., toward handle 542) due to the geared arrangement between toothed gears 561 and gear teeth 572 of telescopic shafts 544.

More particularly, if a user selects a "−" button 521 indicating a desire to use less weight than was previously used and displayed on display 519, then the gears 561 rotate in a direction to cause telescopic shafts 544 to translate inwardly and in opposite directions along axis B (i.e., toward handle 542). Telescopic shafts 544 move a discrete distance along axis B and disengage from the openings 582 in one or more weights 570. The distance travelled by shafts 544, which is caused by rotation of motors 523, is controlled by the processor on PCB 541 of base assembly 510. The distance travelled by shafts 544 is directly proportional to the weight selected by the user using button 521.

Once telescopic shafts 544 disengage from an opening 582 in a weight 570, then that weight 570 will detach from shell assembly 540 once shell assembly 540 is removed from base assembly 510. In other words, that weight 570 will remain docked on base assembly 510 once shell assembly 540 is removed from base assembly 510. For example, with reference to FIG. 17, if a telescopic shaft 544 is initially engaged with both weights 570a and 570b, and the telescopic shaft 544 is translated such that it is no longer positioned within opening 582 of weight 570a, then when the user removes the shell assembly 540 from base assembly 510, weight 570b will be attached to shell assembly 540 while weight 570a will remain docked on base assembly 510. Stated differently, the dovetail joint is configured to permit adjacent weights to become detached when a shaft 544 is not positioned within an opening 582 in one of those weights.

The user then removes shell assembly 540 along with weights 570 attached thereto and performs an exercise routine. Once electrical contacts 559 of base assembly 510 become detached from spring contacts 557 of shell assembly 540, the processor of base assembly 510 knows that shell assembly 540 has been removed from base assembly 510 and an exercise routine is underway.

Alternatively, if a user selects a "+" button 521 indicating a desire to use more weight than was previously used and displayed on display 519, then the gears 561 rotate to cause telescopic shafts 544 to translate outwardly along axis B (i.e., away from handle 542). Telescopic shafts 544 move a discrete distance along axis B and engage with the openings 582 in one or more additional weights 570. The distance travelled by shafts 544, which is caused by rotation of motors 523, is controlled by the processor on PCB 541 of base assembly 510. The distance travelled by shafts 544 is directly proportional to the weight selected by the user. Once telescopic shafts 544 engage an opening 582 in a weight 570, then that weight 570 cannot be detached from shell assembly 540 once shell assembly 540 is removed from base assembly 510. The user then removes shell assembly 540 along with weights 570 attached thereto and performs an exercise routine.

As another alternative, if the user does not desire to change the amount of weight than was previously used and displayed on display 519, then the user can simply remove shell assembly 540 (along with weights 570 that are connected thereto) from base assembly 510 and begin an exercise routine using shell assembly 540 and any weights 570 that are connected thereto.

Following the exercise routine, the user returns the shell assembly 540 to base assembly 510 (i.e., docks shell assembly 540). Upon returning the shell assembly 540 to base assembly 510, the openings 585 in the outermost weights attached to shell assembly 540, travel over the male dovetail connectors 580 on the innermost weights 570 that are docked on base assembly 510. Further downward translation of shell assembly 540 causes the lower end of each shaft 531 on shell assembly 540 to engage in a respective opening 529 on intermediate shaft 527 of base assembly 510. Spring contacts 557 then physically engage electrical contacts 559 on base assembly 510. Opening 529 of shaft 527 may be keyed to the lower end of shaft 531 such that shafts 531 and 527 rotate together.

Once the shell assembly 540 is docked on the base assembly 510, data is transmitted from the PCB of the shell assembly 540 to PCB 541 of base assembly 510 due to the interconnection of contacts 557 and 559. The base assembly 510 is configured to interpret and/or transmit that data via the wireless transmitter/receiver of PCB 541 to a remote device, such as a smart phone or a computer. The data contains information related to the amount of weight used in an exercise routine, the number of curls, reps or motions in the exercise routine (as measured by accelerometer of shell assembly 540) and the time duration of the exercise routine, for example. The smart phone or computer contains a program that is configured to track the data for each exercise routine.

Turning now to FIGS. 19-24, examples of systems and methods for monitoring and/or assessing physical fitness of a user from disparate exercise devices and activity trackers are illustrated. The systems and methods can include exercise devices such as, for example, one or more exercise devices or apparatus 100 and/or one or more exercise devices or apparatus 500. Although reference is made in various examples to systems and methods employing exercise device 100, it is contemplated that exercise device 500 or any other exercise device is optionally additionally or alternatively included in the systems or methods.

Generally, a system according to one example is provided for assessing wellness of a user. The system includes a plurality of devices each configured to collect user data generated for the user and to transmit the user data. At least one of the devices is an exercise device and at least one of the devices is a measurement device. A processor is coupled for communication with the devices. The processor is configured to receive the user data from the plurality of devices, compare the received user data to prior or other user data, generate an assessment of the wellness of the user from the comparison of the received user data and the prior or other user data, and communicate the assessment to the user. The user data collected by the exercise device includes usage of the exercise device by the user. The user data collected by the measurement device includes a physical condition of the user.

In another example, a physical fitness assessment system is configured for use with at least one exercise device including an exercise device network communication interface for communication over a network, a sensor configured to sense use of the at least one exercise device by a user, an exercise device memory, an exercise device processor coupled to the exercise device network communication interface, the sensor, and the exercise device memory, and exercise device programming. The programming configures the at least one exercise device to perform functions to track, via the sensor, use of the at least one exercise device by the user, determine current physical activity data of the user based on, at least, the tracked use of the at least one exercise device by the user, and transmit over the network, via the exercise device network communication interface, the current physical activity data of the user. The physical fitness assessment system includes an image display for presenting a physical fitness assessment based, at least, on the tracked current physical activity data of the user; a user input device for receiving from the user a physical fitness assessment request to generate the physical fitness assessment; and a computer processor coupled to the image display and the user input device. The computer processor is configured to receive from the exercise device, via the network, the tracked current physical activity data of the user; receive from the user, via the user input device, the request to generate the physical fitness assessment; compare the current physical activity data of the user against benchmark physical activity data correlated with the at least one exercise device; based on the comparison, determine a physical fitness assessment of the user; and present to the user, via the image display, the physical fitness assessment.

FIG. 19 is a high-level functional block diagram of an example physical fitness assessment system 1900 including the exercise device 100 with the movement tracker 118 to identify current physical activity based on exercise device programming 1945 (which includes, for example, a neural network model), a mobile device 1990, and a server system 1998 connected via various networks. Exercise device 100 is connected with a host computer. For example, the exercise device 100 is paired with the mobile device 1990 via the high-speed wireless connection 1937 or connected to the server system 1998 via the network 1995. In some examples, the host computer may be a wearable device like the example smartwatch shown for the activity tracker 2010 described in further detail below.

Physical fitness assessment system 1900 includes at least one exercise device 100, which is can include free-weight training equipment (e.g., dumbbell, kettlebell, or barbell) In the example of FIG. 19. Exercise device 100 includes the movement tracker 1918 and an image display 1980. Exercise device 100 also includes or is otherwise directly or indirectly associated with an image display driver 1942, image processor 1912, and a micro-control unit (MCU) 1930. Image display 1980 is for presenting images and videos, which can include a sequence of images. Image display driver 1942 is coupled to the image display 1980 to present the images. The components shown in FIGS. 19-21 for the exercise device 100, 2100A-D are located on one or more circuit boards, for example a PCB or flexible PCB.

Movement (movt) tracker 1918 is an electronic device, such as an Inertial measurement unit (IMU), that measures and reports for example a body's specific force, angular rate, and sometimes the magnetic field surrounding the body, using a combination of accelerometers and gyroscopes, sometimes also magnetometers. For example, as mentioned previously, an accelerometer can be Included in a kettlebell or dumbbell. A neural network model can be used to track the number of repetitions, number of sets, or other manipulations made to or sensed by the exercise device. Such accelerometer measurements can be processed on a separate computing device (e.g. a mobile device) to track the number of repetitions, number of sets, or other manipulations if the exercise device (e.g., kettlebell and/or dumbbell) itself tracks the manipulations.

If a magnetometer is present, the magnetic field can be used as input to detect specific physical activities (e.g., weightlifting—number of repetitions, number of sets, etc.) that are dependent on Earth's or an artificial magnetic field. In this example, the inertial measurement unit determines a rotation acceleration of the exercise device 100, 2100A-D, mobile device 1990, or a wearable device 2010. The movement tracker 1918 works by detecting linear acceleration using one or more accelerometers and/or rotational rate using one or more gyroscopes. The inertial measurement units can contain one accelerometer, gyroscope, and magnetometer per axis for each of the three axes: horizontal axis for left-right movement (X), vertical axis (Y) for top-bottom movement, and depth or distance axis for up-down movement (Z). The gyroscope detects the rate of rotation around 3 axes (X, Y, and Z). The magnetometer detects the magnetic field (e.g., facing South, North, etc.) like a compass which generates a heading reference, which is a mixture of Earth's magnetic field and other artificial magnetic field (such as ones generated by power lines). The three accelerometers detect acceleration along the horizontal (X), vertical (Y), and depth or distance (Z) axes defined above, which can be defined relative to the ground, the exercise device 100, 2100A-D, mobile device 1990, the wearable device 2010, or the user moving the exercise device 100, 2100A-D or activity tracker 2010; or holding (or carrying) the mobile device 990. Thus, the accelerometer detects a 3 axis acceleration vector, which then can be used to detect Earth's gravity vector.

Generally, the neural network is pre-trained with a labeled data set, then on the exercise device 100, the neural network is executed through a forward-pass mechanism where the inputs (model input layer 1959A-N) is presented and the trained weights are used to calculate the outputs (model output layer 1968A-N). The outputs represent the probabilities of each set and repetitions to be tracked when the exercise device 100 is lifted by the user.

In the physical fitness assessment system 1900, exercise device 100 includes the model input layer 359A-N, which is tracked movement over time period 1960 for the exercise device 100. Tracked movement over time period 1960 includes accelerometer measurements 361A-N, which includes measured acceleration (MA) 1962A-N and measured acceleration time coordinates 1963A-N to indicate when the measured acceleration 1962A-N was taken. Tracked movement over time period 1960 further includes gyroscope measurements 1964A-N, which includes measured rotation (MR) 1965A-N, measured rotation time coordinates 1966A-N to indicate when the measured rotation 1965A-N was taken, and motion interrupt time coordinates 1967A-N (e.g., times when motion is detected).

As shown, memory 1934 further includes exercise device programming 1945 to perform a subset or all of the functions described herein for the exercise device 100. Although the neural network model can include an input layer, hidden layers and output layer, in the example the neural network model of the exercise device programming 1945 includes convolutional layers (several), fully connected layers (these used to be hidden layers) and a single output layer. Exercise device programming 1945 has a trained exercise device model (e.g., shown as weightlifting model 1946), a set of weights 1947A-N, and hidden layers 1948. Memory 1934 further includes a model output layer 1968A-N. Model output layer 1968A-N has an identified number of sets 1969A-N, an identified number of repetitions 1970A-N, set confidence levels 1971A-N for the identified number of sets 1969A-N, and repetition confidence levels 1972A-N for the identified number of repetitions 1970A-N per set.

In one example, the inputs—model input layer 1959A-N, such as the tracked movement over time period 1960 measurements taken by the movement tracker 1918, may be transmitted to the mobile device 1990 or a wearable device 2010 from the exercise device 100. The mobile device 1990 or the wearable device 2010 include the trained exercise device model (e.g., shown as weightlifting model 1946), the set of weights 1947A-N, and the hidden layers 1948. Mobile device 1990 or the wearable device 2010 can then calculate the outputs (model output layer 1968A-N) from the inputs to determine the current physical activity data 1975A.

MCU 1930 includes processor 1932, memory 1934, and high-speed wireless circuitry 1936. In the example, the image display driver 1942 is coupled to the high-speed circuitry 1930 and operated by the high-speed processor 1932 in order to drive the image display 1980. Processor 1932 may be any processor capable of managing high-speed communications, low-speed communications, and operation of any general computing system needed for exercise device 100. Processor 1932 includes processing resources needed for managing high-speed data transfers on high-speed wireless connection 1937 to a wireless local area network (WLAN) using high-speed wireless circuitry 1936. In certain embodiments, the processor 1932 executes firmware that includes the exercise device programming 345 and an operating system, such as a LINUX operating system or other such operating system of the exercise device 100 and the operating system is stored in memory 1934 for execution. In addition to any other responsibilities, the processor 1932 executing a software architecture for the exercise device 100 is used to manage data transfers with high-speed wireless circuitry 1936 (network communication interface or transceiver). In certain embodiments, high-speed wireless circuitry 1936 is configured to implement institute of Electrical and Electronic Engineers (IEEE) 802.11 communication standards, also referred to herein as Wi-Fi. In other embodiments, other high-speed communications standards may be implemented by high-speed wireless circuitry 1936.

Low-power wireless circuitry 1924 (network communication interface or transceiver) and the high-speed wireless circuitry 1936 of the exercise device 100 can Include short range transceivers (Bluetooth™) and wireless wide, local, or wide area network transceivers (e.g., cellular or WiFi). Mobile device 1990, including the transceivers communicating via the low-power wireless connection 1925 and high-speed wireless connection 1937, may be implemented using details of the architecture of the exercise device 100, as can other elements of network 1995.

Mobile device 1990 may be a smartphone, tablet, laptop computer, access point, or any other such device capable of connecting with exercise device 100 using both a low-power wireless connection 1925 and a high-speed wireless connection 1937. Mobile device 1990 is connected to server system 1998 and network 1995. The network 1995 may include any combination of wired and wireless connections.

Figure 20:
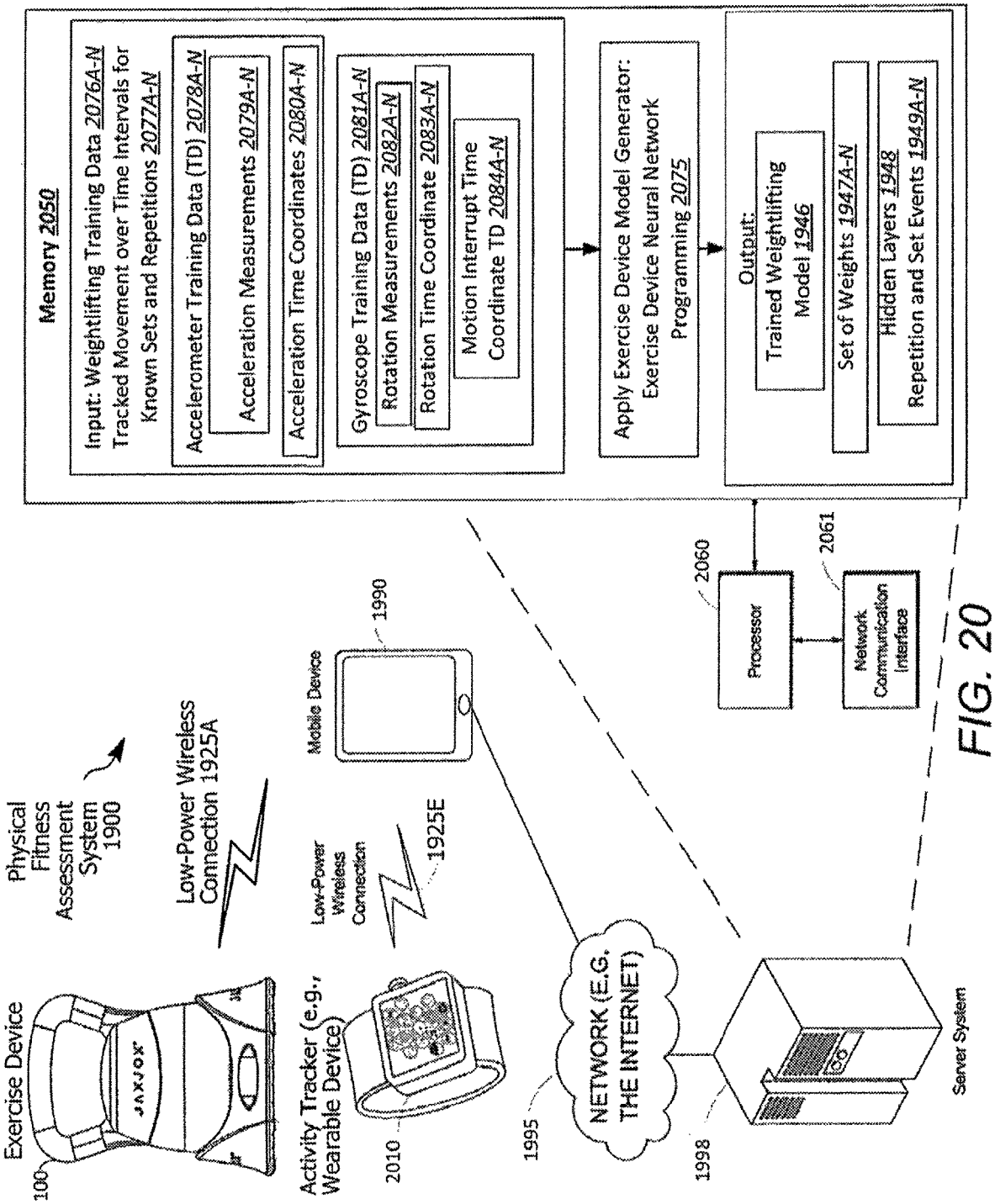
FIG. 20 shows an example of a hardware configuration for the server system of FIG. 19, for example, to build a neural network model for the exercise device, in simplified block diagram form, and an activity tracker (e.g., a wearable device).

Physical fitness assessment system 1900 includes an activity tracker 2010 (e.g., a wearable device). The activity tracker 2010 can be a watch as shown in FIG. 20, wristband, or other portable device designed to be worn by or associated with a user to communicate via one or more wireless networks or wireless links with mobile device 1990 or server system 1998.

Memory 1934 includes any storage device capable of storing various data and applications, including, among other things, model input layer 1959A-N, exercise device programming 1945, model output layer 1968A-N, selections of an amount of weight to lift 1973A-N from the user, various time durations 1974A-N, as well as images and videos generated for display by the image display driver 1942 on the image display 1980. While memory 1934 is shown as integrated with MCU 1930, in other embodiments, memory 1934 may be an independent standalone element of the exercise device 100. In certain such embodiments, electrical routing lines may provide a connection through a chip that includes the processor 1932. In other embodiments, the processor 1932 may manage addressing of memory 1934 any time that a read or write operation involving memory 1934 is needed.

As shown in FIG. 19, the exercise device 100 includes an exercise device network communication interface 1924, 1936 for communication over a network 1925, 1937. Exercise device 100 further includes a movement tracker 1918 configured to track movement of the exercise device 100, an exercise device memory 1934, and an exercise device processor 1932. The exercise device processor 1932 is coupled to the exercise device network communication interface 1924, 1936, the movement tracker 1918, and the exercise device memory 1934. The exercise device 100 includes exercise device programming 1945 in the exercise device memory 1934, Exercise device 100 can perform all or a subset of any of the following functions described below as a result of the execution of the exercise device programming 1945 in the memory 1934 by the processor 1932 of the exercise device 100. As shown in FIG. 4A, mobile device 1990 can perform all or a subset of any of the following functions described below as a result of the execution of the physical fitness assessment mobile programming 2140 in the memory 2240A by the processor 2230 of the mobile device 1990.

Execution of the exercise device programming 1945 by the processor 1932 configures the exercise device 100 to perform functions, including functions to track via the movement tracker 1918, movement of the exercise device 100 by a user. Exercise device 100 determines, a current physical activity data 1975A of the user based on, at least, the tracked movement over a time period 1960 of the exercise device 100 by the user. Exercise device 100 transmits over the network 1925, 1937 via the exercise device network communication interface 1924, 1936 the current physical activity data 1975A.

In the example of FIG. 19, the exercise device 100 can be a weight machine or a free-weight training equipment or other form of exercise or fitness equipment. As shown in FIG. 19, movement tracker 1918 includes: (i) at least one accelerometer 1920 to measure acceleration of the exercise device 100, (ii) at least one gyroscope 1921 to measure rotation of the exercise device 100, or (iii) an inertial measurement unit (IMU) 1919 having the at least one accelerometer 1920 and the at least one gyroscope 1921. The function of tracking, via the movement tracker 1918, the movement of the exercise device 100 includes: (i) measuring, via the at least one accelerometer 1920, the acceleration of the exercise device 100, (ii) measuring, via the at least one gyroscope 1921, the rotation or rotational movement of the exercise device 100, or (iii) measuring, via the inertial measurement unit 1919, both the acceleration and the rotation or rotational movement of the exercise device 100.

In one example, if the exercise device 100 is free-weight training equipment, then the free-weight training equipment is a dumbbell, a kettlebell, or a barbell. The current physical activity data 1975A Includes a number of sets 1969A-N and a number of repetitions 1970A-N determined based on the tracked movement over the time period 1960 of the exercise device 100 by the user. Here, the notation A-N corresponds to each segment in which the physical activity is divided. In the example of weightlifting, for example, the segment is a weightlifting set, where each weightlifting set s separated based on a spike in physical activity followed by significant drop as measured by the movement tracker 1918 or a clock as passage of elapsed time (e.g., 60 or 90 second breaks in between sets).

As noted above, the free-weight training equipment type of exercise device 100 includes an exercise device user input device 124 to receive from the user a selection of an amount of weight to lift 1973A-N. The exercise device 100 can further include a dock to track a time duration 1974A-N. Execution of the exercise device programming 1945 further configures the exercise device to perform functions to receive, via the exercise device user input device 124, from the user the selection of the amount of weight 1973A-N to ft. Exercise device 100 tracks, via the dock, a respective time duration 1974A-N of each set of the number of sets 1969A-N. The current physical activity data 1975A includes the selection of the amount of weight to lift 1973A-N and the respective time duration 1974A-N of each set 1969A-N.

Output components of the exercise devices 100 and 2100A-D, mobile device 1990, and wearable device 2010 optionally include visual components, such as the image display 1980, 2280, 2380 (e.g., a display such as a liquid crystal display (LCD), a plasma display panel (POP), a light emitting diode (LED) display, a projector, or a waveguide). Image displays 1980, 2280, 2380 can present images, such as in a video. The image displays 1980, 2280 are driven by the image display driver 1942, 2290, 2390. The output components of the exercise device 100, mobile device 1990, and wearable device 2010 can further include acoustic components (e.g., speakers), haptic components (e.g., a vibratory motor), other signal generators, and so forth. The input components (user input devices 124, 2291, 2391) of the exercise device 100, the mobile device 1990, activity tracker 2010, and server system 1998, may Include alphanumeric input components (e.g., a keyboard, a touch screen configured to receive alphanumeric input, a photo-optical keyboard, or other alphanumeric input components), point-based input components (e.g., a computer mouse, a touchpad, a trackball, a joystick, a motion sensor, or other pointing instruments), tactile input components (e.g., a physical button, a touch screen that provides location and force of touches or touch gestures, or other tactile input components), audio input components (e.g., a microphone), and the like.

Exercise devices 100 and 2100A-D, mobile device 1990, activity tracker 2010 (e.g., wearable device), and server system 1998 may optionally include additional peripheral device elements. Such peripheral device elements may include biometric sensors, additional sensors, or display elements integrated. For example, peripheral device elements may include any i/O components including output components, motion components, position components, or any other such elements described herein.

For example, the biometric components of the exercise devices 100 and 2100A-D, mobile device 1990, and activity tracker 2010 (e.g., wearable device) include components to detect expressions (e.g., hand expressions, facial expressions, vocal expressions, body gestures, or eye tracking), measure biosignals (e.g., blood pressure, heart rate, body temperature, breathing/respiration rate, perspiration, or brain waves), identify a person (e.g., voice identification, retinal identification, facial Identification, fingerprint identification, or electroencephalogram based identification), and the like.

The motion components include acceleration sensor components (e.g., accelerometer), gravitation sensor components, rotation sensor components (e.g., gyroscope), and so forth. The position components include location sensor components to generate location coordinates (e.g., a Global Positioning System (GPS) receiver component), WiFi or Bluetooth™ transceivers to generate positioning system coordinates, altitude sensor components (e.g., altimeters or barometers that detect air pressure from which altitude may be derived), orientation sensor components (e.g., magnetometers), and the like. Such positioning system coordinates can also be received over wireless connections 1925 and 1937 from the mobile device 1990 via the low-power wireless circuitry 1924 or high-speed wireless circuitry 1936.

Power distribution circuitry distributes power and ground voltages to the MCU 1930 from the power supply, wireless transceivers 1924, 1936, and other components to provide reliable operation of the various circuitry on the chip. Power supply 130 is driven by a power source. Power supply 130 receives power from the power source, such as an AC mains, battery, solar panel, or any other AC or DC source. Power supply 130 may include a magnetic transformer, electronic transformer, switching converter, rectifier, or any other similar type of circuit to convert an input power signal into a power signal suitable for exercise device 100. FIG. 20 shows an example of a hardware configuration for the server system 1998 of FIG. 19, for example, to build a neural network model for the exercise device, in simplified block diagram form. The activity tracker 2010 (e.g., wearable device) is connected to the mobile device 1990 via low-power wireless connection 1925E.

As further shown in FIG. 20, server system 1998 may be one or more computing devices as part of a service or network computing system, for example, that include a memory 2050, a processor 2060, a network communication interface 2061 to communicate over the network 1995 with the mobile device 1990, the exercise device 100, and the activity tracker 2010, such as a smartwatch. The memory 2050 includes weightlifting training data (TD) 2076A-N, which includes tracked movement over time intervals for known sets and repetitions 2077A-N. Weightlifting training data 2076A-N includes accelerometer training data (TD) 2078A-N. Accelerometer training data 2078A-N has acceleration measurements 2079A-N and acceleration time coordinates 2080A-N to indicate when the acceleration measurement 2079A-N was taken. Weightlifting training data 2076A-N Includes gyroscope training data 2081A-N. Gyroscope training data 2081A-N has rotation measurements 2082A-N and rotation time coordinates 2083A-N to indicate when the rotation measurement 2082A-N was taken. Weightlifting training data 2076A-N also includes motion interrupt time coordinates 2084A-N(e.g., times when motion is detected).

Memory 2050 also includes an exercise device model generator, shown as exercise device neural network programming 2075. Memory 2050 also includes trained weightlifting model 1946 which is outputted in response to applying the exercise device neural network programming 2075 to the inputted weightlifting training data 2076A-N. As shown, the output of the exercise device neural network programming 2075 includes a set of weights 1947A-N, and hidden layers 1948, such as repetition and set events 1949A-N. The trained weightlifting model 1946, set of weights 1947A-N, and hidden layers 1948 are loaded in the exercise device 100 for repetition and set detection. Alternatively, the exercise device model—trained weightlifting model 1946, set of weights 1947A-N, and hidden layers 1948 can be loaded in the mobile device 1990 and the mobile device 1990 may receive the model Input layer 1959A-N(e.g., tracked movement over time period 1960) from the exercise device via wireless connections 1925, 1937. The exercise device model, such as the trained weightlifting model 1946, may then be executed on the mobile device 1990.

Execution of the exercise device neural network programming 2075 by the processor 2060 configures the server system 1998 to perform some or all of the functions described herein before execution of the exercise device model (e.g., the trained weightlifting model 1946) by the processor 1932 of the exercise device 100. First, acquire the exercise device (e.g., weightlifting training data 1976A-N) of: (i) acceleration 1978A-N, (ii) rotation 1981A-N, or (iii) both the acceleration 1978A-N and the rotation 1981A-N of the exercise device 100 over one or more time intervals for the known sets and repetitions 1977A-N. Second, build the trained exercise device model (e.g., trained weightlifting model 1946) to identify physical activity data (e.g., sets and repetitions) correlated with the exercise device 100 based on the acquired training data 1976A-N. The function to build the exercise device model (e.g., the trained weightlifting model 1946) includes functions to calibrate the set of weights 1947A-N from the acquired training data 1976A-N of the physical activity; and store the calibrated set of weights 1947A-N In the exercise device model (e.g., the trained weightlifting model 1946) in association with the physical activity data.

Figure 21:
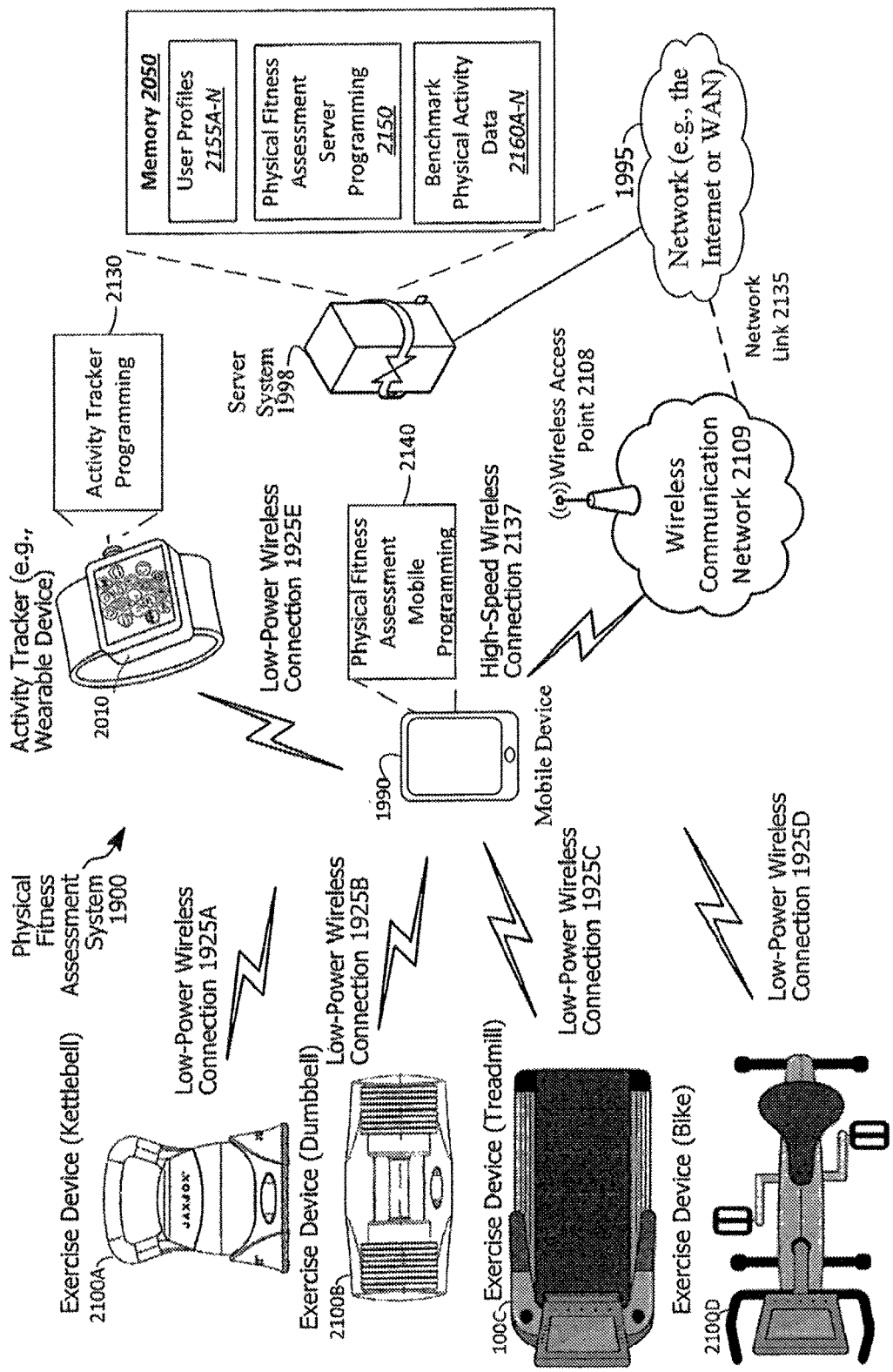
FIG. 21 is a high-level functional block diagram of an example physical fitness assessment system including multiple exercise devices, a mobile device, an activity tracker (e.g., a wearable device), and a server system connected via various networks.

FIG. 21 is a high-level functional block diagram of the example physical fitness assessment system 1900 including multiple exercise devices 2100A-D, the mobile device 1990, the activity tracker 2010 (e.g., wearable device), and the server system 1998 connected via various networks 1925A-D, 1995, 2109. Exercise devices 2100A-D provide fixed or adjustable amounts of resistance, or to otherwise enhance the experience or outcome of an exercise routine. In the fitness assessment system 1900, disparate types of exercise devices can be utilized, for example, the exercise devices 2100A-N can include a treadmill, an exercise bike, a stair machine, or an elliptical machine. Depending on the type of exercise devices 2100A-N, the movement tracker 1918 can vary, for example, the movement tracker 1918 can include a tachometer (e.g., to measure revolutions per minute of a belt of a treadmill or an exercise bike). If the length of the treadmill belt is known, distance travelled can be measured; and speed can be readily determined from the distance travelled determined using a clock to track time duration. If the exercise device 2100A-D is a rowing machine or a hand grip, then the movement tracker 1918 may be an ergometer or a dynamometer.

As shown, the exercise devices include a kettlebell 2100A, dumbbell 2100B, treadmill 2100C, and exercise bike 2100D. The exercise devices 2100A-D and the activity tracker 2010 can connect via respective low-power wireless connections 1925A-D (short-range) to the mobile device 1990; however, respective high-speed wireless connections 1937A-E (e.g., WiFi) can be implemented over the wireless communication network 2109 by accessing the wireless access point 2108. If high-speed wireless connections 1937A-E are implemented in the exercise devices 2100A-D and the activity tracker 2010, then the server system 1998 can be directly accessed without the mobile device 1990. However, in the depiction of FIG. 21, the exercise devices 2100A-D and the activity tracker 2010 can access the server system 1998 through the mobile device 1990 because the mobile device 1990 has a high-speed wireless connection 2137 (e.g., WiFi) to the wireless communication network 2109. The wireless communication network 2109 is connected to the network 1995 via a network link 2135.

As shown, the server system 1998 includes the memory 2050 and the memory includes physical fitness assessment server programming 2150. Physical fitness assessment server programming 2150 is the back-end server programming of the physical fitness assessment system 1900. Memory 2050 further includes multiple user profiles 2155A-N for many different users of the physical fitness assessment system 2155A-N. Memory 2050 further includes benchmark physical activity data 2160A-N for many different types of exercise devices 2100A-D and activity trackers 2010 for comparison purposes.

Exercise system 1900 can perform all or a subset of any of the functions described herein as a result of the execution of the exercise device programming 1945 in the memory 1934 by the processor 1932 of the exercise device 100. Mobile device 1990 can perform all or a subset of any of the functions described herein as a result of the execution of the physical fitness mobile programming 2145 in the memory 2240A by the processor 2230 of the mobile device 1990. Server system 1998 can perform all or a subset of any of the functions described herein as a result of the execution of the physical fitness server programming 2150 in the memory 2050 by the processor 2060 of the server system 1998. Functions can be divided in the physical fitness assessment system 1900, such that the host computer functions are divided up differently between the mobile device 1990 and the server system 1998 or combined to entirely occur in the mobile device 1990, entirely in the server system 1998, or even a wearable device like the smartwatch shown for the activity tracker 2010. Moreover, some of the functions attributed to the mobile device 1990 may occur in the exercise devices 2100A-D or activity tracker 2010.

The physical fitness assessment 2261 is based on activity input from multiple exercise devices 2100A-D (which track respective current physical activity data 1975A-D) and activity tracker 2010, which can be measured against the benchmark physical activity data 2160A-N that can stores guidelines from the American College of Sports Medicine. The benchmark physical activity data 2160A-N provide guidelines for specific categories of people that can be based on user profiles 2155A-N, for example, based on demographics (age, gender, race, etc.), height and weight, for example. In addition, the benchmark physical activity data 2160A-N can measured against a benchmark setting level 2281 (such as an activity level) that is set by the user, such as beginner, intermediate, or elite (target physical activity fitness level to achieve) and can account for the differences between the average person vs. athletes.

The greater the amount of current physical activity data 1975A and supplemental physical activity data 2375A and user profile settings 2256A-E for the user, the more accurate the physical fitness assessment 2261. Mobile device 1990 includes respective current physical activity data 1975A transmitted from the exercise device 100 of FIG. 19 (further shown as exercise device 2100A in FIG. 21), as well as respective current physical activity data 19758-D transmitted from respective exercise devices 2100B-D of FIG. 21. The physical fitness assessment 2261 can be based on a daily, monthly, or yearly basis and can be cumulative over time. The physical fitness assessment 2261 is displayed via the image display 2280 as the physical fitness assessment image 2262. For example, an indicator bar increases when current repetitions times weight approaches or exceeds that from a previous workout.

Benchmark physical activity 2160A-N can be personalized based on the user profile settings 2256A-E. For example, user profile settings 2256A-E can be evaluated to determine a health risk profile of the user. Race 2256E can, for example, be a significant risk factor in contributing to conditions, such as diabetes for example, and may optionally be weighed more heavily in evaluating the health risk profile of the user. If the health risk profile of the user is high for any particular condition, the benchmark physical activity data 2160A-N may be adjusted to require extra or otherwise modified physical activity to compensate for the risk profile of the user. For exercise devices 100, 2100A-B (kettlebell and dumbbell), for example, a greater number of sets 1969A-N and number of repetitions 1970A-N can be set. For exercise device 2100C (treadmill) and exercise device 2100D (bike), a greater or otherwise modified exercise time duration and distance traveled can be set. For activity tracker 2010, a greater or otherwise modified number of steps 2378A-N, distance traveled 2405A-N, calories burned 2406A-N, time duration 2377A-N, and heart rate 2376A-N can be set.

Figure 24:
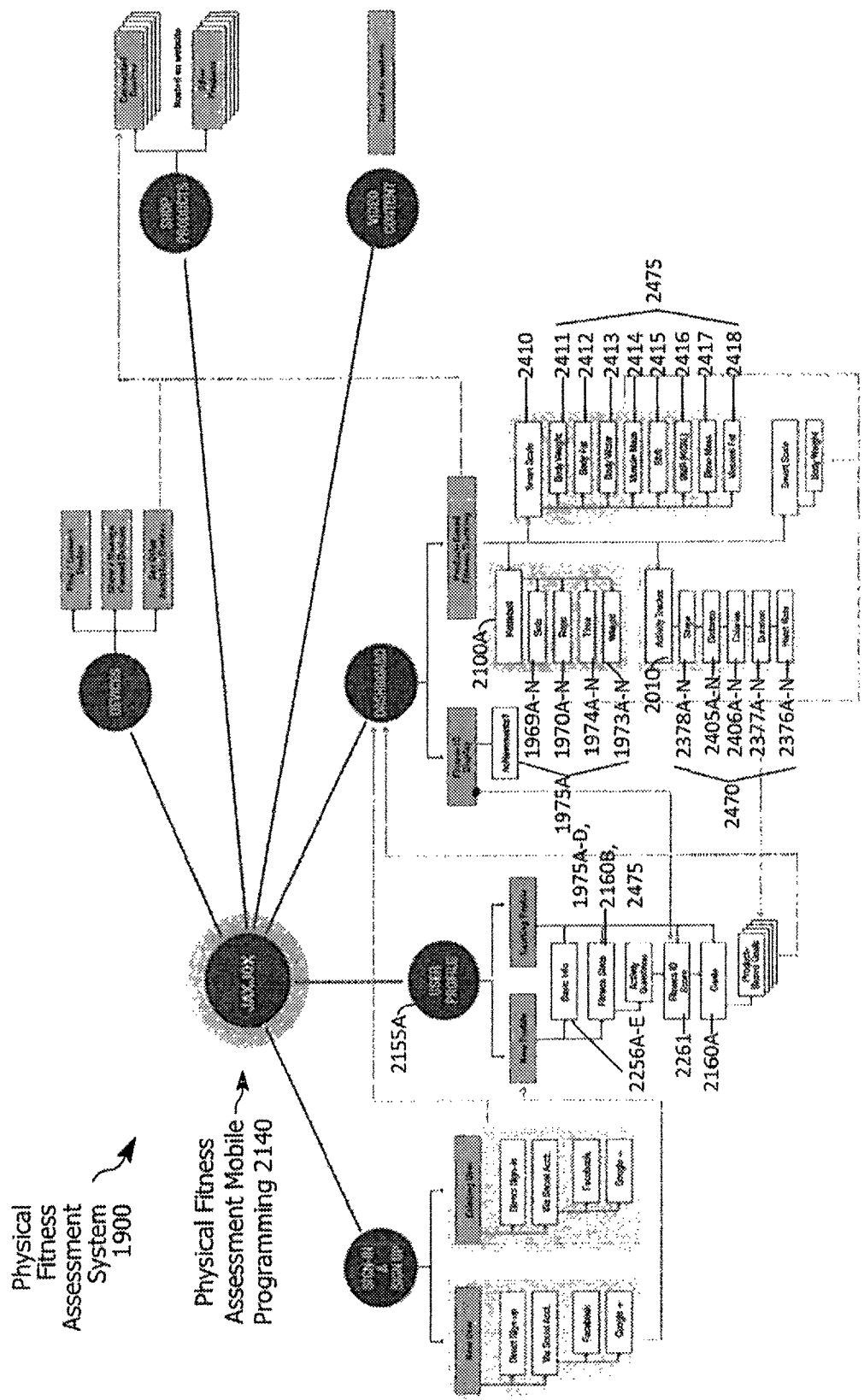
FIG. 24 shows an example of a schematic diagram of the information architecture of the physical fitness assessment system of FIGS. 19-21.

The physical fitness assessment 2261 can provide an overall indicator to the user of their physical fitness and track preset goal, for example, in a physical fitness image 2262 that is presented on the image display 2280 as a dashboard. Preset goals, can be stored in the user profile 2155A as target physical activity data 2160A. The physical fitness assessment 2261 can track the preset goals which can vary depending on the type of exercise device 2100A-Q. For exercise devices 2100A-B (e.g., kettlebell 2100A or dumbbell 2100B), preset goals can include daily or weekly number of repetitions, daily or weekly number of sets, or daily or weekly amount of weight. For activity tracker 2010 or exercise device 2100C (treadmill), preset goals can include daily steps; and minutes or hours of daily sleep for just the activity tracker 2010. As shown in FIG. 24, for a smart scale device 2410, the physical fitness assessment 2261 can track body weight 2411, body fat 2412, body water 2413, muscle mass 2414, body mass index (BMI) 2415, basal metabolic rate 2416 (BMR—e.g., in kilocalorles), bone mass 2417, and visceral fat 2418. The physical fitness assessment 2261 can track number of steps, distance, calories, time duration, and heart rate from an activity tracker 201 or exercise device 2100C (treadmill), as well as distance, calories, time duration, and heart rate from other cardiovascular exercise devices, such as exercise device 1000 (exercise bike). These metrics can be displayed in the physical fitness assessment image 2261 as a percentage of a goal or communication via audio (aural) over a speaker, etc. For the exercise device 2100A (kettlebell), time duration can be displayed towards an overall workout.

Figure 22:
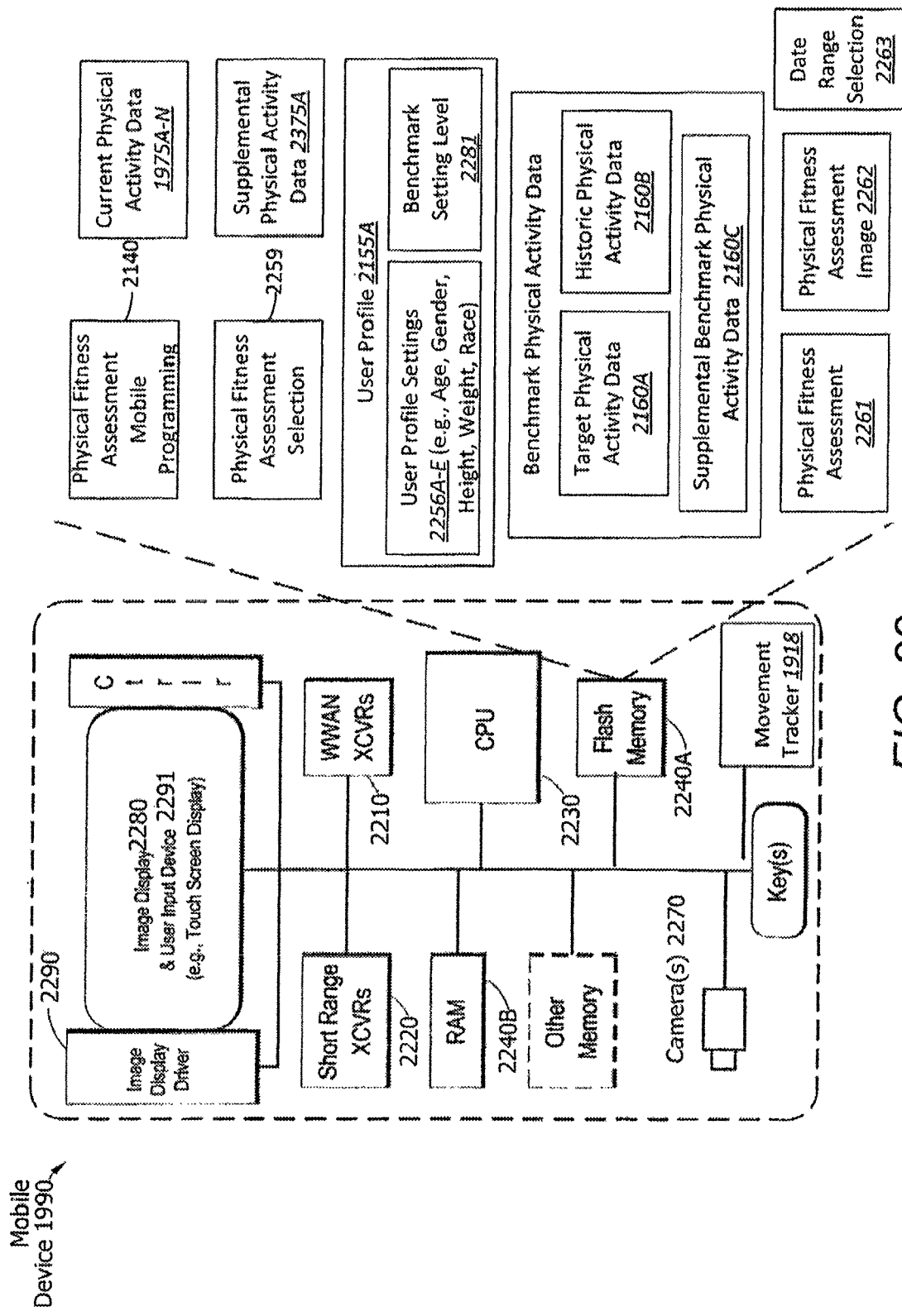
FIG. 22 shows an example of a hardware configuration for the mobile device of the physical fitness assessment systems of FIGS. 19-21.

FIG. 22 shows an example of a hardware configuration for the mobile device 1990 of the physical fitness assessment system 1900 of FIGS. 19-21. As shown in FIG. 22, the mobile device 2140 is a host computer that connects to the exercise devices 100, 2100A-D, and activity tracker 2010. As shown, the mobile device 1990 includes an image display 2280 for presenting a physical fitness assessment image 2262 based on the tracked current physical activity data 1975A of the user. The mobile device 1990 includes an image display driver 2290 coupled to the image display 2280 to control the image display 2280 to present the physical fitness assessment image 2262. The mobile device 1990 includes a user input device 2291 to receive from the user a physical fitness assessment selection 2140 to apply to the current physical activity data 1975A to generate the physical fitness assessment image 2262. The mobile device 1990 includes a network communication interface for communication over the network, a host computer memory 2240A-B, and a processor 2230 coupled to the image display driver 2290, the user input device 2291, and the network communication interface (short range transceivers 2220 and wireless area network transceivers 2210). The mobile device 1990 includes host computer programming, shown as physical fitness assessment mobile programming 2140 in the memory 2250A.

Execution of the physical fitness assessment mobile programming 2140 by the processor 2230 configures the mobile device 1990 to performs functions. Mobile device 1990 receives over the network 1925, 1937, via the network communication interface 2220, from the exercise device 100 the tracked current physical activity data 1975A of the user. Mobile device 1990 receives, via the user input device 2291, the physical fitness assessment selection 2259 to apply to the current physical activity data 1975A. Mobile device 1990 compares the current physical activity data 1975A of the user against benchmark physical activity data, shown as target physical activity data 2160A and historic physical activity data 2160B, correlated with the exercise device 2100A-D. Based on the comparison, mobile device 1990 determines a physical fitness assessment 2261 of the user. Mobile device 1990 generates, the physical fitness assessment image 2262, based on the physical fitness assessment 2261 of the user. Mobile device 1990 presents, via the image display 2280, the physical fitness assessment image 2262.

In one example, execution of the physical fitness mobile programming 2140 by the processor 2230 further configures the mobile device 1990 to perform functions to receive, via the user input device 2291, from the user a profile setting 2256A-E that includes an age 2256A, a gender 22568, a height 2256C, a weight 2256D, or a race 2256E. Mobile device 1990 sets a user profile 2155A of the user stored in the memory 2240A In response to the received profile setting 2256A-E. Mobile device 1990 receives, via the user input device 2291, from the user a benchmark setting level 2281 (beginner, intermediate, or elite—target physical activity fitness level to achieve). Mobile device 1990 adjusts the benchmark physical activity data to a target physical activity data 2160A based on the user profile setting 2256A-E and the received benchmark setting level 2281.

Execution of the physical fitness mobile programming 2140 by the processor 2230 further configures the mobile device 1990 to perform functions to receive, via the user input device 2291, from the user a date range 2263 of a historic physical activity data 2160B of the user during which a previous physical activity data of the user was tracked. Mobile device 1990 adjusts the benchmark physical activity data based on the historic physical activity data 2160B of the user.

Figure 23:
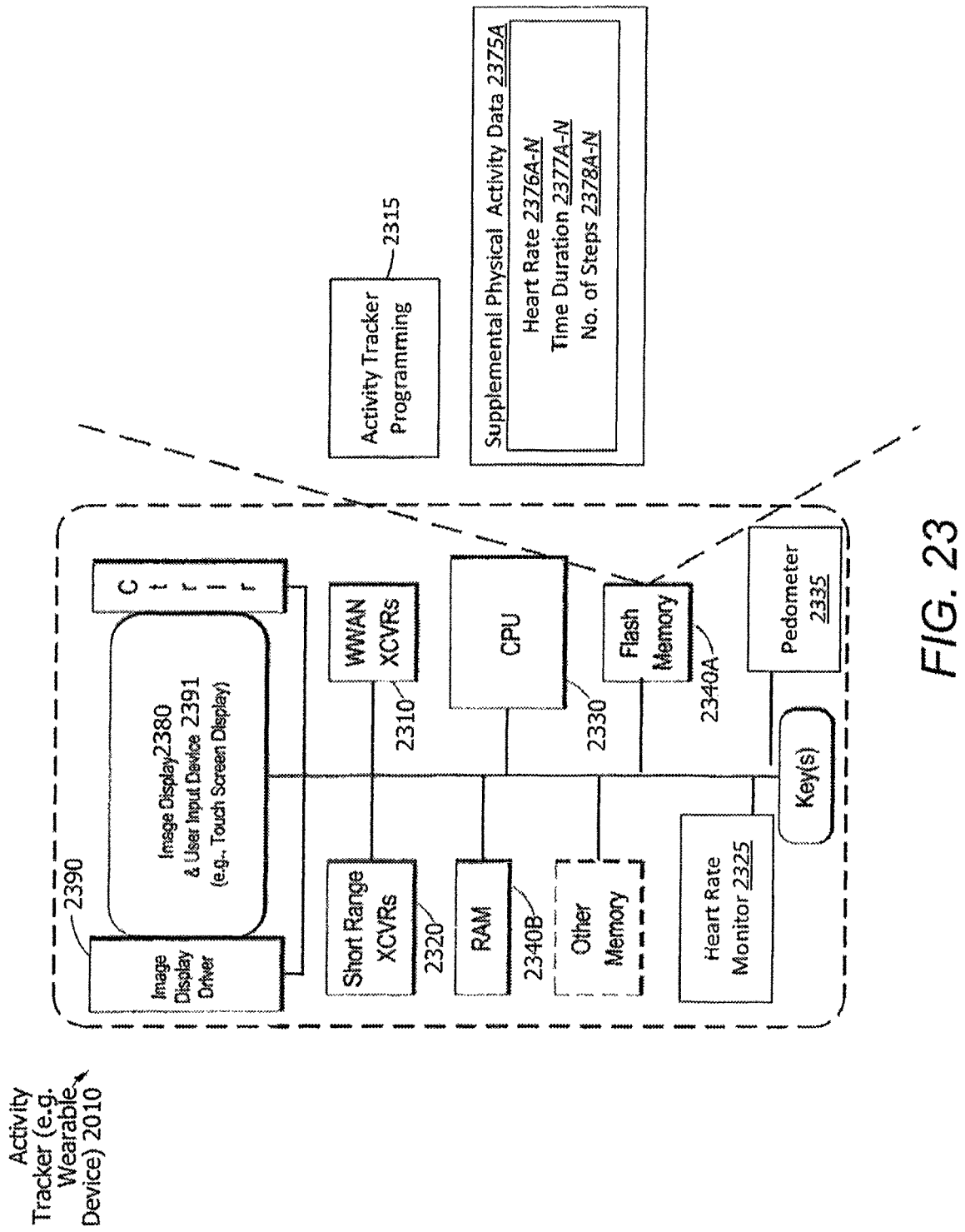
FIG. 23 shows an example of a hardware configuration for the activity tracker of the physical fitness assessment systems of FIGS. 20-21.

FIG. 23 shows an example of a hardware configuration for the activity tracker 2010 of the physical fitness assessment system 1900 of FIGS. 20-21. The physical fitness assessment system 1900 includes the activity tracker 2010 to monitor physical activity of the user. As shown, the activity tracker 2010 includes an activity tracker device network communication interface (e.g., short range XCVRs 2320 for communication over the network 1925E) for communication over the network 1995. Activity tracker 2010 includes a heart rate monitor 2325 configured track a heart rate 2376A-N of the user. Activity tracker 2010 further includes an activity tracker device memory 2340A, an activity tracker processor 2330 coupled to the activity tracker network communication interface 2320, the heart rate monitor 2325, and the activity tracker memory 2240A. Activity tracker 2010 further includes activity tracker programming 2315 in the activity tracker memory 2340A.

Execution of the activity tracker programming 2315 by the activity tracker processor 2330 configures the activity tracker 2010 to perform functions to track, via the heart rate monitor 2325, the heart rate 2376A-N of the user over a time duration 2377A-N. Activity tracker 2010 determines, a supplemental physical activity data 2375A of the user based on the monitored heart rate 2376A-N over the time duration 2377A-N. Activity tracker 2010 transmits over the network 1925E to the mobile device 1990, via the activity tracker network communication interface 2320, the supplemental physical activity data 2375A of the user.

Execution of the physical fitness mobile programming 2140 by the processor 2230 further configures the mobile device 1990 to performs functions to receive over the network 1925E, via the network communication interface 2220, from the activity tracker 2010 the tracked supplemental physical activity data 2375A of the user. Mobile device 1990 compares the supplemental physical activity data 2375A of the user against correlated with the activity tracker 2010. The function of the determining the physical fitness assessment 2261 of the user is further based on the comparison of the supplemental physical activity data 2375A against the supplemental benchmark physical activity data 2160C.

In the example, the activity tracker 2010 further includes a pedometer 2335 configured to track a number of steps 2378A-N of the user over the time duration 2377A-N. The activity tracker processor 2010 is coupled to the pedometer 2335. Execution of the activity tracker programming 2310 by the activity tracker processor 2330 further configures the activity tracker 2010 to perform functions to monitor, via the pedometer 2335, the number of steps 2378A-N of the user over the time duration 2377A-N. Activity tracker 2010 determines, the supplemental physical activity data 2375A of the user further based on the monitored number of steps 2378A-N over the time duration 2377A-N.

As shown in FIGS. 22-23, the activity tracker 2010 or the mobile device 1990 includes an image display 2280, 2380 and an image display driver 2290, 2390 to control the image display 2280, 2380. The image display 2280, 2380 and a user input device 2291, 2391 are integrated together into a touch screen display. Examples of touch screen type mobile devices that may be used include (but are not limited to) a smart phone, a personal digital assistant (PDA), a tablet computer, a laptop computer, or other portable device. However, the structure and operation of the touch screen type devices is provided by way of example; and the subject technology as described herein is not intended to be limited thereto. For purposes of this discussion, FIGS. 22-23 therefore provide block diagram illustrations of the example mobile device 390 and the activity tracker 2010 having a touch screen display for displaying content and receiving user input as (or as part of) the user interface.

The activities that are the focus of discussions here typically involve data communications related to detecting physical activity of a user of exercise devices 100, 2100A-D, and activity tracker 2010 (e.g., wearable device), and the mobile device 1990 to provide a physical fitness assessment 2261. As shown in FIGS. 22-23, the mobile device 2290 and the activity tracker 2010 includes at least one digital transceiver (XCVR), shown as WWAN XCVRs 2210, 2310, for digital wireless communications via a wide area wireless mobile communication network. The mobile device 1990 and the activity tracker 2010 also includes additional digital or analog transceivers, such as short range XCVRs 2220, 2320 for short-range network communication, such as via NFC, VLC, DECT, ZigBee, Bluetooth™, or WiFi. For example, short range XCVRs 2220, 2320 may take the form of any available two-way wireless local area network (WLAN) transceiver of a type that is compatible with one or more standard protocols of communication implemented in wireless local area networks, such as one of the WI-FI standards under iEEE 802.11 and WiMAX.

To generate location coordinates for positioning of the mobile device 1990 and the activity tracker 2010, the mobile device 1990 and the activity tracker 2010 can include a global positioning system (GPS) receiver. Alternatively, or additionally the mobile device 1990 and the activity tracker 2010 can utilize either or both the short range XCVRs 2220, 2320 and WWAN XCVRs 2210, 2310 for generating location coordinates for positioning. For example, cellular network, WiFi, or Bluetooth™ based positioning systems can generate very accurate location coordinates, particularly when used in combination. Such location coordinates can be transmitted to the exercise device 100, 2100A-D over one or more network connections via XCVRs 2210, 2220, 2310, 2320.

The transceivers 2210, 2220, 2310, 2320 (network communication interfaces) conform to one or more of the various digital wireless communication standards utilized by modern mobile networks. Examples of WWAN transceivers 2210, 2310 include (but are not limited to) transceivers configured to operate in accordance with Code Division Multiple Access (CDMA) and 3rd Generation Partnership Project (3GPP) network technologies including, for example and without limitation, 3GPP type 2 (or 3GPP2) and LTE, at times referred to as "4G." For example, the transceivers 2210, 2220, 2310, 2320 provide two-way wireless communication of Information including digitized audio signals, still image and video signals, web page information for display as well as web related inputs, and various types of mobile message communications to/from the mobile device 1990 or the activity tracker 2010 for the physical fitness assessment system 1900.

Several of these types of communications through the transceivers 2210, 2220, 2310, 2320 and a network, as discussed previously, relate to protocols and procedures in support of communications to detect physical activity of a user of exercise devices 100, 2100A-D, activity tracker 2010 (e.g., wearable device), and the mobile device 1990 to provide a physical fitness assessment 2261. Such communications, for example, may transport packet data via the short range XCVRs 2220 over the wireless connections 1925 and 1937 to and from the exercise devices 100, 2100A-D as shown in FIGS. 19-21. Such communications, for example, may also transport data utilizing iP packet data transport via the WWAN XCVRs 2210, 2310 over the network (e.g., Internet) 1995 shown in FIGS. 19-21. Both WWAN XCVRs 2210, 2310 and short range XCVRs 2220, 2320 connect through radio frequency (RF) send-and-receive amplifiers (not shown) to an associated antenna (not shown).

The fitness tracker 2010 and the mobile device 1990 further includes a microprocessor, shown as CPU 2230, 2330 sometimes referred to herein as the host controller. A processor is a circuit having elements structured and arranged to perform one or more processing functions, typically various data processing functions. Although discrete logic components could be used, the examples utilize components forming a programmable CPU. A microprocessor for example includes one or more Integrated circuit (IC) chips incorporating the electronic elements to perform the functions of the CPU. The processor 2230, 2330 for example, may be based on any known or available microprocessor architecture, such as a Reduced instruction Set Computing (RISC) using an ARM architecture, as commonly used today in mobile devices and other portable electronic devices. Of course, other processor circuitry may be used to form the CPU 2230, 2330 or processor hardware in smartphone, laptop computer, and tablet.

The microprocessor 2230, 2330 serves as a programmable host controller for the mobile device 1990 and the activity tracker 2010 by configuring the mobile device 1990 and the activity tracker 2010 to perform various operations, for example, in accordance with instructions or programming executable by processor 2230, 2330. For example, such operations may include various general operations of the mobile device 1990 and the activity tracker 2010, as well as operations related to the physical fitness mobile programming 2140, activity tracker programming 2310, and communications with the exercise devices 100, 2100A-D and server system 1998. Although a processor may be configured by use of hardwired logic, typical processors in mobile devices are general processing circuits configured by execution of programming.

The mobile device 1990 and the activity tracker 2010 includes a memory or storage device system, for storing data and programming. In the example, the memory system may include a flash memory 2240A, 2340A and a random access memory (RAM) 2240B, 2340B. The RAM 2240B, 2340B serves as short term storage for instructions and data being handled by the processor 2230, 2330 e.g. as a working data processing memory. The flash memory 2240A, 2340A typically provides longer term storage. Mobile device 1990 and the activity tracker 2010 can include a visible light camera 2270 and movement tracker 1918, like that shown for mobile device 1990 in FIG. 22.

Hence, in the example of mobile device 1990 and activity tracker 2010, the flash memory 2240A, 2340A is used to store programming or instructions for execution by the processor 2230. Depending on the type of device, the mobile device 1990 and activity tracker 2010 stores and runs a mobile operating system through which specific applications, are executed. Applications, such as the physical fitness assessment programming 2140 and activity tracker programming 2310, may be a native application, a hybrid application, or a web application (e.g., a dynamic web page executed by a web browser) that runs on mobile device 1990 or activity tracker 2010. Examples of mobile operating systems include Google Android, Apple iOS (I-Phone or iPad devices), Windows Mobile, Amazon Fire OS, RIM BlackBerry operating system, or the like.

It will be understood that the mobile device 1990 is just one type of host computer in the physical fitness assessment system 1900 and that other arrangements may be utilized. For example, a server system 998, such as that shown In FIGS. 19-21 may be utilized.

FIG. 24 shows a schematic diagram of the information architecture of the physical fitness assessment system 1900 of FIGS. 19-21. As shown, the physical fitness assessment mobile programming 2140 implemented by the mobile device 1990 enables sign-up for the physical fitness assessment system 1900 for a new user utilizing a social media account (e.g., Facebook or Google+) or a direct sign-in account. During sign-up, the user creates a new user profile 2155A. After sign-in by the user, the physical fitness assessment mobile programming 2140 loads the existing user profile 2155A for the existing user.

The user profile 2155A Includes profile settings 2256A-E that can include basic information such as an age 2256A, a gender 2256B, a height 2256C, a weight 2256D, a race 2256E, or another profile designator relating to a physical or other condition or characteristic of the user. The profile may include fitness preset goals or benchmark physical activity data, such as target physical activity data 2160A. Physical fitness statistics can be generated and presented to the user on the image display 2280 of the mobile device 1990, such as transmitted current physical activity data 1975A-D from the various exercise devices 100, 2100A-D, as well as historic physical activity data 2160B. The physical fitness assessment 2261, shown as Fitness IQ Score, can track the preset goals which can vary depending on the type of exercise device 2100A-0.

As further shown, product-based physical fitness tracking enables current physical activity data 1975A-N to be tracked by the exercise devices 100, 2100A-D, activity tracker 2010, and smart scale device 2410, and then transmitted to the mobile device 1990. The current physical activity data 1975A-N is then received by the mobile device 1990, and presented to the user on the image display 2280 of the mobile device 1990 as physical fitness statistics, which can include current physical activity data 1975A-D and historical physical activity data 2160B. Alternatively, the mobile device 1990 compares the current physical activity data 1975A-N of the user against benchmark physical activity data correlated with the exercise device, activity tracker 2010, or smart scale device; and based on the comparison, the mobile device 1990 determines the physical fitness assessment 2261 of the user.

For the activity tracker 2010, the current physical activity data 2470 includes number of steps 2378A-N, distance traveled 2405A-N, calories burned 2406A-N, time duration 2377A-N, and heart rate 2376A-N, for example, where A-N correspond to various segments of divided physical activity (e.g., as divided by physical activity bursts or time). For the kettlebell exercise device 100, 2100A (or the dumbbell exercise 2100B), the current physical activity data 1975A includes the number of sets 1969A-N, the number of repetitions 1970A-N, the time duration 1974A-N, and amount of weight 1973A-N.

For the smart scale device 2410, the current physical activity data 2475 includes various physical attributes. For example, the current physical activity data 2475 optionally includes body weight 2411, body fat 2412, body water 2413, muscle mass 2414, body mass index (BMI) 2415, basal metabolic rate 2416 (BMR—e.g., in kilocalories), bone mass 2416, and/or visceral fat 2418.

Figure 25:
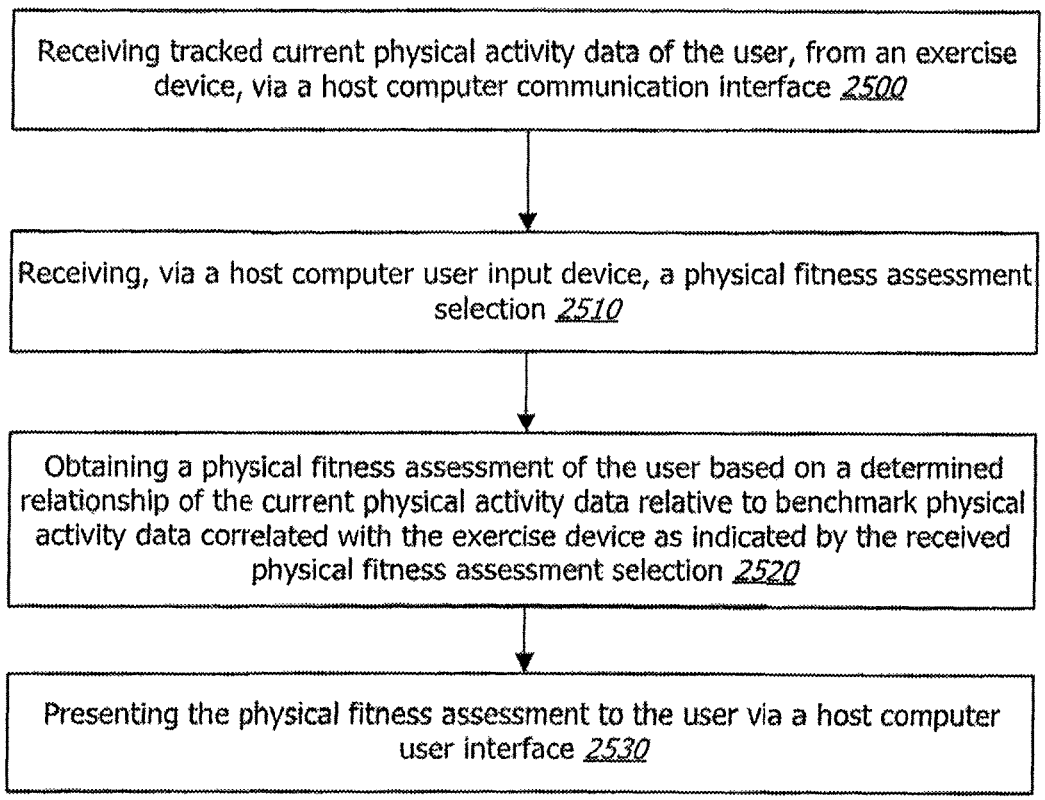
FIG. 25 is a flow diagram that shows an example of a method of providing a physical fitness assessment to a user.

FIG. 25 is a flow diagram that shows an example of a method of providing a physical fitness assessment 2261 to a user that can be implemented in the physical fitness mobile programming 2140 of the mobile device 1990. Beginning in block 2500, the method includes receiving tracked current physical activity data 1975A-N of the user, from an exercise device 100, 2100A-D, via a host computer communication interface 2220. Proceeding to block 2510, the method further includes receiving, via a host computer user input device 2291, a physical fitness assessment selection 2259. Continuing to block 2520, the method further includes obtaining a physical fitness assessment 2261 of the user based on a determined relationship of the current physical activity data 1975A-N relative to benchmark physical activity data 2160A-N correlated with the exercise device 100, 2100A-D as indicated by the received physical fitness assessment selection 2259.

Finishing now in block 2530, the method further includes presenting the physical fitness assessment 2261 to the user via a host computer user interface 2280. In some examples, a subset or all of the blocks may be implemented in the exercise device programming 1945, physical fitness assessment server programming 2150, or the activity tracker programming 2315.

Any of the functionality described herein for the exercise devices 100, 2100A-D, activity tracker 2010, mobile device 1990, server system 1998, and smart scale device 2410 can be embodied in one more applications or firmware as described previously and stored in a machine-readable medium. According to some embodiments, "function," "functions," "application," "applications," "Instruction," "instructions," or "programming" are program(s) that execute functions defined in the programs. Various programming languages can be employed to create one or more of the applications, structured in a variety of manners, such as object-oriented programming languages (e.g., Objective-C, Java, or C++) or procedural programming languages (e.g., C or assembly language). In a specific example, a third party application (e.g., an application developed using the ANDROID™ or iOS™ software development kit (SDK) by an entity other than the vendor of the particular platform) may be mobile software running on a mobile operating system such as iOS™, ANDROID™, WINDOWS® Phone, or another mobile operating systems. In this example, the third party application can invoke API calls provided by the operating system to facilitate functionality described herein.

Hence, a machine-readable medium may take many forms of tangible storage medium. Non-volatile storage media include, for example, optical or magnetic disks, such as any of the storage devices in any computer(s) or the like, such as may be used to implement the exercise devices 100, 2100A-D, activity tracker 2010, mobile device 1990, server system 1998, and smart scale device 2410 shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more Instructions to a processor for execution.

While preferred embodiments of the invention have been shown and described herein, it will be understood that such embodiments are provided by way of example only. Numerous variations, changes and substitutions will occur to those skilled in the art without departing from the spirit or principle of the invention. Accordingly, it is intended that the appended claims cover all such variations as fall within the spirit, scope, or principle of the invention.

What is claimed is:
1. A physical fitness assessment system comprising:
an exercise device including:
  an exercise device network communication interface for communication over a network;
  a movement tracker configured to track movement of the exercise device;
  an exercise device memory;
  an exercise device processor coupled to the exercise device network communication interface, the movement tracker, and the exercise device memory; and
  exercise device programming in the exercise device memory, wherein execution of the exercise device programming by the exercise device processor configures the exercise device to perform functions to:
    track, via the movement tracker, movement of the exercise device by a user;
    determine a current physical activity data of the user based on, at least, the tracked movement of the exercise device by the user; and
    transmit over the network, via the exercise device network communication interface, the current physical activity data of the user; and
a host computer including:
  an image display for presenting a physical fitness assessment image based on the current physical activity data of the user;
  an image display driver coupled to the image display to control the image display to present the physical fitness assessment image;
  a host computer user input device to receive from the user a physical fitness assessment selection to apply to the current physical activity data to generate the physical fitness assessment image;
  a host computer network communication interface for communication over the network;

a host computer memory;

a host computer processor coupled to the image display driver, the host computer user input device, and the host computer network communication interface; and host computer programming in the host computer memory, wherein execution of the host computer programming by the host computer processor configures the host computer to perform functions, including functions to:

receive over the network, via the host computer network communication interface, from the exercise device the current physical activity data of the user;

receive, via the host computer user input device, the physical fitness assessment selection to apply to the current physical activity data;

compare the current physical activity data of the user against benchmark physical activity data correlated with the exercise device;

based on the comparison, determine a physical fitness assessment of the user;

generate the physical fitness assessment image based on the physical fitness assessment of the user; and present, via the image display, the physical fitness assessment image.

2. The physical fitness assessment system of claim 1, further comprising:

an activity tracker to monitor physical activity of the user, the activity tracker including:

an activity tracker device network communication interface for communication over the network;

a heart rate monitor configured to track a heart rate of the user;

an activity tracker device memory;

an activity tracker processor coupled to the activity tracker network communication interface, the heart rate monitor, and the activity tracker memory; and activity tracker programming in the activity tracker memory, wherein execution of the activity tracker programming by the activity tracker processor configures the activity tracker to perform functions to:

track, via the heart rate monitor, the heart rate of the user over a time duration;

determine a supplemental physical activity data of the user based on the monitored heart rate over the time duration; and transmit over the network to the host computer, via the activity tracker network communication interface, the supplemental physical activity data of the user.

3. The physical fitness assessment system of claim 2, wherein:

execution of the host computer programming by the host computer processor further configures the host computer to perform functions to:

receive over the network, via the host computer network communication interface, from the activity tracker the tracked supplemental physical activity data of the user;

compare the supplemental physical activity data of the user against supplemental benchmark physical activity data correlated with the activity tracker; and the function of the determining the physical fitness assessment of the user is further based on the comparison of the supplemental physical activity data against the supplemental benchmark physical activity data.

4. The physical fitness assessment system of claim 3, wherein:

the activity tracker further includes a pedometer configured to track a number of steps of the user over the time duration;

the activity tracker processor is coupled to the pedometer; and execution of the activity tracker programming by the activity tracker processor further configures the activity tracker to perform functions to:

monitor, via the pedometer, the number of steps of the user over the time duration; and determine the supplemental physical activity data of the user further based on the monitored number of steps over the time duration.

5. The physical fitness assessment system of claim 2, wherein the activity tracker is a wearable device.

6. The physical fitness assessment system of claim 1, wherein:

the exercise device is a weight machine or a free-weight training equipment;

the movement tracker includes:

(i) at least one accelerometer to measure acceleration of the exercise device, (ii) at least one gyroscope to measure rotation of the exercise device, or (iii) an inertial measurement unit (IMU) having the at least one accelerometer and the at least one gyroscope; and the function of tracking, via the movement tracker, the movement of the exercise device includes:

(i) measuring, via the at least one accelerometer, the acceleration of the exercise device, (ii) measuring, via the at least one gyroscope, the rotation of the exercise device, or (iii) measuring, via the inertial measurement unit, both the acceleration and the rotation of the exercise device.

7. The physical fitness assessment system of claim 6, wherein:

the exercise device is the free-weight training equipment;

the free-weight training equipment is a dumbbell, a kettlebell, or a barbell; and the current physical activity data includes a number of sets and a number of repetitions determined based on the tracked movement of the exercise device by the user.

8. The physical fitness assessment system of claim 7, wherein:

the free-weight training equipment includes:

an exercise device user input device to receive from the user a selection of an amount of weight to lift; and a clock to track a time duration;

execution of the exercise device programming further configures the exercise device to perform functions to:

receive, via the exercise device user input device, from the user the selection of the amount of weight to lift; and track, via the clock, a respective time duration of each set of the number of sets; and the current physical activity data includes the selection of the amount of weight to lift and the respective time duration of each set.

9. The physical fitness assessment system of claim 1, wherein:
- execution of the host computer programming by the host computer processor further configures the host computer to perform functions to:
  - receive, via the host computer user input device, from the user a profile setting that includes at least one of an age, a gender, a height, a weight, or a race;
  - set a user profile of the user stored in the host computer memory in response to the received profile setting;
  - receive, via the user input device, from the user a benchmark setting level; and
  - adjust the benchmark physical activity data to a target physical activity data based on the user profile setting and the received benchmark setting level.

10. The physical fitness assessment system of claim 1, wherein:
- execution of the host computer programming by the host computer processor further configures the host computer to perform functions to:
  - receive, via the host computer user input device, from the user a date range of a historic physical activity data of the user during which a previous physical activity data of the user was tracked; and
  - adjust the benchmark physical activity data based on the historic physical activity data of the user.

11. The physical fitness assessment system of claim 1, wherein:
- the exercise device is a treadmill, an exercise bike, a stair machine, or an elliptical machine; and
- the movement tracker includes a tachometer, an ergometer, or a dynamometer.

12. The physical fitness assessment system of claim 1, wherein:
- the host computer is a mobile device or a server system;
- the network is a wireless short-range network or a wireless local area network; and
- the host computer user input device includes a touch screen or a computer mouse.

13. A method of providing a physical fitness assessment to a user using the physical fitness assessment system of claim 1, the method comprising:
- tracking, via the movement tracker of the exercise device, movement of the exercise device by the user;
- determining the current physical activity data of the user based on, at least, the tracked movement of the exercise device by the user;
- transmitting over the network, via the exercise device network communication interface of the exercise device, the current physical activity data of the user;
- receiving the transmitted current physical activity data of the user, from the exercise device, via the host computer network communication interface of the host computer;
- receiving, via the host computer user input device of the host computer, the physical fitness assessment selection to apply to the current physical activity data;
- determining the physical fitness assessment of the user based on a comparison of the current physical activity data of the user against the benchmark physical activity data correlated with the exercise device as indicated by the received physical fitness assessment selection; and
- presenting the physical fitness assessment to the user via a host computer user interface.

14. The method of claim 13, further comprising:
- receiving, via the host computer user input device, from the user a profile setting that includes at least one of an age, a gender, a height, a weight, or a race;
- setting a user profile of the user in response to the received profile setting;
- receiving, via the host computer user input device, from the user a benchmark setting level; and
- adjusting the benchmark physical activity data to a target physical activity data based on the user profile setting and the received benchmark setting level.

15. The method of claim 13, further comprising:
- receiving, via the host computer user input device, from the user a date range of a historic physical activity data of the user during which a previous physical activity data of the user was tracked; and
- adjusting the benchmark physical activity data based on the historic physical activity data of the user.

16. The method of claim 13, further comprising:
- receiving from an activity tracker a supplemental physical activity data of the user determined based on a heart rate of the user monitored over a time duration;
- comparing the supplemental physical activity data of the user against supplemental benchmark physical activity data; and
- the step of obtaining the physical fitness assessment of the user is further based on the comparison of the supplemental physical activity data against the supplemental benchmark physical activity data.

* * * * *